(12) United States Patent
Choi

(10) Patent No.: US 9,034,848 B2
(45) Date of Patent: May 19, 2015

(54) PHENYL CARBAMATE COMPOUNDS FOR USE IN PREVENTING OR TREATING STROKE

(71) Applicant: Bio-Pharm Solutions Co., Ltd., Gyeonggi-do (KR)

(72) Inventor: Yong Moon Choi, Irvine, CA (US)

(73) Assignee: Bio-Pharm Solutions Co., Ltd. (KR)

( * ) Notice: Subject to any disclaimer, the term of this patent is extended or adjusted under 35 U.S.C. 154(b) by 190 days.

(21) Appl. No.: 13/727,665

(22) Filed: Dec. 27, 2012

(65) Prior Publication Data

US 2013/0165410 A1    Jun. 27, 2013

Related U.S. Application Data

(60) Provisional application No. 61/580,409, filed on Dec. 27, 2011.

(51) Int. Cl.
| | | |
|---|---|---|
| A61K 31/047 | (2006.01) | |
| A61K 31/164 | (2006.01) | |
| A61K 31/165 | (2006.01) | |
| C07C 271/02 | (2006.01) | |
| C07C 33/26 | (2006.01) | |
| C07C 271/12 | (2006.01) | |
| C07C 271/24 | (2006.01) | |
| C07F 7/18 | (2006.01) | |
| C07C 271/28 | (2006.01) | |
| C07C 271/16 | (2006.01) | |
| A61K 31/325 | (2006.01) | |

(52) U.S. Cl.
CPC ............. *C07C 271/02* (2013.01); *A61K 31/165* (2013.01); *A61K 31/047* (2013.01); *A61K 31/164* (2013.01); *C07C 33/26* (2013.01); *C07C 271/12* (2013.01); *C07C 271/24* (2013.01); *C07F 7/1804* (2013.01); *C07C 271/28* (2013.01); *C07C 271/16* (2013.01); *A61K 31/325* (2013.01); *C07C 2101/02* (2013.01); *C07C 2101/14* (2013.01); *C07C 2102/42* (2013.01)

(58) Field of Classification Search
CPC .. A61K 31/047; A61K 31/164; A61K 31/165
See application file for complete search history.

(56) References Cited

U.S. PATENT DOCUMENTS

| | | |
|---|---|---|
| 2,884,444 A | 4/1959 | Berger et al. |
| 2,937,119 A | 5/1960 | Berger et al. |
| 3,265,727 A | 8/1966 | Bossinger et al. |
| 3,265,728 A | 8/1966 | Bossinger et al. |
| 3,313,692 A | 4/1967 | Bossinger et al. |
| 3,313,696 A | 4/1967 | Bossinger et al. |
| 3,313,699 A | 4/1967 | Bossinger et al. |
| 3,313,700 A | 4/1967 | Bossinger et al. |
| 3,600,427 A | 8/1971 | Verbiscar |
| 6,103,759 A | 8/2000 | Choi et al. |
| 7,385,076 B2 | 6/2008 | Patel et al. |
| 7,442,438 B2 | 10/2008 | Boulos et al. |
| 7,737,141 B2 | 6/2010 | Kimura et al. |
| 2001/0034365 A1 | 10/2001 | Choi et al. |
| 2002/0156127 A1 | 10/2002 | Plata-salaman et al. |
| 2002/0165273 A1 | 11/2002 | Plata-Salaman et al. |
| 2004/0138299 A1 | 7/2004 | Cahill et al. |
| 2006/0194873 A1 | 8/2006 | Choi et al. |
| 2008/0090903 A1 | 4/2008 | Pandey et al. |
| 2008/0103198 A1 | 5/2008 | Haas |
| 2008/0317883 A1 | 12/2008 | Choi et al. |
| 2009/0048213 A1 | 2/2009 | Kimura et al. |
| 2009/0221640 A1 | 9/2009 | Briggner et al. |
| 2010/0048629 A1 | 2/2010 | Gage |
| 2012/0184762 A1 | 7/2012 | Choi |
| 2013/0005801 A1 | 1/2013 | Choi |
| 2013/0165408 A1 | 6/2013 | Choi et al. |
| 2013/0165509 A1 | 6/2013 | Choi |
| 2013/0184338 A1 | 7/2013 | Choi |
| 2013/0203846 A1 | 8/2013 | Choi |
| 2014/0051753 A9 | 2/2014 | Choi |

FOREIGN PATENT DOCUMENTS

| | | |
|---|---|---|
| CN | 1208402 A | 2/1999 |
| CN | 1536992 A | 10/2004 |
| CN | 1536993 A | 10/2004 |
| CN | 101208402 A | 6/2008 |
| CN | 101472913 A | 7/2009 |
| JP | 61-271992 A | 12/1986 |
| WO | WO-2006/033947 A2 | 3/2006 |
| WO | WO-2008/013213 A1 | 1/2008 |

(Continued)

OTHER PUBLICATIONS

U.S. Appl. No. 13/727,659, Non Final Office Action mailed Apr. 22, 2014, 6 pgs.
U.S. Appl. No. 13/727,654, Response filed Aug. 16, 2013 to Restriction Requirement mailed Jul. 31, 2013, 6 pgs.
U.S. Appl. No. 13/727,654, Restriction Requirement mailed Jul. 31, 2013, 7 pgs.
International Application Serial No. PCT/KR2012/011469, International Search Report nailed Apr. 22, 2013, 4 pgs.
International Application Serial No. PCT/KR2012/011469, Written Opinion mailed Apr. 22, 2013, 7 pgs.
International Application Serial No. PCT/KR2012/011470. International Search Report mailed Apr. 22, 2013, 4 pgs.
International Application Serial No. PCT/KR2012/011470, Written Opinion mailed Apr. 22, 2013, 5 pgs.

(Continued)

*Primary Examiner* — Yong Chong
(74) *Attorney, Agent, or Firm* — Schwegman Lundberg & Woessner, P.A.

(57) ABSTRACT

A phenyl carbamate compound; a composition for treating and/or preventing stroke containing the phenyl carbamate compound or a pharmaceutically acceptable salt thereof as an active ingredient; a method of treating and/or preventing stroke comprising administering the phenyl carbamate compound or a pharmaceutically acceptable salt thereof to a patient in need of stroke treatment; and a use of the phenyl carbamate compound or a pharmaceutically acceptable salt thereof in treating and/or preventing stroke, are provided.

5 Claims, 6 Drawing Sheets

(56) References Cited

FOREIGN PATENT DOCUMENTS

| WO | WO-2008/124848 A1 | 10/2008 |
| WO | WO-2012/002773 A2 | 1/2012 |
| WO | WO-2012/096458 A2 | 7/2012 |

OTHER PUBLICATIONS

International Application Serial No. PCT/KR2012/011471, International Search Report mailed Apr. 22, 2013, 4 pgs.
International Application Serial No. PCT/KR2012/011471, Written Opinion mailed Apr. 22, 2013, 5 pgs.
International Application Serial No. PCT/KR2012/011472, International Search Report mailed Apr. 23, 2013, 4 pgs.
International Application Serial No. PCT/KR2012/011472, Written Opinion mailed Apr. 23, 2013, 5 pgs.
International Application Serial No. PCT/KR2012/011474, International Search Report mailed Apr. 23, 2013, 4 pgs.
International Application Serial No. PCT/KR2012/011474, Written Opinion mailed Apr. 23, 2013, 5 pgs.
International Application Serial No. PCT/KR2012/011475, International Search Report mailed Apr. 23, 2013, 4 pgs.
International Application Serial No. PCT/KR2012/011475, Written Opinion mailed Apr. 23, 2013, 5 pgs.
Girijavallabhan, V. M., "Synthesis of the Antifungal Agent Sch 42427 (SM 9164)", *Bioorganic & Medicinal Chemistry Letters*, 1(7), (1991), 349-352.
Jiao, P., et al., "A Sequential O-Nitrosoaldol and Grignard Addition Process: An Enantio- and Diastereoselective Entry to Chiral 1,2-Diols", *Angewandte Chemie, International Edition*, 48(18), (2009), 3333-3336.
U.S. Appl. No. 13/727,654, Final Office Action mailed Jan. 29, 2014, 27 pgs.
U.S. Appl. No. 13/727,663, Non Final Office Action mailed Feb. 4, 2014, 9 pgs.
U.S. Appl. No. 13/727,654, Non Final Office Action mailed Sep. 9, 2014, 21 pgs.
U.S. Appl. No. 13/727,661, Restriction Requirement mailed Oct. 15, 2013, 6 pgs.
U.S. Appl. No. 13/727,663, Response filed Nov. 6, 2013 Restriction Requirement mailed Oct. 7, 2013, 6 pgs.
U.S. Appl. No. 13/727,663, Restriction Requirement mailed Oct. 7, 2013, 6 pgs.
"Epilepsy", by Mayo Clinic Staff, [online], Retrieved from the Internet: <URL: http://www.mayoclinic.com/health/epilepsy/DS00342/METHOD=print&DSECTION=all>, (2013), 14 pgs.
U.S. Appl. No. 13/727,663, Final Office Action mailed Oct. 23, 2014, 18 pgs.
U.S. Appl. No. 13/175,025, Final Office Action mailed Sep. 26, 2014, 8 pgs.
U.S. Appl. No. 13/175,025, Final Office Action mailed Oct. 10, 2013, 10 pgs.
U.S. Appl. No. 13/175,025, Non Final Office Action mailed Mar. 20, 2014, 9 pgs.
U.S. Appl. No. 13/175,025, Non Final Office Action mailed May 16, 2013, 19 pgs.
U.S. Appl. No. 13/175,025, Response filed Jan. 10, 2014 to Final Office Action mailed Oct. 10, 2013, 25 pgs.
U.S. Appl. No. 13/175,025, Response filed Aug. 16, 2013 to Non Final Office Action mailed May 16, 2013, 28 pgs.
U.S. Appl. No. 13/175,025, Response filed Aug. 20, 2014 to Non Final Office Action mailed Mar. 20, 2014, 25 pgs.
U.S. Appl. No. 13/175,025, Supplemental Amendment filed Sep. 13, 2013, 7 pgs.
U.S. Appl. No. 13/338,863, Non Final Office Action mailed Dec. 10, 2013, 6 pgs.
U.S. Appl. No. 13/338,863, Notice of Allowance mailed Apr. 29, 2014, 9 pgs.
U.S. Appl. No. 13/338,863, Response filed Mar. 6, 2014 to Non Final Ofifce Action mailed Dec. 10, 2013, 10 pgs.
U.S. Appl. No. 13/338,863, Response filed Oct. 28, 2013 to Restriction Requirement mailed Sep. 27, 2013, 9 pgs.
U.S. Appl. No. 13/338,863, Restriction Requirement mailed Sep. 27, 2013, 9 pgs.
U.S. Appl. No. 13/727,654, Examiner Interview Summary mailed May 29, 2014, 3 pgs.
U.S. Appl. No. 13/727,654, Response filed Jun. 27, 2014 to Final Office Action mailed Jan. 29, 2014, 21 pgs.
U.S. Appl. No. 13/727,659, Notice of Allowance mailed Sep. 23, 2014, 7 pgs.
U.S. Appl. No. 13/727,659, Response filed Aug. 22, 2014 to Non Final Office Action mailed Apr. 22, 2014, 37 pgs.
U.S. Appl. No. 13/727,661, Non Final Office Action mailed Jun. 24, 2014, 11 pgs.
U.S. Appl. No. 13/727,661, Preliminary Amendment filed Mar. 28, 2013, 4 pgs.
U.S. Appl. No. 13/727,661, Response filed Sep. 19, 2014 to Non Final Office Action mailed Jun. 24, 2014, 9 pgs.
U.S. Appl. No. 13/727,663, Non Final Office Action mailed Jul. 3, 2014, 17 pgs.
U.S. Appl. No. 13/727,663, Response filed May 1, 2014 to Non Final Office Action mailed Feb. 4, 2014, 46 pgs.
U.S. Appl. No. 13/727,663, Response filed Sep. 29, 2014 to Non Final Office Action mailed Jul. 3, 2014, 13 pgs.
Canadian Application Serial No. 2,815,460, Office Action mailed Mar. 6, 2014, 4 pgs.
Chinese Application Serial No. 201180032939.0, Office Action dated Mar. 31, 2014, (w/ English Translation), 8 pgs.
Chinese Application Serial No. 201180032939.0, Office Action dated Sep. 17, 2013, (w/ English Translation), 12 pgs.
Chinese Application Serial No. 201180063001.5, Office Action mailed Mar. 14, 2014, (w/ English Translation), 13 pgs.
European Application Serial No. 12169507.6, European Search Report maled Sep. 26, 2012, 8 pgs.
European Application Serial No. 12169507.6, Office Action mailed Feb. 21, 2014, 6 pgs.
European Application Serial No. 12169507.6, Office Action mailed Dec. 3, 2012, 2 pgs.
European Application Serial No. 12169507.6, Response filed May 17, 2013 to Office Action mailed Dec. 3, 2012, 14 pgs.
International Application Serial No. PCT/KR2011/004862, International Search Report mailed Feb. 27, 2012, 3 pgs.
International Application Serial No. PCT/KR2011/004862, Written Opinion mailed Feb. 27, 2012, 5 pgs.
International Application Serial No. PCT/KR2011/010105, International Search Report mailed Aug. 7, 2012, 3 pgs.
International Application Serial No. PCT/KR2011/010105, Written Opinion mailed Aug. 7, 2012, 4 pgs.
Japanese Application Serial No. 2013-518264, Office Action mailed Mar. 11, 2014, (w/ English Translation), 6 pgs.
Amarante, G. W., et al., "Acyloins from Morita-Baylis-Hillman adducts: an alternative approach to the racemic total synthesis of bupropion", *Tettrahedron Letters*, 49, (2008), 3744-3748.
Bausch, C. C. et al., "Cross Silyl Benzoin Additions Catalyzed by Lanthanum Tricyanide", *J. Org.Chem.*, 69, (2004), 4283-4285.
Cannon, J. G., "Chapter Nineteen—Analog Design", In: *Burger's Medicinal Chemistry and Drug Discovery*, Fifth Edition, vol. I: Principles and Practice, Wiley-Interscience, (1995), 783-802.
Citterio, A., et al., "Electron-transfer Processes: Oxidation of a-and β-Alkenylbenzenes by Peroxydisulphate in Acetic Acid", *J. Chem. Soc. Perkin Tran.* I, (1983), 891-896.
Edin, Michaela, et al., "Ruthenium- and lipase-catalyzed DYKAT of 1,2-diols: an enantioselective synthesis of syn-1,2-diacetates", *Tetrahedron: Asymmetry.* 17(4), (2006), 708-715.
Eid, Jr., C. N., et al., "Enantiomerically Pure Ketals in Synthesis, Diastereoselective Formation of β-Keto and β-Hydroxy Ketals", *Tetrahedron Letters*, 32(4), (1991), 461-464.
Ghosh, N., et al., "Gold-Catalyzed Regioselective Hydration of Propargyl Acetates Assisted by a Neighboring Carbonyl Group: Access to a-Acyloxy Methyl Ketones and Synthesis of (±)-Actinopolymorphol B", *J. Org. Chem.*, (2010), 500-511.
Girijavallabhan, V. M., et al., "Synthesis of the antifungal agent SCH 42427 (SM 9164)", (Abstract), *Bioorganic & Medicinal Chemistry Letters*, 1(7), 349-352, ASC on STN, Accession No. 1992:41371, (1991), 1 pg.

(56) References Cited

OTHER PUBLICATIONS

Joseph, S. P., et al., "Reaction of chlorosulfonyl isocyanate with 1,2-diols", *Synthetic Communications*. 18(18), (1988), 2295-2302.

Morimoto, Takashi, et al., "Oxidation by cobalt(III) acetate, Part 10. Effects of ring substituents on the product distributions in the oxidation of β-methylstyrenes by cobalt(III) acetate in acetic acid", *J. Chem, Soc. Perkin Trans. II*, (1986), 1205-1209.

Ohta, Hiromichi, et al., "Reductive $C_2$-Homologation of Substituted Benzaldehydes by Fermenting Baker's Yeast", *Agric. Biol. Chem.*, 50(5), (1986), 1261-1266.

Sheridan, R. P., "The Most Common Chemical Replacements in Drug-Like Compounds", *J. Chem, Inf. Comupt. Sci.*, vol. 42, (2002), 103-108.

Wijesekera, L. C., et al., "Amyotrophic lateral sclerosis", *Orphanet Journal of Rare Diseases*, 4:3, (2009), 1-22.

U.S. Appl. No. 13/727,654, Response filed Dec. 9, 2013 to Non Final Office Action mailed Sep. 9, 2013, 17 pgs.

U.S. Appl. No. 13/727,661, Response filed Nov. 15, 2013 to Restriction Requirement mailed Oct. 15, 2013, 6 pgs.

Lehmkuhle, M. J, et al., "A Simple Quantitative Method for Analyzing Electrographic Status Epilepticus in Rats", *J Neurophysiol.*, 101, (Mar. 2009), 1660-1670.

**Measurement of Infarction area
(Cerebral cortex and Striatum)**

Measurement fo Infarction area
(Cerebral cortex and Striatum)

A : Day 1 control (occlusion for 1 day), vehicle (30% PEG400), i.p., b.i.d. (1st inj : 1 hr after occlusion, 8 hr interval), n=9
B : Day 3 Treatment (occlusion for 3 days), Compound 1, 60 mg/kg, i.p., b.i.d. (1st inj.: 1 hr after occlusion, 8 hr interval), n=6

Measurement of infarction area
(Cerebral cortex and Striatum)

PHENYL CARBAMATE COMPOUNDS FOR USE IN PREVENTING OR TREATING STROKE

CROSS-REFERENCE TO RELATED APPLICATION

This application claims priority to and the benefit of U.S. Provisional Application No. 61/580,409 filed in the United States Patent and Trademark Office on Dec. 27, 2011, the entire contents of which are incorporated herein by reference.

TECHNICAL FIELD

A phenyl carbamate compound; a composition for treating and/or preventing stroke containing the phenyl carbamate compound or a pharmaceutically acceptable salt thereof as an active ingredient; a method of treating and/or preventing stroke comprising administering the phenyl carbamate compound or a pharmaceutically acceptable salt thereof to a patient in need of stroke treatment; and a use of the phenyl carbamate compound or a pharmaceutically acceptable salt thereof in treating and/or preventing stroke, are provided.

BACKGROUND ART

Approximately 15 million people worldwide suffer a stroke each year, resulting in death or sensorimotor and other defects. Stroke remains the third most common cause of death in the industrialized world behind heart disease and cancer. There are two kinds of stroke: one is ischemic stroke, caused by a blood clot that blocks or prevents the flow of blood, and the other is hemorrhagic stroke, caused by bleeding into or around the brain.

Ischemic stroke is responsible for about one third of all deaths in industrialized countries and is the major cause of serious, long-term disability in adults over the age of 45. It stands to reason that there is a need for pharmacotherapy to treat acute ischemic stroke. Considerable insights have been gained into the mechanisms of stroke and the cascade of events that occurs following stroke; there is also an improved understanding of neuronal injury and cell death.

The three main mechanisms of ischemic stroke are thrombosis, embolism, and systemic hypoperfusion (with resultant ischemia and hypoxia). In each of these types of stroke, the area of the brain that dies as a result of the lack of blood supply thereto is called an infarct. Obstruction of a cerebral artery resulting from a thrombus that has built up on the wall of a brain artery is generally called "cerebral thrombosis." In cerebral embolism, the occlusive material blocking the cerebral artery arises downstream in the circulation (e.g., an embolus is carried to the cerebral artery from the heart). Because it is difficult to discern whether a stroke is caused by thrombosis or embolism, the term "thromboembolism" is used to cover both these types of stroke. Systemic hypoperfusion may arise as a consequence of elevated blood lactate levels, reduced hematocrit, low blood pressure, or inability of the heart to pump blood adequately.

Also, the excessive or inappropriate stimulation of excitatory amino acid receptors leads to neuronal cell damage or loss by the way of a mechanism known as excitotoxicity. So, Excitatory amino acid excitotoxicity has been implicated in the pathophysiology of a number of neurological disorders. Such as stoke, cerebral ischemia and spinal cord trauma etc.

When symptoms of stroke last less than 24 hours and the patient recovers completely, the patient is said to have undergone a transient ischemic attack (TIA). The symptoms of TIA are a temporary impairment of speech, vision, sensation, or movement. Because a TIA is often thought to be a prelude to full-scale stroke, patients having suffered a TIA are candidates for prophylactic stroke therapy with anticoagulation agents (e.g., coumarin, and heparin) or anti-platelet agents (such as aspirin and ticlopidine), for example. But, in approximately 20% to 40% of patients with stroke, the underlying etiology is not established (called "cryptogenic," "uncertain," or "undetermined" stroke).

Therefore, a need exists for a therapy that is effective in the treatment all types of stroke, i.e., both ischemic strokes and hemorrhagic strokes.

SUMMARY OF THE INVENTION

An embodiment provides an organic compound, i.e., phenyl carbamate compound. More particularly, the embodiment is directed to a phenyl carbamate compound of the following Chemical Formula 1; a racemate, an enantiomer, a diastereomer, a mixture of enantiomers, or a mixture of diastereomers thereof; or a pharmaceutically acceptable salt thereof. The compound has remarkably excellent treatment and/or prevention effect on stroke as well as very low toxicity. Therefore, the compounds of formula I may be useful as a drug for the treatment and/or prevention of stroke:

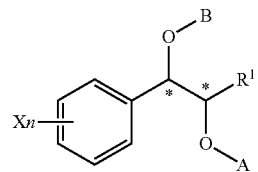

[Chemical Formula 1]

wherein,

X is a halogen, for example, chlorine, fluorine, iodine, or bromine, n, that means the number of substituent X, is an integer from 1 to 5, for example, 1 or 2, R1 is a linear or branched alkyl group of C1-C4, for example, methyl group, ethyl group, isopropyl group, or butyl group, A is hydrogen or a carbamoyl derivative represented by

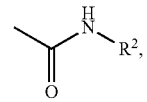

B is hydrogen, a carbamoyl derivative represented by

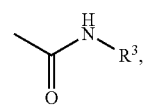

trialkyl silyl groups (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), or a trialkyl silyl ether group, wherein each alkyl group may be independently selected from the group consisting of linear, branched, or cyclic C1-C4 alkyl groups, and each aryl group may be independently selected from the group consisting of C5-C8 aryl groups, preferably a phenyl group, A and B are not carbamoyl derivatives at same time, and R2 and R3 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R2 and R3 may be the same as or different from each other, and independently selected from the group consisting of hydrogen, methyl group, propyl group, isopropyl group, cyclopropyl group, cyclohexyl group, bicycloheptane group, and benzyl group.

Another embodiment provides a pharmaceutical composition for of preventing and/or treating stroke containing a compound of Chemical Formula 1; a racemate, an enantiomer, a diastereomer, a mixture of enantiomers, or a mixture of diastereomers thereof; or a pharmaceutically acceptable salt thereof, as an active ingredient Another embodiment provides a method of preventing and/or treating stroke comprising administering a therapeutically effective amount of a phenyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of preventing and/or treating stroke.

Another embodiment provides a use of a phenyl carbamate compound represented by Chemical Formula 1; a racemate, an enantiomer, a diastereomer, a mixture of enantiomers, or a mixture of diastereomers thereof; or a pharmaceutically acceptable salt thereof, in the prevention and/or treatment of stroke, or in the manufacture of a pharmaceutical composition for preventing and/or treating stroke.

DETAILED DESCRIPTION OF THE EMBODIMENTS

Continuing its research work in the field of stroke, the present inventors, as results of studies on the development of anti-stroke drugs, found that a phenyl carbamate compounds of the following Chemical Formula 1 exhibits remarkably excellent anti-stroke activity in various emulation models and simultaneously has very low toxicity, to complete the invention.

An embodiment provides an organic compound, particularly, a phenyl carbamate compound, more particularly, a phenyl carbamate compound represented by following Chemical Formula 1; a racemate, an enantiomer, a diastereomer, a mixture of enantiomers, or a mixture of diastereomers thereof; or a pharmaceutically acceptable salt thereof:

[Chemical Formula 1]

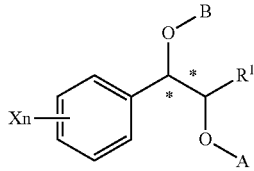

wherein,

X is a halogen, for example, chlorine, fluorine, iodine, or bromine, n, that means the number of substituent X, is an integer from 1 to 5, for example, 1 or 2, R1 is a linear or branched alkyl group of C1-C4, for example, methyl group, ethyl group, isopropyl group, or butyl group, A is hydrogen or a carbamoyl derivative represented by

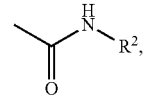

B is hydrogen, a carbamoyl derivative represented by

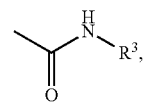

trialkyl silyl groups (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), or a trialkyl silyl ether group, wherein each alkyl group may be independently selected from the group consisting of linear, branched, or cyclic C1-C4 alkyl groups, and each aryl group may be independently selected from the group consisting of C5-C8 aryl groups, preferably a phenyl group, A and B are not carbamoyl derivatives at same time, and R2 and R3 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R2 and R3 may be the same as or different from each other, and independently selected from the group consisting of hydrogen, methyl group, propyl group, isopropyl group, cyclopropyl group, cyclohexyl group, bicycloheptane group, and benzyl group.

In concrete embodiment, the phenyl carbamate compound may be selected from the group consisting of:

1-(2-chlorophenyl)-1-hydroxypropyl-2-carbamate,
1-(2-chlorophenyl)-1-hydroxybutyl-2-carbamate,
1-(2-chlorophenyl)-1-hydroxy-3-methyl-butyl-2-carbamate,
1-(2-chlorophenyl)-1-hydroxyhexyl-2-carbamate,
1-(2-chlorophenyl)-1-hydroxypropyl-2-N-methylcarbamate,
1-(2-chlorophenyl)-1-hydroxypropyl-2-N-propylcarbamate,
1-(2-chlorophenyl)-1-hydroxypropyl-2-N-isopropylcarbamate,
1-(2-chlorophenyl)-1-hydroxypropyl-2-N-cyclopropylcarbamate,
1-(2-chlorophenyl)-1-hydroxypropyl-2-N-cyclohexylcarbamate,
1-(2-chlorophenyl)-1-hydroxypropyl-2-N-benzylcarbamate,
1-(2-chlorophenyl)-1-hydroxypropyl-2-N-bicyclo[2,2,1]heptanecarbamate,
1-(2,4-dichlorophenyl)-1-hydroxypropyl-2-carbamate,
1-(2,6-dichlorophenyl)-1-hydroxypropyl-2-carbamate,
1-(2,4-dichlorophenyl)-1-hydroxybutyl-2-carbamate,
1-(2,6-dichlorophenyl)-1-hydroxybutyl-2-carbamate, 1-(2,4-dichlorophenyl)-1-hydroxy-3-methyl-butyl-2-carbamate,
1-(2,6-dichlorophenyl)-1-hydroxy-3-methyl-butyl-2-carbamate,
1-(2,4-dichlorophenyl)-1-hydroxyhexyl-2-carbamate,
1-(2,6-dichlorophenyl)-1-hydroxyhexyl-2-carbamate,
1-(2-chlorophenyl)-2-hydroxypropyl-1-carbamate,
1-(2-chlorophenyl)-2-hydroxypropyl-1-N-methylcarbamate,
1-(2-chlorophenyl)-2-hydroxypropyl-1-N-propylcarbamate,
1-(2-chlorophenyl)-2-hydroxypropyl-1-N-isopropylcarbamate,
1-(2-chlorophenyl)-2-hydroxypropyl-1-N-cyclopropylcarbamate,
1-(2-chlorophenyl)-2-hydroxypropyl-1-N-cyclohexylcarbamate,
1-(2-chlorophenyl)-2-hydroxypropyl-1-N-benzylcarbamate,
1-(2,4-dichlorophenyl)-2-hydroxypropyl-1-carbamate,
1-(2,6-dichlorophenyl)-2-hydroxypropyl-1-carbamate,
1-(2,4-dichlorophenyl)-2-hydroxybutyl-1-carbamate,
1-(2,6-dichlorophenyl)-2-hydroxybutyl-1-carbamate,
1-(2,4-dichlorophenyl)-2-hydroxy-3-methyl-butyl-1-carbamate,
1-(2,6-dichlorophenyl)-2-hydroxy-3-methyl-butyl-1-carbamate,
1-(2,4-dichlorophenyl)-2-hydroxyhexyl-1-carbamate,
1-(2,6-dichlorophenyl)-2-hydroxyhexyl-1-carbamate,
1-(2-fluorophenyl)-1-hydroxypropyl-2-carbamate,
1-(2-iodophenyl)-1-hydroxypropyl-2-carbamate,
1-(2-iodophenyl)-1-hydroxybutyl-2-carbamate,
1-(2,3-dichlorophenyl)-1-hydroxypropyl-2-carbamate, and
1-(2,3-dichlorophenyl)-2-hydroxypropyl-1-carbamate.

In this compound, 2 chiral carbons exist at positions 1 and 2 from phenyl group substituted with X; thus, the compound may exist in the form of an enantiomer, a diastereomer, a mixture of enantiomers, or a mixture of diastereomers, as well as a racemate.

Alternatively, the compound may be in the form of a pharmaceutically acceptable salt. The pharmaceutically acceptable salt may include an additional salt of acid or base, and its stereochemical isomer. For example, the compound may be in the form of an additional salt of an organic or inorganic acid. The salt may not be specially limited, and include any salts that maintain the activities of their parent compounds, with no undesirable effects, in the subject, when they are administered to the subject. Such salts may include inorganic and organic salts, such as salts of acetic acid, nitric acid, aspartic acid, sulfonic acid, sulfuric acid, maleic acid, glutamic acid, formic acid, succinic acid, phosphoric acid, phthalic acid, tannic acid, tartaric acid, hydrobromic acid, propionic acid, benzene sulfonic acid, benzoic acid, stearic acid, lactic acid, bicarbonic acid, bisulfuric acid, bitartaric acid, oxalic acid, butyric acid, calcium edetate, carbonic acid, chlorobezoic acid, citric acid, edetic acid, toluenesulfonic acid, fumaric acid, gluceptic acid, esilic acid, pamoic acid, gluconic acid, methyl nitric acid, malonic acid, hydrochloric acid, hydroiodic, hydroxynaphtholic acid, isethionic acid, lactobionic acid, mandelic acid, mucic acid, naphthylic acid, muconic acid, p-nitromethanesulfonic acid, hexamic acid, pantothenic acid, monohydrogen phosphoric acid, dihydrogen phosphoric acid, salicylic acid, sulfamic acid, sulfanilic acid, methane sulfonic acid, and the like. The additional salts of base may include salts of akali metal or alkaline earth metal, such as salts of ammonium, lithium, sodium, potassium, magnesium, calcium, and the like; salts having an organic base, such as benzathine, N-methyl-D-glucamine, hydrabamine, and the like; and salts having an amino acid such as arginine, lysine, and the like. In addition, these salts may be converted to a released form by treating with a proper base or acid.

As demonstrated in the following experimental examples, the compound of Chemical Formula 1, a racemate, an enantiomer, a diastereomer, a mixture of enantiomers, or a mixture of diastereomers thereof, or pharmaceutically acceptable salt thereof exhibits an excellent effect on preventing and/or treating stroke. Therefore, another embodiment provides a pharmaceutical composition for preventing and/or treating stroke containing a phenyl carbamate compound represented by Chemical Formula 1; a racemate, an enantiomer, a diastereomer, a mixture of enantiomers, or a mixture of diastereomers thereof; or a pharmaceutically acceptable salt thereof, as an active ingredient.

Another embodiment provides a method of preventing and/or treating stroke comprising administering a therapeutically effective amount of a phenyl alkyl carbamate compound represented by Chemical Formula 1; a racemate, an enantiomer, a diastereomer, a mixture of enantiomers, or a mixture of diastereomers thereof; or a pharmaceutically acceptable salt thereof, to a subject in need of preventing and/or treating stroke. The method may further comprise a step of identifying the subject in need of preventing and/or treating stroke prior to the step of administering. The term "therapeutically effective amount" may refer to an amount of the active gradient capable of exhibiting the effect of preventing and/or treating stroke.

Another embodiment provides a phenyl carbamate compound represented by Chemical Formula 1, a racemate, an enantiomer, a diastereomer, a mixture of enantiomers, or a mixture of diastereomers thereof, or a pharmaceutically acceptable salt thereof, for use in the prevention and/or treatment of stroke or in the manufacture of a medicament for preventing and/or treating stroke.

Another embodiment provides a use of a phenyl carbamate compound represented by Chemical Formula 1, a racemate, an enantiomer, a diastereomer, a mixture of enantiomers, or a mixture of diastereomers thereof, or a pharmaceutically acceptable salt thereof, in the prevention and/or treatment of stroke or in the manufacture of a medicament for preventing and/or treating stroke.

The stroke to be treated and/or prevented may include an ischemic stroke (for example, acute ischemic stroke, and the like) and/or a hemorrhagic stroke. In a concrete embodiment, the stroke may include a neurodegeneration associated stroke, and may not be a muscle spasm associated stroke.

The pharmaceutical composition may be formulated in various forms for oral or parenteral administration. For example, the pharmaceutical composition may be formulated in the oral administration form, such as a tablet, pill, soft or hard capsule, liquid, suspension, emulsion, syrup, granules, elixirs, and the like. In addition to the active ingredient, the oral administration form may further include pharmaceutically acceptable and conventional components, for example, a diluent such as lactose, dextrose, sucrose, mannitol, sorbitol, cellulose, glycine, and the like; a lubricant such as silica, talc, stearic acid, magnesium or calcium salt thereof, polyethyleneglycol, and the like.

In the case that the oral administration form is a tablet, it may further include a binder such as magnesium aluminium silicate, starch paste, gelatin, tragacanth, methylcellulose, sodium carboxymethylcellulose, polyvinylpirrolidine, and the like; and optionally include one or more additives selected from the group consisting of a disintegrant such as starch, agar, arginic acid or sodium salt thereof, an absorbent, a colorant, a flavoring, a sweetener, and the like.

Alternatively, the pharmaceutical composition may also be formulated in a parenteral administration form, which can be administered by subcutaneous injection, intravenous injection, intramuscular injection, injection into thoracic cavity, and the like. In order to formulate the parenteral administration form, the pharmaceutical composition may be prepared as a solution or suspension wherein the active ingredient is dissolved in water together with a stabilizer and/or a buffering agent, and such solution or suspension formulation may be prepared as a dosage form in ample or vial.

The pharmaceutical composition may be sterilized, and/or include further additives such as a preservative, a stabilizer, a hydrating agent, an emulsification accelerator, a salt and/or buffering agent for osmoregulation, and the like, and/or further therapeutically effective ingredients. The pharmaceutical composition may be formulated by any conventional method for mixing, granulating, coating, and the like.

The pharmaceutical composition may be administered to a mammal including human, in the therapeutically effective amount of 0.01 to 750 mg/kg (body weight), preferably 0.1 to 500 mg/kg (body weight) per one day, based on the active ingredient. The pharmaceutically effective amount may refers to an amount capable of exhibiting a desired effect, i.e., an effect of treating and/or preventing multiple sclerosis. The pharmaceutically effective amount may be administered through oral or parenteral pathway (e.g., an intravenous injection, an intramusclular injection, etc.), one or two or more times per one day.

The therapeutically effective amount and the administration pathway of the present pharmaceutical composition may be properly adjusted by a person skilled in the relevant field considering the conditions of the subject (patient), desired effects, and the like.

The subject may be a mammal including human or cells and/or tissues separated therefrom.

The phenyl carbamate compound of the present invention may prepared by the following reaction formula.

Reaction Formula I: Synthesis of Diol-1

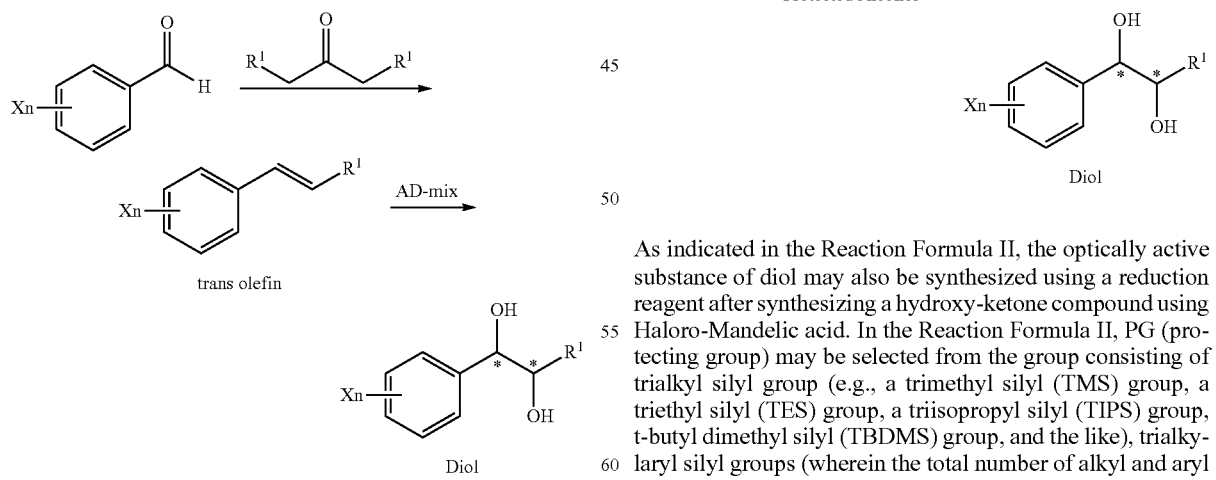

A diol compound used in the synthesis of the carbamate compound may be synthesized by dihydroxylation of a trans-olefin compound. A diol compound having optical activity may be synthesized using a sharpless asymmetric dihydroxylation catalyst.

Reaction Formula II: Synthesis of Diol-2

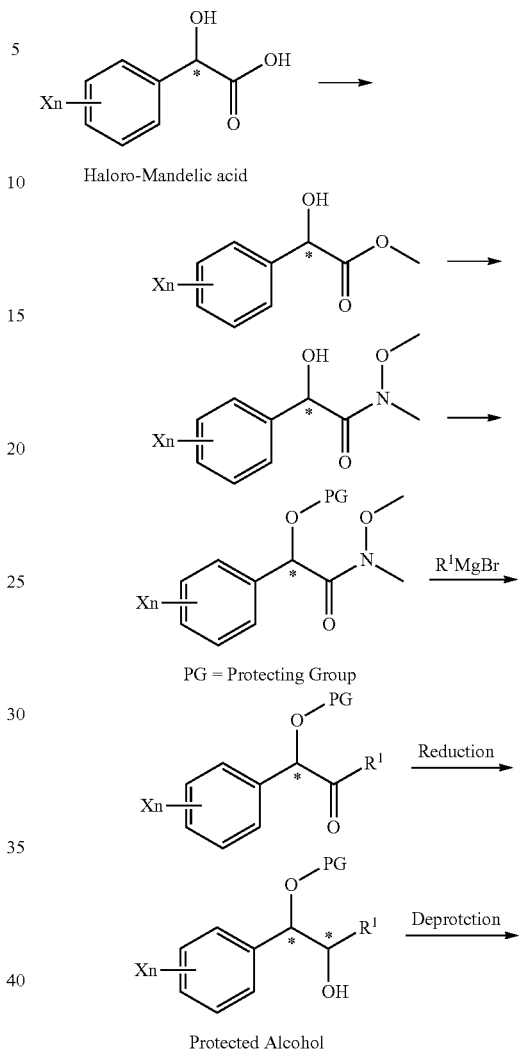

As indicated in the Reaction Formula II, the optically active substance of diol may also be synthesized using a reduction reagent after synthesizing a hydroxy-ketone compound using Haloro-Mandelic acid. In the Reaction Formula II, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group[Ac (acetate), Bz (benzoate), Pv (pivaloate), Cbz (benzyl carbonate), BOC (t-butyl carbonate), Fmoc (9-fluoroenylmethyl)carbaonate, Alloc (allyl Carbonate), Troc (trichloroethyl carbonate), p-methoxybenzoate, methyl carbonate, and so on] and the like, wherein each alkyl group may be independently selected from the group consisting of linear, branched, or cyclic C1-C4 alkyl groups, and each aryl group may be independently selected from the group consisting of C5-C8 aryl groups, preferably a phenyl group.

Reaction Formula III: Carbamation Reaction-1

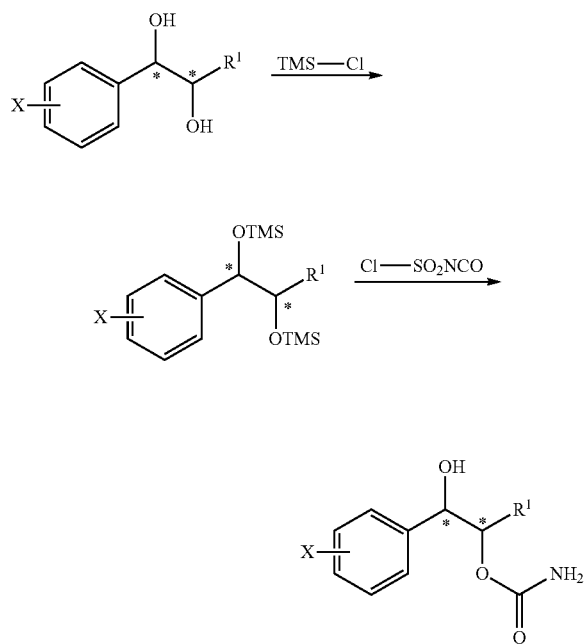

As a highly selectivity form of regioisomer of single carbamate of diol having halogen substituent at phenyl ring. (Example 1~14 and 36~67 are synthesized by reaction formula III)

Reaction Formula IV: Carbamation Reaction-2

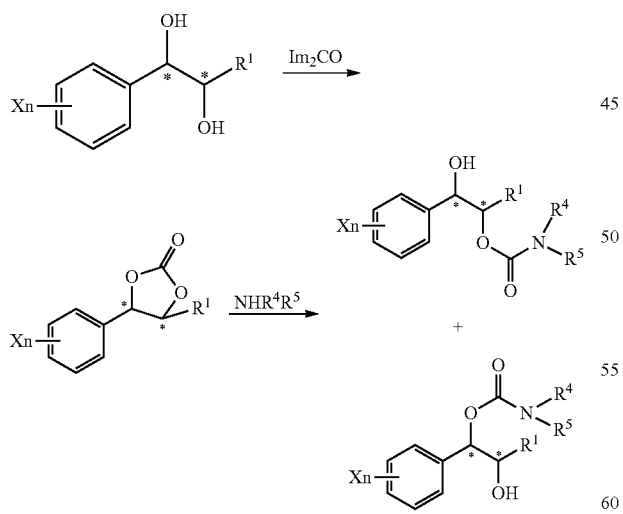

Two substances in the form of regioisomers of a single carbamate of diol having halogen substituent at phenyl ring may be separated by flash column chromatography to obtain two kinds of single carbamate compounds. (Example 15~35 and 68~115 are synthesized by reaction formula IV)

Reaction Formula V: Protection Reaction

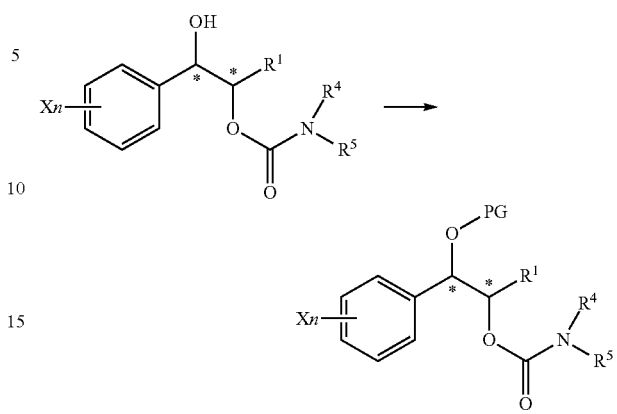

In the Reaction Formula V, PG (protecting group) may be selected from the group consisting of trialkyl silyl group (e.g., a trimethyl silyl (TMS) group, a triethyl silyl (TES) group, a triisopropyl silyl (TIPS) group, t-butyl dimethyl silyl (TBDMS) group, and the like), trialkylaryl silyl groups (wherein the total number of alkyl and aryl groups is three; e.g., a t-butyl diphenyl silyl (TBDPS) group and the like), ester group[Ac (acetate), Bz (benzoate), Pv (pivaloate), Cbz (benzyl carbonate), BOC (t-butyl carbonate), Fmoc (9-fluoroenylmethyl)carbaonate, Alloc (allyl Carbonate), Troc (trichloroethyl carbonate), p-methoxybenzoate, methyl carbonate, and so on] and the like, wherein each alkyl group may be independently selected from the group consisting of linear, branched, or cyclic C1-C4 alkyl groups, and each aryl group may be independently selected from the group consisting of C5-C8 aryl groups, preferably a phenyl group.

In the Reaction Formula IV and V, R4 and R5 may be the same as or different from each other, and independently selected from the group consisting of hydrogen, a linear or branched alkyl group of C1-C4, for example C1-C3, a cycloalkyl group of C3-C8, for example C3-C7, and benzyl group, and more specifically, R4 and R5 may be the same as or different from each other, and independently selected from the group consisting of hydrogen, methyl group, propyl group, isopropyl group, cyclopropyl group, cyclohexyl group, bicycloheptane group, and benzyl group.

Two substances in the form of regioisomers of a single carbamate of diol having halogen substituent at phenyl ring may be separated by flash column chromatography to obtain two kinds of single carbamate compounds.

EXAMPLE

Figure 1:
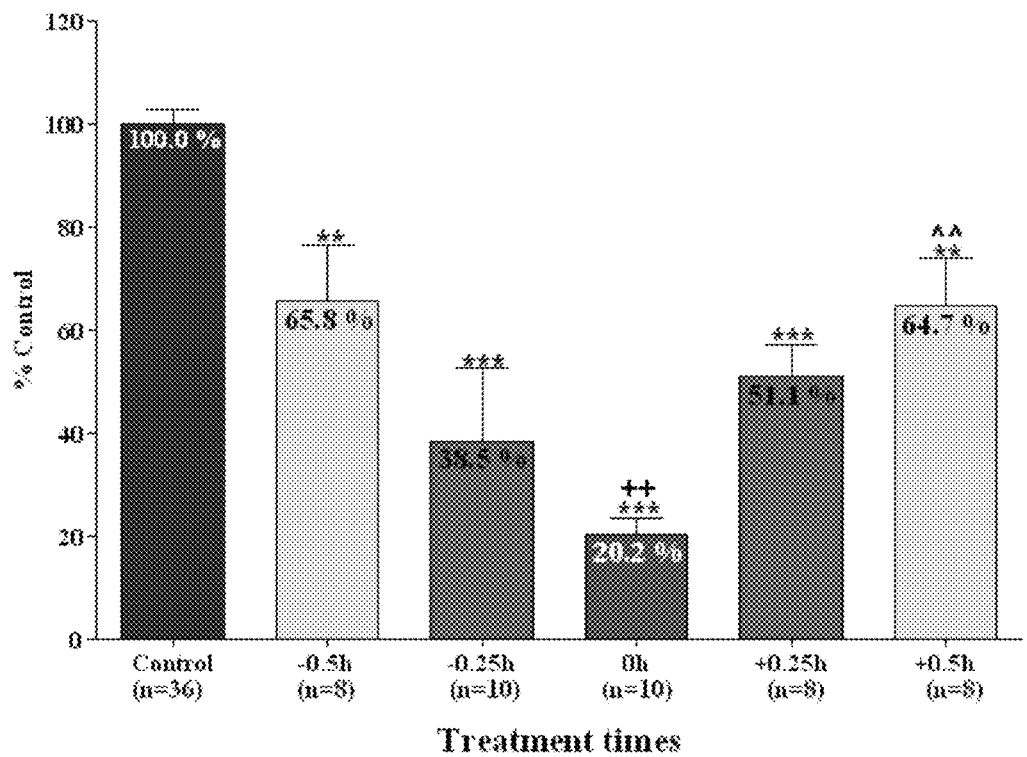
FIG. 1 shows the 2,3,5-triphenyltetrazolium chloride (TTC)-stained infarction area (% control) with treatment the compound example 1 on tMCAO (Transient Middle Cerebral Artery Occlusion) at various time points.

The present invention is further explained in more detail with reference to the following examples. These examples, however, should not be interpreted as limiting the scope of the present invention in any manner.

Preparation Example 1

Synthesis of 1-(2-chlorophenyl)-trans-1-propene

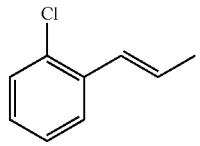

48 ml of 2-chlorobenzenaldehyde (0.42 mol) and 49.7 ml of 3-pentanone (0.47 mol) were dissolved in 600 mL of hexane in flask, and then stirred with raising the temperature. 53.6 ml of Boron trifluoride etherate ($BF_3OEt_2$, 0.42 mol) was added to the resultant under reflux conditions. When the reaction was completed, water was added thereto. After layer separation, the obtained organic layer was washed twice with 1M sodium hydroxide solution (1M NaOH), and then the separated organic layer was washed with water. The separated organic layer was dehydrated with anhydrous magnesium sulfate ($MgSO_4$) and concentrated. The concentrated residue was purified by a silica gel column chromatography to produce the title compound (38 g, yield 58%).

$^1$H NMR(400 MHz, $CDCl_3$) δ1.94(d, J=4.8 Hz, 3H), 6.24 (m, 1H), 6.78(d, J=14 Hz, 1H), 7.11~7.51(m, 4H)

Preparation Example 2

Synthesis of 1-(2-chlorophenyl)-trans-1-butene

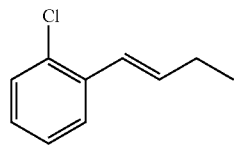

The substantially same method as described in Preparation Example 1 was conducted, except that 3-heptanone was used instead of 3-pentanone, to obtain the title compound (2.9 g, yield 83%).

$^1$H NMR(400 MHz, $CDCl_3$) δ1.14(d, J=7.6 Hz, 3H), 2.29~2.33(m, 2H), 6.28(dt, J=16 Hz, 6.4 Hz, 1H), 6.78(d, J=15.6 Hz, 1H), 7.13~7.54(m, 4H)

Preparation Example 3

Synthesis of 1-(2-chlorophenyl)-3-methyl-trans-1-butene

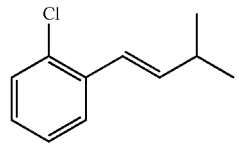

The substantially same method as described in Preparation Example 1 was conducted, except that 2,6-dimethyl-heptan-4-one was used instead of 3-pentanone, to obtain the title compound (8.0 g, yield 50~90%).

$^1$H NMR(400 MHz, $CDCl_3$) δ1.14(d, J=6.8 Hz, 6H), 2.25~2.57(m, 1H), 6.20(dd, J=16 Hz, 7.2 Hz, 1H), 7.64(d, J=16 Hz, 1H), 7.12~7.54(m, 4H)

Preparation Example 4

Synthesis of 1-(2-chlorophenyl)-trans-1-hexene

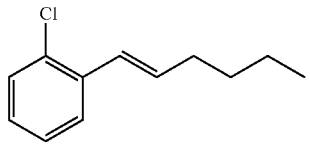

The substantially same method as described in Preparation Example 1 was conducted, except that 6-undecanone was used instead of 3-pentanone, to obtain the title compound (10 g, yield 85%).

$^1$H NMR(400 MHz, $CDCl_3$) δ0.96(1, J=7.2 Hz, 3H), 1.33~1.56(m, 4H), 2.26~2.32(m, 4H), 6.24(dt, J=15.6 Hz, 7 Hz, 1H), 6.78(d, J=16 Hz, 1H), 7.13~7.54(m, 4H)

Preparation Example 5

Synthesis of 1-(2,4-dichlorophenyl)-trans-1-propene

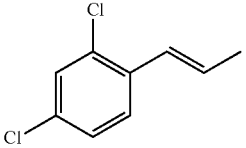

The substantially same method as described in Preparation Example 1 was conducted, except that 2,4-dichlorobenzenaldehyde was used instead of 2-chlorobenzenaldehyde, to obtain the title compound (2.4 g, yield 57%).

$^1$H NMR(400 MHz, CDCl$_3$) δ1.95(dd, J=6.8 Hz, 1.6 Hz, 3H), 6.24(m, 1H), 6.72(d, J=15.6 Hz, 1H), 7.18~7.44(m, 3H)

Preparation Example 6

Synthesis of 1-(2,4-dichlorophenyl)-trans-1-butene

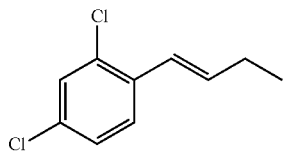

The substantially same method as described in Preparation Example 5 was conducted, except that 3-heptanone was used instead of 3-pentanone, to obtain the title compound (2.1 g, yield 90%).

$^1$H NMR(400 MHz, CDCl$_3$) δ1.14(d, J=7.6 Hz, 3H), 2.20~2.33(m, 2H), 6.26(dt, J=16 Hz, 6.8 Hz, 1H), 6.70(d, J=15.6 Hz, 1H), 7.18~7.46(m, 3H)

Preparation Example 7

Synthesis of 1-(2,6-dichlorophenyl)-3-methyl-trans-1-butene

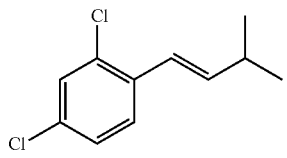

The substantially same method as described in Preparation Example 5 was conducted, except that 2,6-dimethyl-heptan-4-one was used instead of 3-pentanone, to obtain the title compound (0.23 g, yield 10~40%).

$^1$H NMR(400 MHz, CDCl$_3$) δ1.15(d, J=6.8 Hz, 6H), 2.53~2.58(m, 1H), 6.19(dd, J=16.4 Hz, 6.8 Hz, 1H), 6.31(d, J=16.4 Hz, 1H), 7.18~7.46(m, 3H)

Preparation Example 8

Synthesis of 1-(2,4-dichlorophenyl)-trans-1-hexene

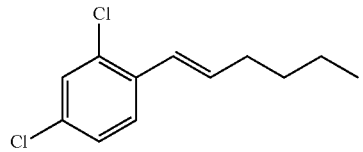

The substantially same method as described in Preparation Example 5 was conducted, except that 6-undecanone was used instead of 3-pentanone, to obtain the title compound (3.2 g, yield 40~80%).

$^1$H NMR(400 MHz, CDCl$_3$) δ0.96(t, J=7.2 Hz, 3H), 1.38~1.52(m, 4H), 2.25~2.31(m, 2H), 6.22(dt, J=15.6 Hz, 6.8 Hz, 1H), 6.70(d, J=15.6 Hz, 1H), 7.18~7.46(m, 3H)

Preparation Example 9

Synthesis of 1-(2,6-dichlorophenyl)-trans-1-propene

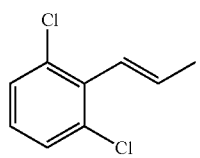

The substantially same method as described in Preparation Example 1 was conducted, except that 2,6-dichlorobenzenaldehyde was used instead of 2-chlorobenzenaldehyde, to obtain the title compound (0.4 g, yield 10~40%).

$^1$H NMR(400 MHz, CDCl$_3$) δ1.98(d, J=8 Hz, 3H), 6.23~6.31(m, 1H), 6.40(d, J=16 Hz, 1H), 7.05~7.32(m, 3H)

Preparation Example 10

Synthesis of 1-(2,6-dichlorophenyl)-trans-1-butene

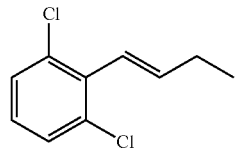

The substantially same method as described in Preparation Example 9 was conducted, except that 3-heptanone was used instead of 3-pentanone, to obtain the title compound (1.2 g, yield 10~40%).

$^1$H NMR(400 MHz, CDCl$_3$) δ1.17(t, J=7.6 Hz, 3H), 2.30~2.37(m, 2H), 6.29(dt, J=16.4 Hz, 6 Hz, 1H), 6.37(d, J=16.4 Hz, 1H), 7.05~7.32(m, 3H)

Preparation Example 11

Synthesis of 1-(2,6-dichlorophenyl)-3-methyl-trans-1-butene

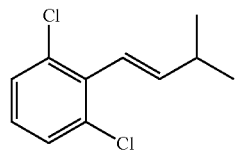

The substantially same method as described in Preparation Example 9 was conducted, except that 2,6-dimethyl-heptan-4-one was used instead of 3-pentanone, to obtain the title compound (0.23 g, yield 10~40%).

¹H NMR(400 MHz, CDCl₃) δ1.15(d, J=6.8 Hz, 6H), 2.53~2.58(m, 1H), 6.19(dd, J=16.4 Hz, 6.8 Hz, 1H), 6.31(d, J=16.4 Hz, 1H), 7.05~7.32(m, 3H)

Preparation Example 12

Synthesis of 1-(2,6-dichlorophenyl)-trans-1-hexene

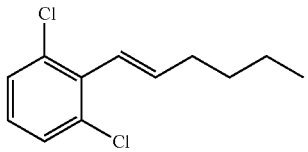

The substantially same method as described in Preparation Example 9 was conducted, except that 6-undecanone was used instead of 3-pentanone, to obtain the title compound (0.2 g, yield 10~40%).

¹H NMR(400 MHz, CDCl₃) δ0.99(t, J=7.2 Hz, 3H), 1.14~1.59(m, 4H), 2.30~2.36(m, 2H), 6.24(dt, J=16 Hz, 6.6 Hz, 1H), 6.38(d, J=16.4 Hz, 1H), 7.05~7.33(m, 3H)

Preparation Example 13

Synthesis of 1-(2,3-dichlorophenyl)-trans-1-propene

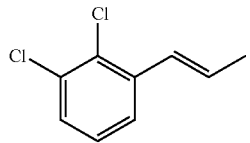

The substantially same method as described in Preparation Example 1 was conducted, except that 2,3-dichlorobenzenaldehyde was used instead of 2-chlorobenzenaldehyde, to obtain the title compound (0.2 g, yield 10~40%).

¹H NMR(400 MHz, CDCl₃) δ1.94(d, J=4.8 Hz, 3H), 6.24 (m, 1H), 6.78(d, J=14 Hz, 1H), 7.11~7.51(m, 3H)

Preparation Example 14

Synthesis of 1-(2-chlorophenyl)-(S,S)-1,2-propanediol

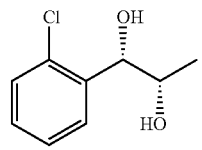

1-(2-chlorophenyl)-trans-1-propene (1.5 g, Preparation Example 1) was dissolved in 30 mL of the mixture of t-BuOH/H₂O (1:1(V/V)). At 0° C., AD-mix-α (Aldrich, U.S.A.) (13.7 g) and methane sulfone amide (CH₃SO₂NH₂, 0.76 g, 0.0080 mol) were added thereto and stirred for overnight. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (1.65 g, yield 90%).

¹H NMR(400 MHz, CDCl₃) δ1.20(d, J=6.4 Hz, 3H), 2.48 (d, J=4.0 Hz 1H), 2.92(d, J=4.4 Hz, 1H), 3.93~3.97(m, 1H), 4.97(t, J=4.8 Hz, 1H), 7.22~7.51(m, 4H)

¹³CNMR(100 MHz,CDCl₃) δ18.8, 71.5, 74.4, 127.1, 128.1, 128.9, 129.5, 132.6, 138.9

Preparation Example 15

Synthesis of 1-(2-chlorophenyl)-(R,R)-1,2-propanediol

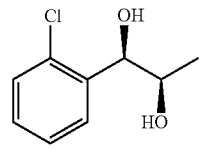

1-(2-chlorophenyl)-trans-1-propene (2.5 g, Preparation Example 1) was dissolved in 50 mL of the mixture of t-BuOH/H₂O (1:1(V/V)). At 0° C., AD-mix-α (Aldrich, U.S.A.) (23.5 g) and methane sulfone amide (CH₃SO₂NH₂, 1.27 g, 0.013 mol) were added thereto and stirred for overnight. When the reaction was completed, the obtained product was washed with an aqueous solution of sodium sulfite (Na₂SO₃) and ethylacetate (EA). Then, the organic layer was dehydrated with anhydrous magnesium sulfate (MgSO₄), filtrated, and concented under reduced pressure. The concentrated residue was purified by a silica gel column chromatography to produce the title compound (2.96 g, yield 90%).

¹H NMR(400 MHz, CDCl₃) δ1.20(d, J=6.4 Hz, 3H), 2.48 (d, J=4.0 Hz, 1H), 2.92(d, J=4.4 Hz, 1H), 3.93~3.97(m, 1H), 4.97(t, J=4.8 Hz, 1H), 7.22~7.51(m, 4H)

Preparation Example 16

Synthesis of the mixture of 1-(2-chlorophenyl)-(S,S)-1,2-propanediol and 1-(2-chlorophenyl)-(R,R)-1,2-propanediol

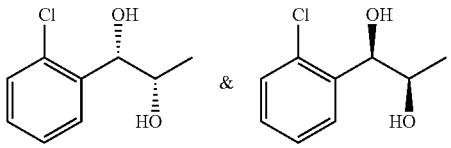

1-(2-chlorophenyl)-trans-1-propene (6.53 g, Preparation Example 1) was dissolved in 45 mL of the mixture of acetone/t-BuOH/H₂O (5:1:1 V/V). At the room temperature, N-methylmorpholine-N-oxide (7.51 g) and OsO₄ (0.54 g) were added thereto and stirred for 2-3 hours. When the reaction was completed, the obtained product was washed with water and methylenechloride (MC). Then, the organic layer was dehydrated with anhydrous magnesium sulfate (MgSO₄), filtrated, and concented under reduced pressure. The concentrated residue was purified by a silica gel column chromatography to produce the title compound (6.42 g, yield 80%).

¹H NMR(400 MHz, CDCl₃) δ1.20(d, J=6.4 Hz, 3H), 2.48 (d, J=4.0 Hz, 1H), 2.92(d, J=4.4 Hz, 1H), 3.93~3.97(m, 1H), 4.97(t, J=4.8 Hz, 1H), 7.22~7.51(m, 4H)

Preparation Example 17

Synthesis of 1-(2-chlorophenyl)-(S,S)-1,2-butanediol

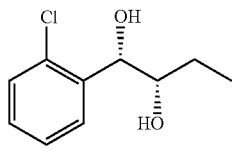

The substantially same method as described in Preparation Example 14 was conducted, except that 1-(2-chlorophenyl)-trans-1-butene (Preparation Example 2) was used instead of 1-(2-chlorophenyl)-trans-1-propene (Preparation Example 1), to obtain the title compound (0.36 g, yield 95%).

$^1$H NMR(400 MHz, CDCl$_3$) δ1.01(t, J=7.4 Hz, 3H), 1.52~1.65(m, 2H), 2.01(d, J=4.4 Hz, 1H), 2.74(d, J=5.2 Hz, 1H), 3.69~3.75(m, 1H), 5.05(t, J=5.0 Hz, 1H), 7.23~7.54(m, 4H)

Preparation Example 18

Synthesis of 1-(2-chlorophenyl)-(R,R)-1,2-butanediol

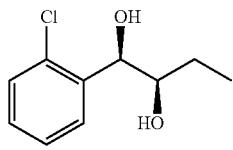

The substantially same method as described in Preparation Example 15 was conducted, except that 1-(2-chlorophenyl)-trans-1-butene (Preparation Example 2) was used instead of 1-(2-chlorophenyl)-trans-1-propene (Preparation Example 1), to obtain the title compound (0.84 g, yield 60~95%).

$^1$H NMR(400 MHz, CDCl$_3$) δ1.01(1, J=7.4 Hz, 3H), 1.52~1.65(m, 2H), 2.01(d, J=4.4 Hz, 1H), 2.74(d, J=5.2 Hz, 1H), 3.69~3.75(m, 1H), 5.05(t, J=5.0 Hz, 1H), 7.23~7.54(m, 4H)

Preparation Example 19

Synthesis of the mixture of 1-(2-chlorophenyl)-(S,S)-1,2-butanediol and 1-(2-chlorophenyl)-(R,R)-1,2-butanediol

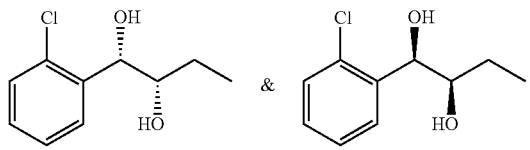

The substantially same method as described in Preparation Example 16 was conducted, except that 1-(2-chlorophenyl)-trans-1-butene (Preparation Example 2) was used instead of 1-(2-chlorophenyl)-trans-1-propene (Preparation Example 1), to obtain the title compound (5.1 g, yield 60~90%).

$^1$H NMR(400 MHz, CDCl$_3$) δ1.01(1, J=7.4 Hz, 3H), 1.52~1.65(m, 2H), 2.01(d, J=4.4 Hz, 1H), 2.74(d, J=5.2 Hz, 1H), 3.69~3.75(m, 1H), 5.05(t, J=5.0 Hz, 1H), 7.23~7.54(m, 4H)

Preparation Example 20

Synthesis of 1-(2-chlorophenyl)-3-methyl-(S,S)-1,2-butanediol

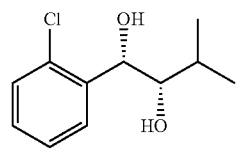

The substantially same method as described in Preparation Example 14 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.96 g, yield 60~90%).

$^1$H NMR(400 MHz, CDCl$_3$) δ1.07(1, J=7.2 Hz, 6H), 1.83~1.89(m, 1H), 1.92(d, J=5.6 Hz, 1H), 2.69(d, J=6.4 Hz, 1H), 3.53~3.56(m, 1H), 5.22~5.25(m, 1H), 7.23~7.55(m, 4H)

Preparation Example 21

Synthesis of 1-(2-chlorophenyl)-3-methyl-(R,R)-1,2-butanediol

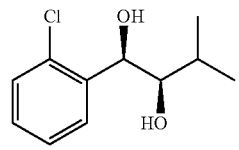

The substantially same method as described in Preparation Example 15 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (4.2 g, yield 60~90%).

$^1$H NMR(400 MHz, CDCl$_3$) δ1.07(1, J=7.2 Hz, 6H), 1.82~1.90(m, 1H), 1.93(d, J=5.6 Hz, 1H), 2.79(d, J=6 Hz, 1H), 3.53~3.57(m, 1H), 5.23~5.25(m, 1H), 7.23~7.54(m, 4H)

Preparation Example 22

Synthesis of the mixture of 1-(2-chlorophenyl)-3-methyl-(S,S)-1,2-butanediol and 1-(2-chlorophenyl)-3-methyl-(R,R)-1,2-butanediol

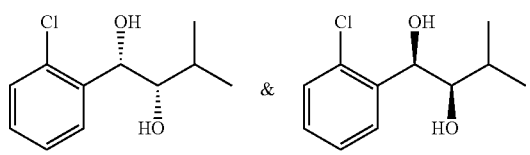

The substantially same method as described in Preparation Example 16 was conducted, except that 1-(2-chlorophenyl)-3-methyl-trans-1-butene (Preparation Example 3) was used instead of 1-(2-chlorophenyl)-trans-1-propene (Preparation Example 1), to obtain the title compound (0.8 g, yield 60~90%).

¹H NMR(400 MHz, CDCl₃) δ1.07(1, J=7.2 Hz, 6H), 1.83~1.90(m, 1H), 1.92(d, J=5.6 Hz, 1H), 2.69(d, J=6.4 Hz, 1H), 3.53~3.56(m, 1H), 5.22~5.25(m, 1H), 7.23~7.55(m, 4H)

Preparation Example 23

Synthesis of 1-(2-chlorophenyl)-(S,S)-1,2-hexanediol

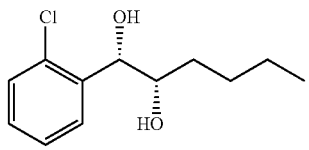

The substantially same method as described in Preparation Example 14 was conducted, except that 1-(2-chlorophenyl)-trans-1-hexene (Preparation Example 4) was used instead of 1-(2-chlorophenyl)-trans-1-propene (Preparation Example 1), to obtain the title compound (0.37 g, yield 90%).

¹H NMR(400 MHz, CDCl₃) δ0.90(t, J=7.2 Hz, 3H), 1.35~1.65(m, 6H), 2.08(d, J=4.4 Hz, 1H), 2.71(d, J=5.2 Hz, 1H), 3.78~3.83(m, 1H), 5.04(t, J=5.0 Hz, 1H), 7.23~7.53(m, 4H)

Preparation Example 24

Synthesis of 1-(2-chlorophenyl)-(R,R)-1,2-hexanediol

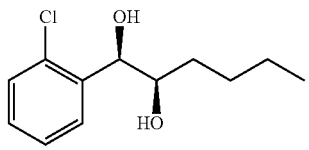

The substantially same method as described in Preparation Example 15 was conducted, except that 1-(2-chlorophenyl)-trans-1-hexene (Preparation Example 4) was used instead of 1-(2-chlorophenyl)-trans-1-propene (Preparation Example 1), to obtain the title compound (4.2 g, yield 60~90%).

¹H NMR(400 MHz, CDCl₃) δ0.91(t, J=6.6 Hz, 3H), 1.35~1.65(m, 6H), 2.08(d, J=4.8 Hz, 1H), 2.70(d, J=5.2 Hz, 1H), 3.78~3.83(m, 1H), 5.05(t, J=5.0 Hz, 1H), 7.23~7.56(m, 4H)

Preparation Example 25

Synthesis of the mixture of 1-(2-chlorophenyl)-(S,S)-1,2-hexanediol and 1-(2-chlorophenyl)-(R,R)-1,2-hexanediol

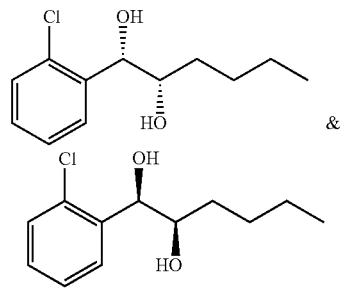

The substantially same method as described in Preparation Example 16 was conducted, except that 1-(2-chlorophenyl)-trans-1-hexene (Preparation Example 4) was used instead of 1-(2-chlorophenyl)-trans-1-propene (Preparation Example 1), to obtain the title compound (7.9 g, yield 60~90%).

¹H NMR(400 MHz, CDCl₃) δ0.90(t, J=7.2 Hz, 3H), 1.26~1.55(m, 6H), 2.08(d, J=4.4 Hz, 1H), 2.71(d, J=5.6 Hz, 1H), 3.78~3.84(m, 1H), 5.04(t, J=3.2 Hz, 1H), 7.24~7.55(m, 4H)

Preparation Example 26

Synthesis of 1-(2,4-dichlorophenyl)-(S,S)-1,2-propanediol

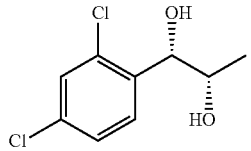

The substantially same method as described in Preparation Example 14 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.33 g, yield 60~95%).

¹H NMR(400 MHz, CDCl₃) δ1.22(d, J=6.4 Hz, 3H), 2.10 (d, J=4.4 Hz, 1H), 2.71(d, J=4.8 Hz, 1H), 3.90~3.95(m, 1H), 4.94(t, J=5.0 Hz, 1H), 7.31(dd, J=2.0 Hz, J=8.0 Hz, 1H), 7.40(d, J=2.0 Hz, 1H), 7.49(d, J=8.4 Hz, 1H)

Preparation Example 27

Synthesis of 1-(2,4-dichlorophenyl)-(R,R)-1,2-propanediol

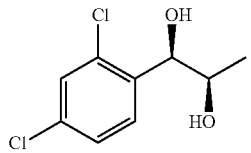

The substantially same method as described in Preparation Example 15 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR(400 MHz, CDCl$_3$) δ1.22(d, J=6.4 Hz, 3H), 2.10 (d, J=4.4 Hz, 1H), 2.71(d, J=4.8 Hz, 1H), 3.90~3.95(m, 1H), 4.94(t, J=5.0 Hz, 1H), 7.31~7.49(m, 3H)

Preparation Example 28

Synthesis of the mixture of 1-(2,4-dichlorophenyl)-(S,S)-1,2-propanediol and 1-(2,4-dichlorophenyl)-(R,R)-1,2-propanediol

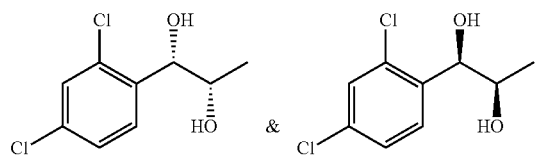

The substantially same method as described in Preparation Example 16 was conducted, except that 1-(2,4-dichlorophenyl)-trans-1-propene (Preparation Example 5) was used instead of 1-(2-chlorophenyl)-trans-1-propene (Preparation Example 1), to obtain the title compound (0.45 g, yield 60~95%).

$^1$H NMR(400 MHz, CDCl$_3$) δ1.22(d, J=6.4 Hz, 3H), 2.10 (d, J=4.4 Hz, 1H), 2.71(d, J=4.8 Hz, 1H), 3.90~3.95(m, 1H), 4.94(t, J=5.0 Hz, 1H), 7.31~7.49(m, 3H)

Preparation Example 29

Synthesis of 1-(2,4-dichlorophenyl)-(S,S)-1,2-butanediol

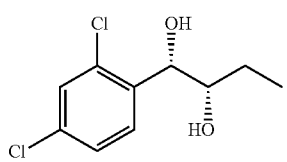

The substantially same method as described in Preparation Example 14 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.32 g, yield 90%).

$^1$H NMR(400 MHz, CDCl$_3$) δ1.02(1, J=7.4 Hz, 3H), 1.54~1.61(m, 2H), 2.07(d, J=4.8 Hz, 1H), 2.74(d, J=4.8 Hz, 1H), 3.65~3.68(m, 1H), 5.01(t, J=5.0 Hz, 1H), 7.31~7.49(m, 3H)

Preparation Example 30

Synthesis of 1-(2,4-dichlorophenyl)-(R,R)-1,2-butanediol

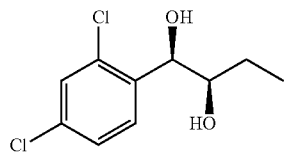

The substantially same method as described in Preparation Example 15 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.43 g, yield 60~90%).

$^1$H NMR(400 MHz, CDCl$_3$) δ1.02(1, J=7.4 Hz, 3H), 1.54~1.61(m, 2H), 2.07(d, J=4.8 Hz, 1H), 2.74(d, J=4.8 Hz, 1H), 3.65~3.68(m, 1H), 5.01(t, J=5.0 Hz, 1H), 7.31~7.49(m, 3H)

Preparation Example 31

Synthesis of the mixture of 1-(2,4-dichlorophenyl)-(S,S)-1,2-butanediol and 1-(2,4-dichlorophenyl)-(R,R)-1,2-butanediol

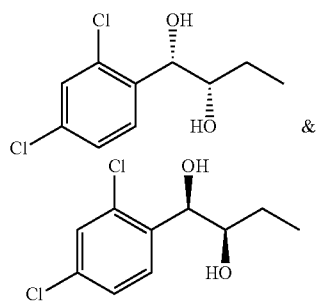

The substantially same method as described in Preparation Example 16 was conducted, except that 1-(2,4-dichlorophenyl)-trans-1-butene (Preparation Example 6) was used instead of 1-(2-chlorophenyl)-trans-1-propene (Preparation Example 1), to obtain the title compound (0.33 g, yield 60~90%).

$^1$H NMR(400 MHz, CDCl$_3$) δ1.02(1, J=7.4 Hz, 3H), 1.54~1.61(m, 2H), 2.07(d, J=4.8 Hz, 1H), 2.74(d, J=4.8 Hz, 1H), 3.65~3.68(m, 1H), 5.01(t, J=5.0 Hz, 1H), 77.31~7.49 (m, 3H)

Preparation Example 32

Synthesis of 1-(2,4-dichlorophenyl)-3-methyl-(S,S)-1,2-butanediol

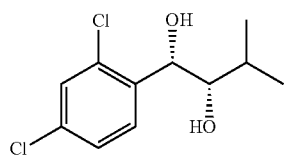

The substantially same method as described in Preparation Example 14 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.25 g, yield 60~95%).

¹H NMR(400 MHz, CDCl₃) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 33

Synthesis of 1-(2,4-dichlorophenyl)-3-methyl-(R,R)-1,2-butanediol

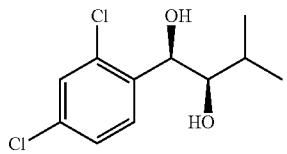

The substantially same method as described in Preparation Example 15 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.36 g, yield 60~95%).

¹H NMR(400 MHz, CDCl₃) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 34

Synthesis of the mixture of 1-(2,4-dichlorophenyl)-3-methyl-(S,S)-1,2-butanediol and 1-(2,4-dichlorophenyl)-3-methyl-(R,R)-1,2-butanediol

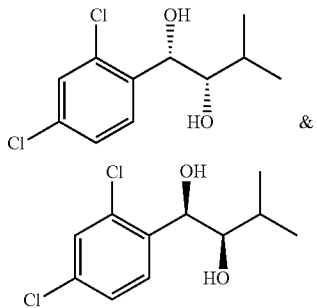

The substantially same method as described in Preparation Example 16 was conducted, except that 1-(2,4-dichlorophenyl)-3-methyl-trans-1-butene (Preparation Example 7) was used instead of 1-(2-chlorophenyl)-trans-1-propene (Preparation Example 1), to obtain the title compound (0.26 g, yield 60~95%).

¹H NMR(400 MHz, CDCl₃) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 35

Synthesis of 1-(2,4-dichlorophenyl)-(S,S)-1,2-hexanediol

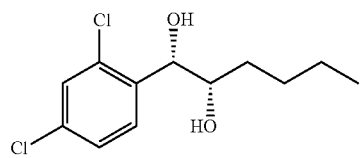 [SMILES: CCCC[C@H](O)[C@@H](O)c1ccc(Cl)cc1Cl]

The substantially same method as described in Preparation Example 14 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.1 g, yield 60~90%).

¹H NMR(400 MHz, CDCl₃) δ0.89~0.93(m, 3H), 1.30~1.39(m, 2H), 1.49~1.52(m, 2H), 1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H), 7.28~7.50(m, 3H)

Preparation Example 36

Synthesis of 1-(2,4-dichlorophenyl)-(R,R)-1,2-hexanediol

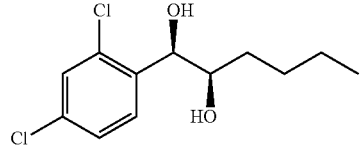 [SMILES: CCCC[C@@H](O)[C@H](O)c1ccc(Cl)cc1Cl]

The substantially same method as described in Preparation Example 15 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (1.2 g, yield 60~95%).

¹H NMR(400 MHz, CDCl₃) δ0.89~0.93(m, 3H), 1.30~1.39(m, 2H), 1.49~1.52(m, 2H), 1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H), 7.28~7.50(m, 3H)

Preparation Example 37

Synthesis of the mixture of 1-(2,4-dichlorophenyl)-(S,S)-1,2-hexanediol and 1-(2,4-dichlorophenyl)-(R,R)-1,2-hexanediol

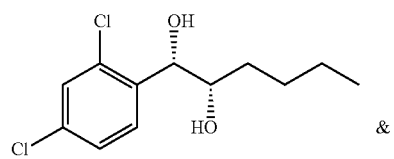

-continued

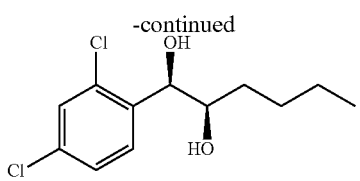

The substantially same method as described in Preparation Example 16 was conducted, except that 1-(2,4-dichlorophenyl)-trans-1-hexene (Preparation Example 8) was used instead of 1-(2-chlorophenyl)-trans-1-propene (Preparation Example 1), to obtain the title compound (0.67 g, yield 60~95%).

$^1$H NMR(400 MHz, CDCl$_3$) δ0.89~0.93(m, 3H), 1.30~1.39(m, 2H), 1.49~1.52(m, 2H), 1.56~1.62(m, 2H), 2.05(d, J=5.2 Hz, 1H), 2.74(d, J=5.2 Hz, 1H), 3.72~3.77(m, 1H), 4.98(t, J=4.8 Hz, 1H), 7.28~7.50(m, 3H)

Preparation Example 38

Synthesis of 1-(2,6-dichlorophenyl)-(S,S)-1,2-propanediol

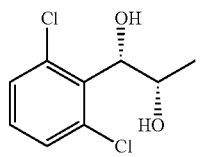

The substantially same method as described in Preparation Example 14 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.9 g, yield 60~90%).

$^1$H NMR(400 MHz, CDCl$_3$) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~7.36(m, 3H)

Preparation Example 39

Synthesis of 1-(2,6-dichlorophenyl)-(R,R)-1,2-propanediol

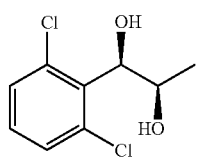

The substantially same method as described in Preparation Example 15 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.84 g, yield 60~90%).

$^1$H NMR(400 MHz, CDCl$_3$) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~7.36(m, 3H)

Preparation Example 40

Synthesis of the mixture of 1-(2,6-dichlorophenyl)-(S,S)-1,2-propanediol and 1-(2,6-dichlorophenyl)-(R,R)-1,2-propanediol

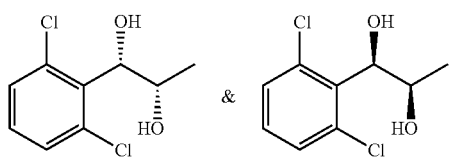

The substantially same method as described in Preparation Example 16 was conducted, except that 1-(2,6-dichlorophenyl)-trans-1-propene (Preparation Example 9) was used instead of 1-(2-chlorophenyl)-trans-1-propene (Preparation Example 1), to obtain the title compound (0.91 g, yield 60~90%).

$^1$H NMR(400 MHz, CDCl$_3$) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~7.36(m, 3H)

Preparation Example 41

Synthesis of 1-(2,6-dichlorophenyl)-(S,S)-1,2-butanediol

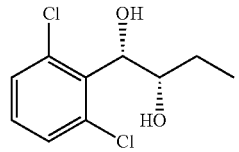

The substantially same method as described in Preparation Example 14 was conducted, except that 1-(2,6-dichlorophenyl)-trans-1-butene (Preparation Example 10) was used instead of 1-(2-chlorophenyl)-trans-1-propene (Preparation Example 1), to obtain the title compound (1.23 g, yield 60~95%).

$^1$H NMR(400 MHz, CDCl$_3$) δ0.97(t, J=7.6 Hz, 3H), 1.26~1.53(m, 2H), 2.64(dd, J=0.8 Hz, J=4.0 Hz, 1H), 3.14(d, J=8.4 Hz, 1H), 4.22~4.26(m, 1H), 5.26(t, J=8.4 Hz, 1H), 7.17~7.35(m, 3H)

Preparation Example 42

Synthesis of 1-(2,6-dichlorophenyl)-(R,R)-1,2-butanediol

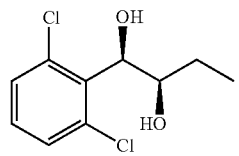

The substantially same method as described in Preparation Example 15 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.96 g, yield 60~95%).

$^1$H NMR(400 MHz, CDCl$_3$) δ0.97(t, J=7.6 Hz, 3H), 1.26~1.53(m, 2H), 2.64(dd, J=0.8 Hz, J=4.0 Hz, 1H), 3.14(d, J=8.4 Hz, 1H), 4.22~4.26(m, 1H), 5.26(t, J=8.4 Hz, 1H), 7.17~7.35(m, 3H)

Preparation Example 43

Synthesis of the mixture of 1-(2,6-dichlorophenyl)-(S,S)-1,2-butanediol and 1-(2,6-dichlorophenyl)-(R,R)-1,2-butanediol

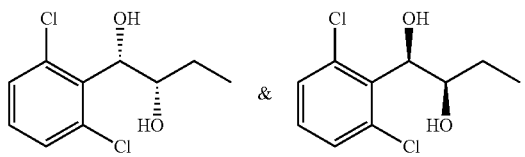

The substantially same method as described in Preparation Example 16 was conducted, except that 1-(2,6-dichlorophenyl)-trans-1-butene (Preparation Example 10) was used instead of 1-(2-chlorophenyl)-trans-1-propene (Preparation Example 1), to obtain the title compound (0.86 g, yield 60~95%).

$^1$H NMR(400 MHz, CDCl$_3$) δ0.97(t, J=7.6 Hz, 3H), 1.26~1.53(m, 2H), 2.64(dd, J=0.8 Hz, J=4.0 Hz, 1H), 3.14(d, J=8.4 Hz, 1H), 4.22~4.26(m, 1H), 5.26(t, J=8.4 Hz, 1H), 7.17~7.35(m, 3H)

Preparation Example 44

Synthesis of 1-(2,6-dichlorophenyl)-3-methyl-(S,S)-1,2-butanediol

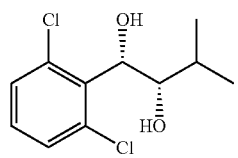

The substantially same method as described in Preparation Example 14 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.25 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 45

Synthesis of 1-(2,6-dichlorophenyl)-3-methyl-(R,R)-1,2-butanediol

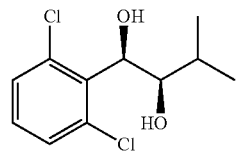

The substantially same method as described in Preparation Example 15 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.37 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 46

Synthesis of the mixture of 1-(2,6-dichlorophenyl)-3-methyl-(S,S)-1,2-butanediol and 1-(2,6-dichlorophenyl)-3-methyl-(R,R)-1,2-butanediol

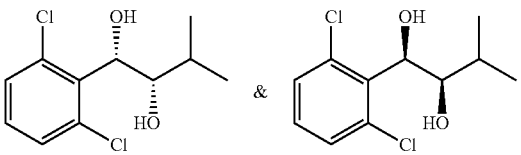

The substantially same method as described in Preparation Example 16 was conducted, except that 1-(2,6-dichlorophenyl)-3-methyl-trans-1-butene (Preparation Example 11) was used instead of 1-(2-chlorophenyl)-trans-1-propene (Preparation Example 1), to obtain the title compound (0.47 g, yield 60~95%).

$^1$H NMR(400 MHz, CDCl$_3$) δ1.00(d, J=6.8 Hz, 6H), 1.60~1.65(m, 1H), 2.35(d, J=4.0 Hz, 1H), 3.12(d, J=8.4 Hz, 1H), 4.13~4.18(m, 1H), 5.36(t, J=7.6 Hz, 1H), 7.17~7.35(m, 3H)

Preparation Example 47

Synthesis of 1-(2,6-dichlorophenyl)-(S,S)-1,2-hexanediol

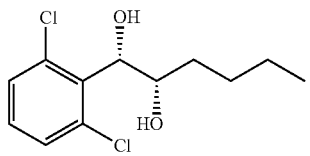 [SMILES: CCCC[C@H](O)[C@@H](O)c1c(Cl)cccc1Cl]

The substantially same method as described in Preparation Example 14 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.36 g, yield 60~90%).

$^1$H NMR(400 MHz, CDCl$_3$) δ0.85(t, J=6.8 Hz, 3H), 1.20~1.31(m, 4H), 1.45~1.53(m, 2H), 2.61~2.62(m, 1H), 3.12(d, J=8.4 Hz, 1H), 4.28~4.33(m, 1H), 5.25(t, J=8.4 Hz, 1H), 7.18~7.35(m, 3H)

Preparation Example 48

Synthesis of 1-(2,6-dichlorophenyl)-(R,R)-1,2-hexanediol

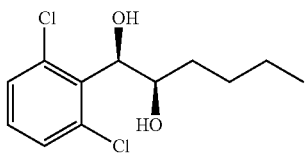 [SMILES: CCCC[C@@H](O)[C@H](O)c1c(Cl)cccc1Cl]

The substantially same method as described in Preparation Example 15 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.58 g, yield 60~90%).

$^1$H NMR(400 MHz, CDCl$_3$) δ0.85(t, J=6.8 Hz, 3H), 1.20~1.31(m, 4H), 1.45~1.53(m, 2H), 2.61~2.62(m, 1H), 3.12(d, J=8.4 Hz, 1H), 4.28~4.33(m, 1H), 5.25(t, J=8.4 Hz, 1H), 7.18~7.35(m, 3H)

Preparation Example 49

Synthesis of the mixture of 1-(2,6-dichlorophenyl)-(S,S)-1,2-hexanediol and 1-(2,6-dichlorophenyl)-(R,R)-1,2-hexanediol

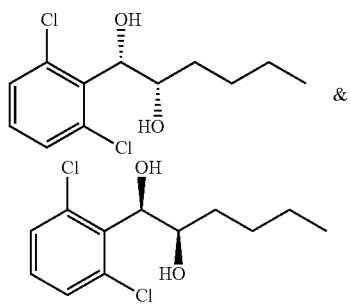

The substantially same method as described in Preparation Example 16 was conducted, except that 1-(2,6-dichlorophenyl)-trans-1-hexene (Preparation Example 12) was used instead of 1-(2-chlorophenyl)-trans-1-propene (Preparation Example 1), to obtain the title compound (0.62 g, yield 60~90%).

$^1$H NMR(400 MHz, CDCl$_3$) δ0.85(t, J=6.8 Hz, 3H), 1.20~1.31(m, 4H), 1.45~1.53(m, 2H), 2.61~2.62(m, 1H), 3.12(d, J=8.4 Hz, 1H), 4.28~4.33(m, 1H), 5.25(t, J=8.4 Hz, 1H), 7.18~7.35(m, 3H)

Preparation Example 50

Synthesis of methyl 2-(2-chlorophenyl)-(R)-2-hydroxyacetate

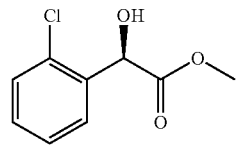

15 g of (R)-2-chloromandelic acid was mixed with methanol (CH$_3$OH, 150 ml) and phosphorus chloride oxide (POCl$_3$, 0.76 ml) in a flask by stirring using a magnetic stirrer at the room temperature for 6 hours. When the reaction was completed, the obtained product was washed with an aqueous solution of sodium sulfite (Na$_2$SO$_3$) and ethylacetate (EA). Then, the organic layer was dehydrated with anhydrous magnesium sulfate (MgSO$_4$), filtrated, and concented under reduced pressure. The concentrated residue was purified by a silica gel column chromatography to produce the title compound (15.64 g, yield 95%).

$^1$H NMR(400 MHz, CDCl$_3$) δ 3.59(d, J=5.2, 1H), 3.79(t, J=6.0, 3H), 5.59(d, J=5.2, 1H), 7.28~7.43(m, 4H)

Preparation Example 51

Synthesis of 2-(2-chlorophenyl)-(R)-2-hydroxy-N-methoxy-N-methylacetamide

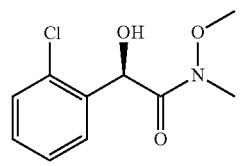

N,O-dimethylhydroxylamine hydrochloride (N,O-dimethylhydroxylamine.HCl, 15.2 g) was dissolved in dichloromethane (DCM, 150 ml), and cooled to 0° C. using an ice-bath. Then, 77.7 ml of 2.0M trimethylaluminium in hexane was slowly added thereto in drop-wise manner for 30 minutes. Thereafter, the ice-bath was removed, and the obtained product was stirred at the room temperature for 2 hours. Methyl-2-(2-chlorophenyl)-(R)-2-hydroxyacetate (15.64 g) dissolved in dichloromethane (DCM, 150 ml) was added in drop-wise manner thereto at the room temperature for 30 minutes, and subjected to reflux for 12 hours. When the reaction was completed, the obtained product was cooled to 0° C., and washed by a slow drop-wise addition of hydrochloric acid (HCl, 200 ml). The obtained organic layer was washed with distilled water and brine, dehydrated with anhydrous magnesium sulfate (MgSO$_4$), filtrated, and concented under reduced pressure. The concentrated residue was purified by a silica gel column chromatography to produce the title compound (14.68 g, yield 82%).

¹H NMR(400 MHz, CDCl₃) δ3.23(s, 3H), 3.28(s, 3H), 4.33(d, J=6.0 Hz, 1H), 5.81(d, J=5.6 Hz, 1H), 7.23~7.42(m, 4H)

Preparation Example 52

Synthesis of 2-(2-chlorophenyl)-N-methoxy-(R)-2-(t-butyl dimethlysiloxy)-N-methylacetamide

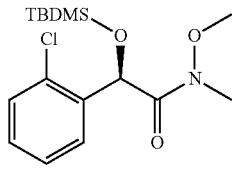

2-(2-chlorophenyl)-(R)-2-hydroxy-N-methoxy-N-methylacetamide (0.81 g, 3.52 mmol) obtained in Preparation Example 51 was dissolved in dichloromethane (DCM), and cooled to 0° C. Imedazole (0.36 g, 5.28 mmol) was slowly added, and stirred. TBDMS-Cl (t-butyldimethylsily chloride, 0.79 g, 5.28 mmol) was slowly added. When the reaction was completed, the reaction mixture was quenched with H₂O. The organic layer was separated and collected. The aqueous layer was extracted with CH₂Cl₂(300 mL), dried over MgSO₄ Concentration under vacuum provided a title compound. (0.97 g, 80~95%).

¹H NMR(400 MHz, CDCl₃) δ-0.03(s, 3H), 0.14(s, 3H), 0.94(s, 9H), 2.97(s, 3H), 3.02(s, 3H), 5.83(s, 1H), 7.28~7.60 (m, 4H)

Preparation Example 53

Synthesis of 1-(2-chlorophenyl)-(R)-1-(t-butyldimethyl-siloxy)propane-2-on

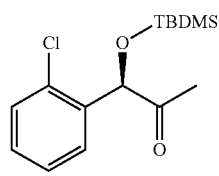

2-(2-chlorophenyl)-N-methoxy-(R)-2-(t-butyldimethylsiloxy)-N-methylacetamide (0.9 g) obtained in Preparation Example 52 was dissolved in tetrahydrofuran (THF), and cooled to 0° C. 3.0M methyl magnesium bromide (MeMgBr, 2.18 ml) solution in ether was added thereto in drop-wise manner for 30 minutes, and the obtained product was stirred at 0° C. When the reaction was completed, diethylether was added thereto. The obtained product was washed with 10% (w/v) potassium hydrogen sulfate (KHSO₄, 100 ml) and then, washed again with brine. The obtained organic layer was dehydrated with anhydrous magnesium sulfate (MgSO₄), filtrated, and concentrated under reduced pressure. The concentrated residue was purified by a silica gel column chromatography to produce the title compound (0.69 g, yield 85~95%).

¹H NMR(400 MHz, CDCl₃) δ-0.3(s, 3H), 0.14(s, 3H), 0.94(s, 9H), 2.18(s, 3H), 5.50(s, 1H), 7.27~7.56(m, 4H)

Preparation Example 54

Synthesis of 1-(2-chlorophenyl)-(R)-1-(t-butyldimethyl-siloxy)-(S)-2-propanol

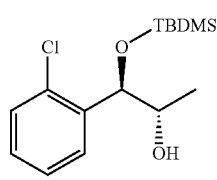

1-(2-chlorophenyl)-(R)-1-(t-butyldimethyl-siloxy)propane-2-on (0.14 g) obtained in Preparation Example 53 was dissolved in ether, and cooled to −78° C. Zinc borohydride (Zn(BH₄)₂) was slowly added thereto and the obtained product was stirred. When the reaction was completed, the obtained product was washed by H₂O. The obtained organic layer was washed with H₂O, dehydrated with anhydrous magnesium sulfate (MgSO₄), filtrated, and concentrated under reduced pressure. The concentrated residue was purified by a silica gel column chromatography to produce the title compound (0.04 g, yield 25~33%, cis:trans=2:1).

¹H NMR(400 MHz, CDCl₃) δ-0.11(s, 3H), 0.11(s, 3H), 0.93(S, 9H), 1.07(d, J=6.4 3H), 2.05(d, J=6.4 1H), 4.01~4.05 (m, 1H), 5.18(d, J=4.0, 1H), 7.20~7.56(m, 4H))

Preparation Example 55

Synthesis of 1-(2-chlorophenyl)-(R,S)-1,2-propanediol

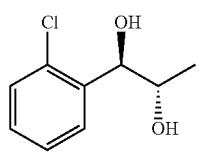

1-(2-chlorophenyl)-(R)-1-(t-butyldimethyl-siloxy)-(S)-2-propanol (10.38 g) obtained in Preparation Example 54 was dissolved in methanol (CH₃OH, 100 ml), and then, cooled to 0° C. 8M hydrochloric acid (HCl, 56.2 ml) was slowly added in drop-wise manner to the obtained product, and then, the obtained product was warmed to the room temperature, and stirred for 15 hours. When the reaction was completed, the obtained product was cooled to 0° C. 5N sodium hydroxide (NaOH, 30 ml) was slowly added thereto, and the obtained product was subjected to vacuum concentration. The obtained product was diluted with ethylacetate. The obtained organic layer was washed with distilled water, dehydrated with anhydrous magnesium sulfate (MgSO₄), filtrated, and concented under reduced pressure. The concentrated residue was purified by a silica gel column chromatography to produce the title compound (7.05 g, yield 60~90%).

¹H NMR(400 MHz, CDCl₃) δ1.07(d, J=6.8, 3H), 2.01(d, J=5.6, 1H), 2.61(s, 1H), 4.21~4.27(m, 1H), 5.24(d, J=3.6, 1H), 7.22~7.64(m, 4H)

Preparation Example 56

Synthesis of
1-(2-chlorophenyl)-(S,R)-1,2-propanediol

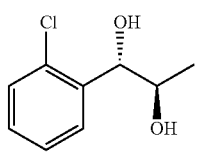

The substantially same method as described in Preparation Example 50~55 was conducted, except that (S)-2-chloromandelic acid was used instead of (R)-2-chloromandelic acid, to obtain the title compound (5.04 g, yield 84%).
¹H NMR(400 MHz, CDCl₃) δ1.07(d, J=6.8, 3H), 2.00(d, J=5.6, 1H), 2.54(d, J=3.6, 1H), 4.22~4.26(m, 1H), 5.25(t, J=3.2, 1H), 7.22~7.65(m, 4H)

Preparation Example 57

Synthesis of
1-(2,3-dichlorophenyl)-(S,S)-1,2-propanediol

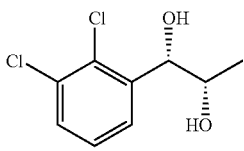

The substantially same method as described in Preparation Example 14 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.9 g, yield 60~90%).
¹H NMR(400 MHz, CDCl₃) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~(m, 3H)

Preparation Example 58

Synthesis of
1-(2,3-dichlorophenyl)-(R,R)-1,2-propanediol

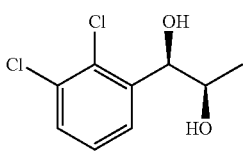

The substantially same method as described in Preparation Example 15 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.84 g, yield 60~90%).
¹H NMR(400 MHz, CDCl₃) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~ (m, 3H)

Preparation Example 59

Synthesis of the mixture of 1-(2,3-dichlorophenyl)-
(S,S)-1,2-propanediol and 1-(2,3-dichlorophenyl)-
(R,R)-1,2-propanediol

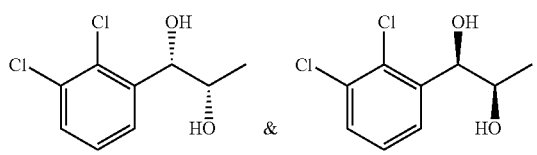

The substantially same method as described in Preparation Example 16 was conducted, except that 1-(2,3-dichlorophenyl)-trans-1-propene (Preparation Example 13) was used instead of 1-(2-chlorophenyl)-trans-1-propene (Preparation Example 1), to obtain the title compound (0.91 g, yield 60~90%).
¹H NMR(400 MHz, CDCl₃) δ1.10(d, J=6.4 Hz, 3H), 2.72 (d, J=2.4 Hz, 1H), 3.10(d, J=8.4 Hz, 1H), 4.47~4.54(m, 1H), 5.24(t, J=8.8 Hz, 1H), 7.18~(m, 3H)

Preparation Example 60

Synthesis of 1-(2-fluorophenyl)-trans-1-propene

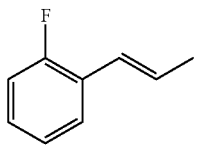

The substantially same method as described in Preparation Example 1 was conducted, except that 2-fluorobenzenaldehyde was used instead of 2-chlorobenzenealdehyde, to obtain the title compound (6.67 g, yield 61%).
¹H NMR(400 MHz, CDCl₃) δ1.94(d, J=6.8 Hz, 3H), 6.30~6.38(m, 1H), 6.57(d, J=16 Hz, 1H), 7.00~7.41(m, 4H)

Preparation Example 61

Synthesis of
1-(2-fluorophenyl)-(S,S)-1,2-propanediol

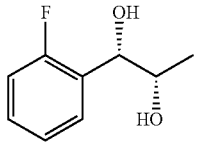

The substantially same method as described in Preparation Example 14 was conducted, except that 1-(2-fluorophenyl)- trans-1-propene (Preparation Example 60) was used instead of 1-(2-chlorophenyl)-trans-1-propene (Preparation Example 1), to obtain the title compound (6.46 g, yield 78%).

¹H NMR(400 MHz, CDCl₃) δ1.15(d, J=6.4 Hz, 3H), 2.43 (d, J=3.6 Hz, 1H), 2.69(d, J=4.8 Hz, 1H), 3.90~3.98(m, 1H), 4.78(dd, J=4.4, 7.2 Hz, 1H), 7.04~7.50(m, 4H)

Preparation Example 62

Synthesis of 1-(2-fluorophenyl)-(R,R)-1,2-propanediol

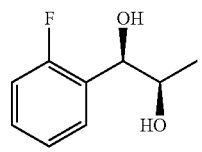

The substantially same method as described in Preparation Example 15 was conducted, except that 1-(2-fluorophenyl)-trans-1-propene (Preparation Example 60) was used instead of 1-(2-chlorophenyl)-trans-1-propene (Preparation Example 1), to obtain the title compound (3.29 g, yield 79%).

¹H NMR(400 MHz, CDCl₃) δ1.15(d, J=6.4 Hz, 3H), 2.43 (d, J=3.6 Hz, 1H), 2.69(d, J=4.8 Hz, 1H), 3.90~3.98(m, 1H), 4.78(dd, J=4.4, 7.2 Hz, 1H), 7.04~7.50(m, 4H)

Preparation Example 63

Synthesis of 2-iodobenzenealdehyde

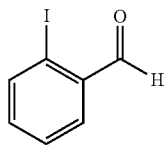

In a flask, 2-iodobenzyl alcohol (4 g, 17.09 mmol) was dissolved in dichloromethane (MC, 85 ml), and then, manganese oxide (MnO₂, 14.86 g, 170.92 mmol) was added thereto. The obtained reaction product was stirred under the reflux condition. When the reaction was completed, the obtained reaction product was cooled to the room temperature, and then, fiteated and concentrated using celite, to obtain the title compound (3.6 g, yield 91%).

¹H NMR(400 MHz, CDCl₃)δ7.30~7.99(m, 4H), 10.10(s, 1H)

Preparation Example 64

Synthesis of 1-(2-iodophenyl)-trans-1-propene

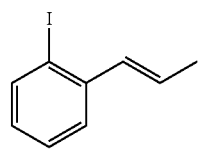

The substantially same method as described in Preparation Example 1 was conducted, except that 2-iodobenzenealdehyde (Preparation Example 63) was used instead of 2-chlorobenzenealdehyde, to obtain the title compound (3.4 g, yield 65%).

¹H NMR(400 MHz, CDCl₃)δ1.95(dd, J=6.8 Hz, 1.6 Hz, 3H), 6.09~6.18(m, 1H), 6.60(dd, J=15.66 Hz, 1.8 Hz, 1H), 6.89~7.84(m, 4H)

Preparation Example 65

Synthesis of 1-(2-iodophenyl)-trans-1-butene

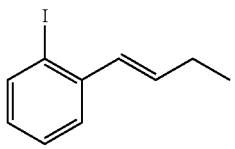

The substantially same method as described in Preparation Example 64 was conducted, except that 3-heptanone was used instead of 3-pentanone, to obtain the title compound (8.5 g, yield 75%).

¹H NMR(400 MHz, CDCl₃)δ1.46(t, J=7.6 Hz, 3H), 2.26~2.34(m, 2H), 6.17(dt, J=15.6 Hz, 6.6 Hz 1H), 6.57(d, J=15.6 Hz, 1H), 6.89~7.85(m, 4H)

Preparation Example 66

Synthesis of 1-(2-iodophenyl)-(S,S)-1,2-propanediol

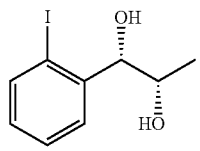

The substantially same method as described in Preparation Example 14 was conducted, except that 1-(2-iodophenyl)-trans-1-propene (Preparation Example 64) was used instead of 1-(2-chlorophenyl)-trans-1-propene (Preparation Example 1), to obtain the title compound (3.4 g, yield 88%).

¹H NMR(400 MHz, CDCl₃)δ1.27(d, J=6.4 Hz, 3H), 2.26 (br s, 1H), 2.74(br s, 1H), 3.99(t, J=6.0 Hz, 1H), 4.81(d, J=4.0 Hz, 1H), 7.01~7.87(m, 4H)

Preparation Example 67

Synthesis of 1-(2-iodorophenyl)-(R,R)-1,2-propanediol

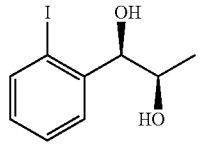

The substantially same method as described in Preparation Example 15 was conducted was conducted, except that 1-(2- iodophenyl)-trans-1-propene (Preparation Example 64) was used instead of 1-(2-chlorophenyl)-trans-1-propene (Preparation Example 1), to obtain the title compound (7.4 g, yield 84%).

$^1$H NMR(400 MHz, CDCl$_3$)δ1.26(d, J=6.4 Hz, 3H), 2.35 (br s, 1H), 2.85(br d, J=4.0 Hz, 1H), 3.98(t, J=6.2 Hz, 1H), 4.80(dd, J=5.0, 4.4 Hz, 1H), 7.00~7.87(m, 4H)

Preparation Example 68

Synthesis of 1-(2-iodophenyl)-(S,S)-1,2-butanediol

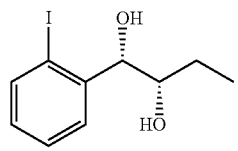

The substantially same method as described in Preparation Example 14 was conducted was conducted, except that 1-(2-iodophenyl)-trans-1-butene (Preparation Example 65) was used instead of 1-(2-chlorophenyl)-trans-1-propene (Preparation Example 1), to obtain the title compound (9.5 g, yield 84%).

$^1$H NMR(400 MHz, CDCl$_3$)δ1.04(t, J=7.6 Hz, 3H), 1.60~1.71(m, 2H), 2.07(br s, 1H), 2.74(br s, 1H), 3.71~3.76 (m, 1H), 4.87(d, J=4.8 Hz, 1H), 7.01~7.87(m, 4H)

Preparation Example 69

Preparation of 1-(2-chlorophenyl)-(S,S)-1,2-(Bis-trimethylsilanyloxy)propane

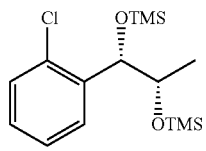

To a stirred solution of 1-(2-chlorophenyl)-(S,S)-1,2-propanediol (Preparation example 14, 67 g, 0.35 mol) in CH$_2$Cl$_2$ (670 ml) was added Et$_3$N (200 mL, 1.43 mol) and TMSCl (113.9 mL, 0.89 mol) at 0° C. under N$_2$.

The reaction mixture was allowed to stir at 0° C. for 3 hr. The reaction mixture was quenched with H$_2$O (650 mL) at 0° C. The organic layer was separated and collected. The aqueous layer was extracted with CH$_2$Cl$_2$ (300 mL), dried over MgSO$_4$. Concentration under vacuum provided a crude product. 104.18 g (117.44%).

$^1$H NMR(400 MHz, CDCl$_3$)δ-0.053(s, 9H), 0.044(s, 9H), 1.15(d, J=5.6 Hz, 3H), 3.977~3.918(m, 1H), 4.973(d, J=6.4 Hz, 1H), 7.207~7.165(m, 1H), 7.321~7.245(m, 2H), 7.566~7.543(m, 1H)

Preparation Example 70

Preparation of 1-(2-chlorophenyl)-(R,R)-1,2-(Bis-trimethylsilanyloxy)propane

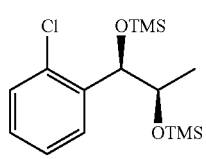

The substantially same method as described in Preparation Example 69 was conducted, except that 1-(2-chlorophenyl)-(R,R)-1,2-propanediol (Preparation example 15) was used instead of 1-(2-chlorophenyl)-(S,S)-1,2-propanediol (Preparation example 14) to obtain the title compound (8.5 g, yield 90~120%).

$^1$H NMR(400 MHz, CDCl$_3$)δ-0.053(s, 9H), 0.044(s, 9H), 1.15(d, J=5.6 Hz, 3H), 3.977~3.918(m, 1H), 4.973(d, J=6.4 Hz, 1H), 7.21~7.54(m, 4H)

Preparation Example 71

Preparation of 1-(2-chlorophenyl)-1,2-(Bis-trimethylsilanyloxy)propane

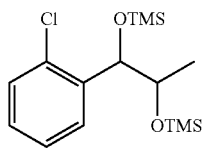

The substantially same method as described in Preparation Example 69 was conducted, except that 1-(2-chlorophenyl) propane-1,2-diol (Preparation example 16) was used instead of 1-(2-chlorophenyl)-(S,S)-1,2-propanediol (Preparation example 14) to obtain the title compound (5.2 g, yield 90~120%).

$^1$H NMR(400 MHz, CDCl$_3$)δ-0.053(s, 9H), 0.044(s, 9H), 1.15(d, J=5.6 Hz, 3H), 3.977~3.918(m, 1H), 4.973(d, J=6.4 Hz, 1H), 7.21~7.54(m, 4H)

Preparation Example 72

Preparation of 1-(2-chlorophenyl)-(S,R)-1,2-(Bis-trimethylsilanyloxy)propane

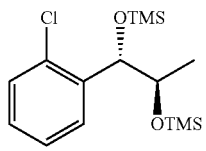

The substantially same method as described in Preparation Example 69 was conducted, except that 1-(2-chlorophenyl)-(S,R)-1,2-propanediol (Preparation example 56) was used instead of 1-(2-chlorophenyl)-(S,S)-1,2-propanediol (Preparation example 14) to obtain the title compound (3.4 g, yield 90~120%).

$^1$H NMR(400 MHz, CDCl$_3$)δ-0.053(s, 9H), 0.044(s, 9H), 1.15(d, J=5.6 Hz, 3H), 3.977~3.918(m, 1H), 4.973(d, J=6.4 Hz, 1H), 7.21~7.54(m, 4H)

Preparation Example 73

Preparation of 1-(2-chlorophenyl)-(R,S)-1,2-(Bis-trimethylsilanyloxy)propane

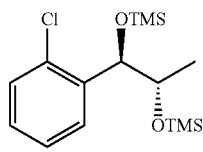

The substantially same method as described in Preparation Example 69 was conducted, except that 1-(2-chlorophenyl)-(R,S)-1,2-propanediol (Preparation example 55) was used instead of 1-(2-chlorophenyl)-(S,S)-1,2-propanediol (Preparation example 14) to obtain the title compound (3.2 g, yield 90~120%).
$^1$H NMR(400 MHz, CDCl$_3$)δ-0.053(s, 9H), 0.044(s, 9H), 1.15(d, J=5.6 Hz, 3H), 3.977~3.918(m, 1H), 4.973(d, J=6.4 Hz, 1H), 7.21~7.54(m, 4H)

Preparation Example 74

Preparation of 1-(2-chlorophenyl)-(S,S)-1,2-(Bis-trimethylsilanyloxy)butane

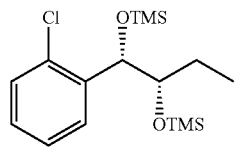

The substantially same method as described in Preparation Example 69 was conducted, except that 1-(2-chlorophenyl)-(S,S)-1,2-butanediol (Preparation example 17) was used instead of 1-(2-chlorophenyl)-(S,S)-1,2-propanediol (Preparation example 14) to obtain the title compound (3.6 g, yield 90~120%).
$^1$H NMR(400 MHz, CDCl$_3$)δ-0.053(s, 9H), 0.044(s, 9H), 1.01(t, J=7.4 Hz, 3H), 1.52~1.65(m, 2H), 3.69~3.75(m, 1H), 5.05(t, J=5.0 Hz, 1H), 7.23~7.54(m, 4H)

Preparation Example 75

Preparation of 1-(2-chlorophenyl)-(R,R)-1,2-(Bis-trimethylsilanyloxy)butane

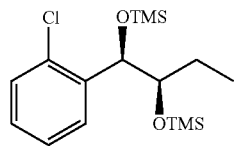

The substantially same method as described in Preparation Example 69 was conducted, except that 1-(2-chlorophenyl)-(R,R)-1,2-butanediol (Preparation example 18) was used instead of 1-(2-chlorophenyl)-(S,S)-1,2-propanediol (Preparation example 14) to obtain the title compound (3.5 g, yield 90~120%).
$^1$H NMR(400 MHz, CDCl$_3$)δ-0.053(s, 9H), 0.044(s, 9H), 1.01(t, J=7.4 Hz, 3H), 1.52~1.65(m, 2H), 3.69~3.75(m, 1H), 5.05(t, J=5.0 Hz, 1H), 7.23~7.54(m, 4H)

Preparation Example 76

Preparation of 1-(2-chlorophenyl)-1,2-(Bis-trimethylsilanyloxy)butane

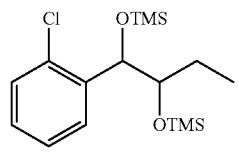

The substantially same method as described in Preparation Example 69 was conducted, except that 1-(2-chlorophenyl)-1,2-butanediol (Preparation example 19) was used instead of 1-(2-chlorophenyl)-(S,S)-1,2-propanediol (Preparation example 14) to obtain the title compound (3.0 g, yield 90~120%).
$^1$H NMR(400 MHz, CDCl$_3$)δ-0.053(s, 9H), 0.044(s, 9H), 1.01(t, J=7.4 Hz, 3H), 1.52~1.65(m, 2H), 3.69~3.75(m, 1H), 5.05(t, J=5.0 Hz, 1H), 7.23~7.54(m, 4H)

Preparation Example 77

Preparation of 1-(2-chlorophenyl)-3-methyl-(S,S)-1,2-(Bis-trimethylsilanyloxy)-butane

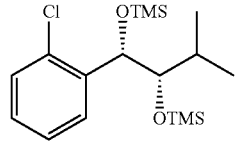

The substantially same method as described in Preparation Example 69 was conducted, except that 1-(2-chlorophenyl)-3-methyl-(S,S)-1,2-butanediol (Preparation example 20) was used instead of 1-(2-chlorophenyl)-(S,S)-1,2-propanediol (Preparation example 14) to obtain the title (2.7 g, yield 90~120%).
$^1$H NMR(400 MHz, CDCl$_3$)δ-0.053(s, 9H), 0.044(s, 9H), 1.07(t, J=7.2 Hz, 6H), 1.83~1.89(m, 1H), 3.53~3.56(m, 1H), 5.22~5.25(m, 1H), 7.23~7.55(m, 4H)

Preparation Example 78

Preparation of 1-(2-chlorophenyl)-3-methyl-(R,R)-1,2-(Bis-trimethylsilanyloxy)-butane

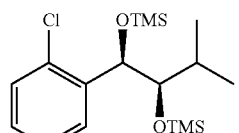

The substantially same method as described in Preparation Example 69 was conducted, except that 1-(2-chlorophenyl)-3-methyl-(R,R)-1,2-butanediol (Preparation example 21) was used instead of 1-(2-chlorophenyl)-(S,S)-1,2-propanediol (Preparation example 14) to obtain the title compound (2.4 g, yield 90~120%).

$^1$H NMR(400 MHz, CDCl$_3$)δ-0.053(s, 9H), 0.044(s, 9H), 1.07(t, J=7.2 Hz, 6H), 1.83~1.89(m, 1H), 3.53~3.56(m, 1H), 5.22~5.25(m, 1H), 7.23~7.55(m, 4H)

Preparation Example 79

Preparation of 1-(2-chlorophenyl)-3-methyl-1,2-(Bis-trimethylsilanyloxy)-butane

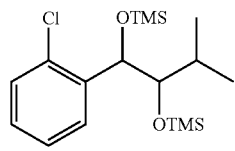

The substantially same method as described in Preparation Example 69 was conducted, except that 1-(2-chlorophenyl)-3-methyl-1,2-butanediol (Preparation example 22) was used instead of 1-(2-chlorophenyl)-(S,S)-1,2-propanediol (Preparation example 14) to obtain the title compound (2.8 g, yield 90~120%).

$^1$H NMR(400 MHz, CDCl$_3$)δ-0.053(s, 9H), 0.044(s, 9H), 1.07(t, J=7.2 Hz, 6H), 1.83~1.89(m, 1H), 3.53~3.56(m, 1H), 5.22~5.25(m, 1H), 7.23~7.55(m, 4H)

Preparation Example 80

Preparation of 1-(2-chlorophenyl)-(S,S)-1,2-(Bis-trimethylsilanyloxy)-hexane

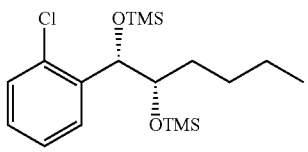

The substantially same method as described in Preparation Example 69 was conducted, except that 1-(2-chlorophenyl)-(S,S)-1,2-hexanediol (Preparation example 23) was used instead of 1-(2-chlorophenyl)-(S,S)-1,2-propanediol (Preparation example 14) to obtain the title compound (3.1 g, yield 90~120%).

$^1$H NMR(400 MHz, CDCl$_3$)δ-0.053(s, 9H), 0.044(s, 9H), 0.90(t, J=7.2 Hz, 3H), 1.35~1.65(m, 6H), 3.78~3.83(m, 1H), 5.04(t, J=5.0 Hz, 1H), 7.23~7.53(m, 4H)

Preparation Example 81

Preparation of 1-(2-chlorophenyl)-(S,S)-1,2-(Bis-trimethylsilanyloxy)-hexane

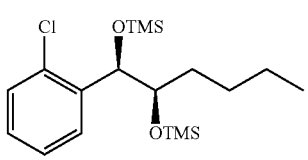

The substantially same method as described in Preparation Example 69 was conducted, except that 1-(2-chlorophenyl)-(R,R)-1,2-hexanediol (Preparation example 24) was used instead of 1-(2-chlorophenyl)-(S,S)-1,2-propanediol (Preparation example 14) to obtain the title compound (3.3 g, yield 90~120%).

$^1$H NMR(400 MHz, CDCl$_3$)δ-0.053(s, 9H), 0.044(s, 9H), 0.90(t, J=7.2 Hz, 3H), 1.35~1.65(m, 6H), 3.78~3.83(m, 1H), 5.04(t, J=5.0 Hz, 1H), 7.23~7.53(m, 4H)

Preparation Example 82

Preparation of 1-(2-chlorophenyl)-(S,S)-1,2-(Bis-trimethylsilanyloxy)-hexane

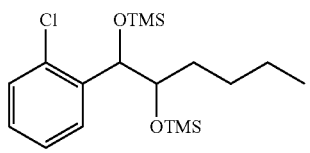

The substantially same method as described in Preparation Example 69 was conducted, except that 1-(2-chlorophenyl)-1,2-hexanediol (Preparation example 25) was used instead of 1-(2-chlorophenyl)-(S,S)-1,2-propanediol (Preparation example 14) to obtain the title compound (3.2 g, yield 90~120%).

$^1$H NMR(400 MHz, CDCl$_3$)δ-0.053(s, 9H), 0.044(s, 9H), 0.90(t, J=7.2 Hz, 3H), 1.35~1.65(m, 6H), 3.78~3.83(m, 1H), 5.04(t, J=5.0 Hz, 1H), 7.23~7.53(m, 4H)

Preparation Example 83

Preparation of 1-(2,4-dichlorophenyl)-(S,S)-1,2-(Bis-trimethylsilanyloxy)-propane

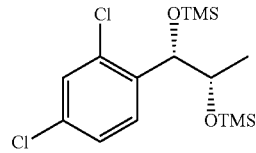

The substantially same method as described in Preparation Example 69 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14) to obtain the title compound (2.4 g, yield 90~120%).

$^1$H NMR(400 MHz, CDCl$_3$)δ-0.053(s, 9H), 0.044(s, 9H), 1.22(d, J=6.4 Hz, 3H), 3.90~3.95(m, 1H), 4.94(t, J=5.0 Hz, 1H), 7.31(dd, J=2.0 Hz, J=8.0 Hz, 1H), 7.40(d, J=2.0 Hz, 1H), 7.49(d, J=8.4 Hz, 1H)

Preparation Example 84

Preparation of 1-(2,6-dichlorophenyl)-(S,S)-1,2-(Bis-trimethylsilanyloxy)-propane

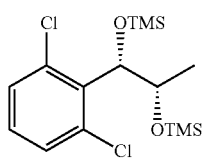

The substantially same method as described in Preparation Example 69 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14) to obtain the title compound (3.4 g, yield 90~120%).

$^1$H NMR(400 MHz, CDCl$_3$)δ-0.053(s, 9H), 0.044(s, 9H), 1.10(d, J=6.4 Hz, 3H), 4.47~4.54(m, 1H), 5.24(t, J=8.8 Hz, 1H), 7.13~7.36(m, 3H)

Preparation Example 85

Preparation of 1-(2,3-dichlorophenyl)-(S,S)-1,2-(Bis-trimethylsilanyloxy)-propane

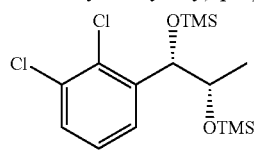

The substantially same method as described in Preparation Example 69 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14) to obtain the title compound (2.2 g, yield 90~120%).

$^1$H NMR(400 MHz, CDCl$_3$)δ-0.053(s, 9H), 0.044(s, 9H), 1.10(d, J=6.4 Hz, 3H,), 4.47~4.54(m, 1H), 5.24(t, J=8.8 Hz, 1H), 7.18~7.22(m, 3H)

Preparation Example 86

Preparation of 1-(2,4-dichlorophenyl)-(S,S)-1,2-(Bis-trimethylsilanyloxy)-butane

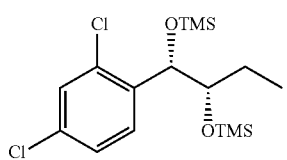

The substantially same method as described in Preparation Example 69 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14) to obtain the title compound (3.1 g, yield 90~120%).

$^1$H NMR(400 MHz, CDCl$_3$)δ-0.053(s, 9H), 0.044(s, 9H), 1.02(t, J=7.4 Hz, 3H), 1.54~1.61(m, 2H), 3.65~3.68(m, 1H), 5.01(t, J=5.0 Hz, 1H), 7.31~7.49(m, 3H)

Preparation Example 87

Preparation of 1-(2,6-dichlorophenyl)-(S,S)-1,2-(Bis-trimethylsilanyloxy)-butane

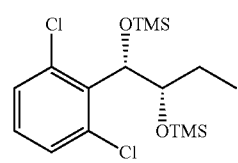

The substantially same method as described in Preparation Example 69 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14) to obtain the title compound (2.8 g, yield 90~120%).

$^1$H NMR(400 MHz, CDCl$_3$)δ-0.053(s, 9H), 0.044(s, 9H), 0.97(t, J=7.6 Hz, 3H), 1.26~1.53(m, 2H), 4.22~4.26(m, 1H), 5.26(t, J=8.4 Hz, 1H), 7.17~7.35(m, 3H)

Preparation Example 88

Preparation of 1-(2,4-dichlorophenyl)-3-methyl-(S,S)-1,2-(Bis-trimethylsilanyloxy)-butane

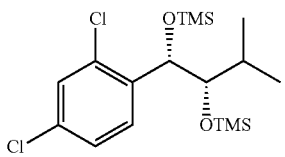

The substantially same method as described in Preparation Example 69 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14) to obtain the title compound (2.7 g, yield 90~120%).

$^1$H NMR(400 MHz, CDCl$_3$)δ-0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.30~7.53(m, 3H)

Preparation Example 89

Preparation of 1-(2,6-dichlorophenyl)-3-methyl-(S,S)-1,2-(Bis-trimethylsilanyloxy)-butane

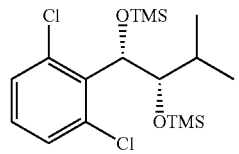

The substantially same method as described in Preparation Example 69 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14) to obtain the title compound (3.3 g, yield 90~120%).

$^1$H NMR(400 MHz, CDCl$_3$)δ-0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.17~7.35(m, 3H)

Preparation Example 90

Preparation of 1-(2,4-dichlorophenyl)-(S,S)-1,2-(Bis-trimethylsilanyloxy)-hexane

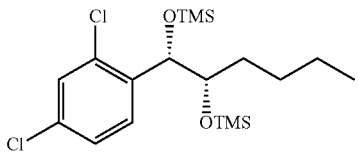

The substantially same method as described in Preparation Example 69 was conducted, except that 1-(2,4-dichlorophenyl)-(S,S)-1,2-hexanediol (Preparation example 90) was used instead of 1-(2-chlorophenyl)-(S,S)-1,2-propanediol (Preparation example 14) to obtain the title compound (3.6 g, yield 90~120%).

$^1$H NMR(400 MHz, CDCl$_3$)δ-0.053(s, 9H), 0.044(s, 9H), 0.89~0.93(m, 3H), 1.30~1.39(m, 2H), 1.49~1.52(m, 2H), 1.56~1.6(m, 2H), 3.72~3.77(m, 1H), 4.98(t, J=4.8 Hz, 1H), 7.28~7.50(m, 3H)

Preparation Example 91

Preparation of 1-(2,6-dichlorophenyl)-(S,S)-1,2-(Bis-trimethylsilanyloxy)-hexane

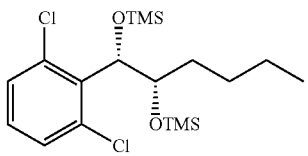

The substantially same method as described in Preparation Example 69 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14) to obtain the title compound (2.8 g, yield 90~120%).

$^1$H NMR(400 MHz, CDCl$_3$)δ-0.053(s, 9H), 0.044(s, 9H), 0.85(t, J=6.7 Hz, 3H), 1.20~1.31(m, 4H), 1.45~1.53(m, 2H), 4.28~4.33(m, 1H), 5.25(t, J=8.4 Hz, 1H), 7.18~7.35(m, 3H)

Preparation Example 92

Preparation of 1-(2,4-dichlorophenyl)-(R,R)-1,2-(Bis-trimethylsilanyloxy)-propane

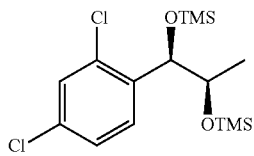

The substantially same method as described in Preparation Example 69 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14) to obtain the title compound (2.2 g, yield 90~120%).

$^1$H NMR(400 MHz, CDCl$_3$)δ-0.053(s, 9H), 0.044(s, 9H), 1.22(d, J=6.4 Hz, 3H), 3.90~3.95(m, 1H), 4.94(t, J=5.0 Hz, 1H), 7.31~7.49(m, 3H)

Preparation Example 93

Preparation of 1-(2,6-dichlorophenyl)-(R,R)-1,2-(Bis-trimethylsilanyloxy)-propane

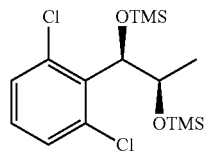

The substantially same method as described in Preparation Example 69 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14) to obtain the title compound (2.6 g, yield 90~120%).

$^1$H NMR(400 MHz, CDCl$_3$)δ-0.053(s, 9H), 0.044(s, 9H), 1.10(d, J=6.4 Hz, 3H), 4.47~4.54(m, 1H), 5.24(t, J=8.8 Hz, 1H), 7.18~7.36(m, 3H)

Preparation Example 94

Preparation of 1-(2,3-dichlorophenyl)-(R,R)-1,2-(Bis-trimethylsilanyloxy)-propane

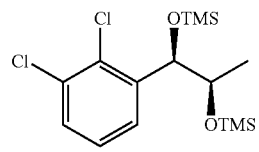

The substantially same method as described in Preparation Example 69 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14) to obtain the title compound (2.9 g, yield 90~120%).

$^1$H NMR(400 MHz, CDCl$_3$)δ-0.053(s, 9H), 0.044(s, 9H), 1.10(d, J=6.4 Hz, 3H), 4.47~4.54(m, 1H), 5.24(t, J=8.8 Hz, 1H), 7.18~7.22(m, 3H)

Preparation Example 95

Preparation of 1-(2,4-dichlorophenyl)-(R,R)-1,2-(Bis-trimethylsilanyloxy)-butane

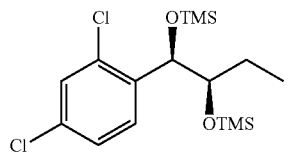

The substantially same method as described in Preparation Example 69 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14) to obtain the title compound (3.6 g, yield 90~120%).

$^1$H NMR(400 MHz, CDCl$_3$)δ-0.053(s, 9H), 0.044(s, 9H), 1.02(t, J=7.4 Hz, 3H), 1.54~1.61(m, 2H), 3.65~3.68(m, 1H), 5.01(t, J=5.0 Hz, 1H), 7.31~7.49(m, 3H)

Preparation Example 96

Preparation of 1-(2,6-dichlorophenyl)-(R,R)-1,2-(Bis-trimethylsilanyloxy)-butane

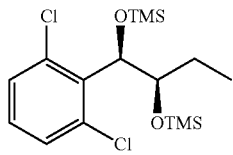

The substantially same method as described in Preparation Example 69 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14) to obtain the title compound (3.3 g, yield 90~120%).

$^1$H NMR(400 MHz, CDCl$_3$)δ-0.053(s, 9H), 0.044(s, 9H), 0.97(t, J=7.6 Hz, 3H), 1.26~1.53(m, 2H), 4.22~4.26(m, 1H), 5.26(t, J=8.4 Hz, 1H), 7.17~7.35(m, 3H)

Preparation Example 97

Preparation of 1-(2,4-dichlorophenyl)-3-methyl-(R,R)-1,2-(Bis-trimethylsilanyloxy)-butane

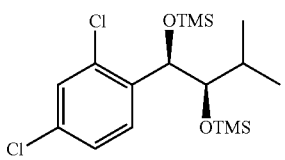

The substantially same method as described in Preparation Example 69 was conducted, except that 1-(2,4-dichlorophenyl)-3-methyl-(R,R)-1,2-butanediol (Preparation example 33) was used instead of 1-(2-chlorophenyl)-(S,S)-1,2-propanediol (Preparation example 14) to obtain the title compound (3.5 g, yield 90~120%).

$^1$H NMR(400 MHz, CDCl$_3$)δ-0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.30~7.53(m, 3H)

Preparation Example 98

Preparation of 1-(2,6-dichlorophenyl)-3-methyl-(R,R)-1,2-(Bis-trimethylsilanyloxy)-butane

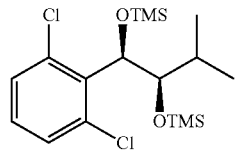

The substantially same method as described in Preparation Example 69 was conducted, except that 1-(2,6-dichlorophenyl)-3-methyl-(R,R)-1,2-butanediol (Preparation example 45) was used instead of 1-(2-chlorophenyl)-(S,S)-1,2-propanediol (Preparation example 14) to obtain the title compound (3.4 g, yield 90~120%).

$^1$H NMR(400 MHz, CDCl$_3$)δ-0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.17~7.35(m, 3H)

Preparation Example 99

Preparation of 1-(2,4-dichlorophenyl)-(R,R)-1,2-(Bis-trimethylsilanyloxy)-hexane

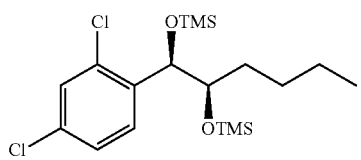

The substantially same method as described in Preparation Example 69 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14) to obtain the title compound (3.6 g, yield 90~120%).

$^1$H NMR(400 MHz, CDCl$_3$)δ-0.053(s, 9H), 0.044(s, 9H), 0.89~0.93(m, 3H), 1.30~1.39(m, 2H), 1.49~1.52(m, 2H), 1.56~1.62(m, 2H), 3.72~3.77(m, 1H), 4.98(t, J=4.8 Hz, 1H), 7.28~7.50(m, 3H)

Preparation Example 100

Preparation of 1-(2,6-dichlorophenyl)-(R,R)-1,2-(Bis-trimethylsilanyloxy)-hexane

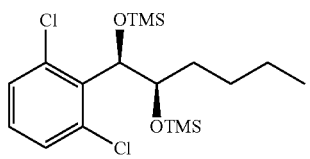

The substantially same method as described in Preparation Example 69 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14) to obtain the title compound (3.3 g, yield 90~120%).

¹H NMR(400 MHz, CDCl₃)δ-0.053(s, 9H), 0.044(s, 9H), 0.85(t, J=6.7 Hz, 3H), 1.20~1.31(m, 4H), 1.45~1.53(m, 2H), 4.28~4.33(m, 1H), 5.25(t, J=8.4 Hz, 1H), 7.18~7.35(m, 3H)

Preparation Example 101

Preparation of 1-(2,4-dichlorophenyl)-1,2-(Bis-trimethylsilanyloxy)-propane

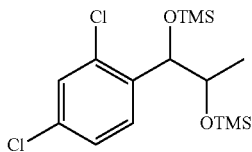

The substantially same method as described in Preparation Example 69 was conducted, except that 1-(2,4-dichlorophenyl)-1,2-propanediol (Preparation example 28) was used instead of 1-(2-chlorophenyl)-(S,S)-1,2-propanediol (Preparation example 14) to obtain the title compound (2.6 g, yield 90~120%).

¹H NMR(400 MHz, CDCl₃)δ-0.053(s, 9H), 0.044(s, 9H), 1.22(d, J=6.4 Hz, 3H), 3.90~3.95(m, 1H), 4.94(t, J=5.0 Hz, 1H), 7.31~7.49(m, 3H)

Preparation Example 102

Preparation of 1-(2,6-dichlorophenyl)-1,2-(Bis-trimethylsilanyloxy)-propane

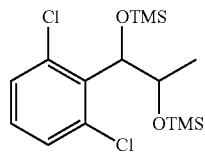

The substantially same method as described in Preparation Example 69 was conducted, except that 1-(2,6-dichlorophenyl)-1,2-propanediol (Preparation example 40) was used instead of 1-(2-chlorophenyl)-(S,S)-1,2-propanediol (Preparation example 14) to obtain the title compound (3.1 g, yield 90~120%).

¹H NMR(400 MHz, CDCl₃)δ-0.053(s, 9H), 0.044(s, 9H), 1.10(d, J=6.4 Hz, 3H), 4.47~4.54(m, 1H), 5.24(t, J=8.8 Hz, 1H), 7.18~7.36(m, 3H)

Preparation Example 103

Preparation of 1-(2,3-dichlorophenyl)-1,2-(Bis-trimethylsilanyloxy)-propane

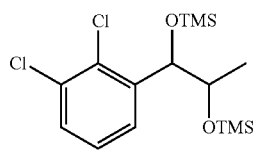

The substantially same method as described in Preparation Example 69 was conducted, except that 1-(2,3-dichlorophenyl)-1,2-propanediol (Preparation example 59) was used instead of 1-(2-chlorophenyl)-(S,S)-1,2-propanediol (Preparation example 14) to obtain the title compound (2.7 g, yield 90~120%).

¹H NMR(400 MHz, CDCl₃)δ-0.053(s, 9H), 0.044(s, 9H), 1.10(d, J=6.4 Hz, 3H), 4.47~4.54(m, 1H), 5.24(t, J=8.8 Hz, 1H), 7.18~7.22(m, 3H)

Preparation Example 104

Preparation of 1-(2,4-dichlorophenyl)-1,2-(Bis-trimethylsilanyloxy)-butane

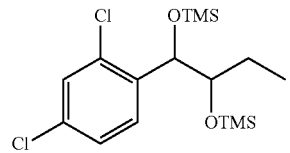

The substantially same method as described in Preparation Example 69 was conducted, except that 1-(2,4-dichlorophenyl)-1,2-butanediol (Preparation example 31) was used instead of 1-(2-chlorophenyl)-(S,S)-1,2-propanediol (Preparation example 14) to obtain the title compound (2.9 g, yield 90~120%).

¹H NMR(400 MHz, CDCl₃)δ-0.053(s, 9H), 0.044(s, 9H), 1.02(t, J=7.4 Hz, 3H), 1.54~1.61(m, 2H), 3.65~3.68(m, 1H), 5.01(t, J=5.0 Hz, 1H), 7.31~7.49(m, 3H)

Preparation Example 105

Preparation of 1-(2,6-dichlorophenyl)-1,2-(Bis-trimethylsilanyloxy)-butane

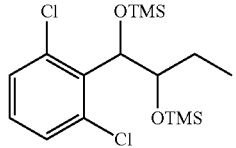

The substantially same method as described in Preparation Example 69 was conducted, except that 1-(2,6-dichlorophenyl)-1,2-butanediol (Preparation example 43) was used instead of 1-(2-chlorophenyl)-(S,S)-1,2-propanediol (Preparation example 14) to obtain the title compound (3.1 g, yield 90~120%).

¹H NMR(400 MHz, CDCl₃)δ-0.053(s, 9H), 0.044(s, 9H), 0.97(t, J=7.6 Hz, 3H), 1.26~1.53(m, 2H), 4.22~4.26(m, 1H), 5.26(t, J=8.4 Hz, 1H), 7.17~7.35(m, 3H)

Preparation Example 106

Preparation of 1-(2,4-dichlorophenyl)-3-methyl-1,2-(Bis-trimethylsilanyloxy)-butane

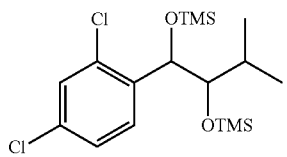

The substantially same method as described in Preparation Example 69 was conducted, except that 1-(2,4-dichlorophenyl)-3-methyl-1,2-butanediol (Preparation example 34) was used instead of 1-(2-chlorophenyl)-(S,S)-1,2-propanediol (Preparation example 14) to obtain the title compound (2.7 g, yield 90~120%).
$^1$H NMR(400 MHz, CDCl$_3$)δ-0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.30~7.53(m, 3H)

Preparation Example 107

Preparation of 1-(2,6-dichlorophenyl)-3-methyl-1,2-(Bis-trimethylsilanyloxy)-butane

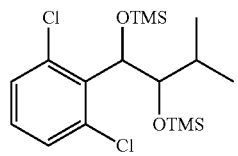

The substantially same method as described in Preparation Example 69 was conducted, except that 1-(2,6-dichlorophenyl)-3-methyl-1,2-butanediol (Preparation example 46) was used instead of 1-(2-chlorophenyl)-(S,S)-1,2-propanediol (Preparation example 14) to obtain the title compound (2.6 g, yield 90~120%).
$^1$H NMR(400 MHz, CDCl$_3$)δ-0.053(s, 9H), 0.044(s, 9H), 1.00(d, J=6.8 Hz, 6H), 1.60~1.65(m, 1H), 4.13~4.18(m, 1H), 5.36(t, J=7.6 Hz, 1H), 7.17~7.35(m, 3H)

Preparation Example 108

Preparation of 1-(2,4-dichlorophenyl)-1,2-(Bis-trimethylsilanyloxy)-hexane

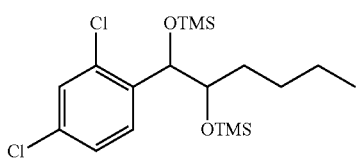

The substantially same method as described in Preparation Example 69 was conducted, except that 1-(2,4-dichlorophenyl)-1,2-hexanediol (Preparation example 37) was used instead of 1-(2-chlorophenyl)-(S,S)-1,2-propanediol (Preparation example 14) to obtain the title compound (3.7 g, yield 90~120%).
$^1$H NMR(400 MHz, CDCl$_3$)δ-0.053(s, 9H), 0.044(s, 9H), 0.89~0.93(m, 3H), 1.30~1.39(m, 2H), 1.49~1.52(m, 2H), 1.56~1.62(m, 2H), 3.72~3.77(m, 1H), 4.98(t, J=4.8 Hz, 1H), 7.28~7.50(m, 3H)

Preparation Example 109

Preparation of 1-(2,6-dichlorophenyl)-1,2-(Bis-trimethylsilanyloxy)-hexane

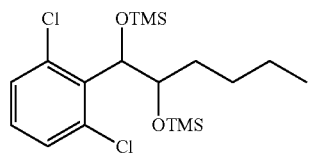

The substantially same method as described in Preparation Example 69 was conducted, except that 1-(2,6-dichlorophenyl)-1,2-hexanediol (Preparation example 49) was used instead of 1-(2-chlorophenyl)-(S,S)-1,2-propanediol (Preparation example 14) to obtain the title compound (3.2 g, yield 90~120%).
$^1$H NMR(400 MHz, CDCl$_3$)δ-0.053(s, 9H), 0.044(s, 9H), 0.85(t, J=6.7 Hz, 3H), 1.20~1.31(m, 4H), 1.45~1.53(m, 2H), 4.28~4.33(m, 1H), 5.25(t, J=8.4 Hz, 1H), 7.18~7.35(m, 3H)

Preparation Example 110

Preparation of 1-(2-fluoroophenyl)-(S,S)-1,2-(Bis-trimethylsilanyloxy)-propane

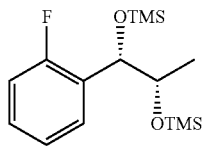

The substantially same method as described in Preparation Example 69 was conducted, except that 1-(2-fluoroophenyl)-(S,S)-1,2-propanediol (Preparation example 61) was used instead of 1-(2-chlorophenyl)-(S,S)-1,2-propanediol (Preparation example 14) to obtain the title compound (2.8 g, yield 90~120%).
$^1$H NMR(400 MHz, CDCl$_3$)δ-0.053(s, 9H), 0.044(s, 9H), 1.15(d, J=6.4 Hz, 3H), 3.90~3.98(m, 1H), 4.78(dd, J=4.4, 7.2 Hz, 1H), 7.04~7.50(m, 4H)

Preparation Example 111

Preparation of 1-(2-fulorophenyl)-(R,R)-1,2-(Bis-trimethylsilanyloxy)-propane

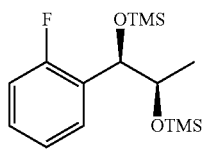

The substantially same method as described in Preparation Example 69 was conducted, except that 1-(2-fluoroophenyl)-(R,R)-1,2-propanediol (Preparation example 62) was used instead of 1-(2-chlorophenyl)-(S,S)-1,2-propanediol (Preparation example 14) to obtain the title compound (2.5 g, yield 90~120%).

¹H NMR(400 MHz, CDCl₃)δ-0.053(s, 9H), 0.044(s, 9H), 1.15(d, J=6.4 Hz, 3H), 3.90~3.98(m, 1H), 4.78(dd, J=4.4, 7.2 Hz, 1H), 7.04~7.50(m, 4H)

Preparation Example 112

Preparation of 1-(2-iodophenyl)-(S,S)-1,2-(Bis-trimethylsilanyloxy)-propane

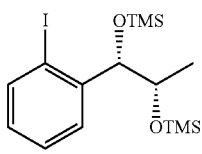

The substantially same method as described in Preparation Example 69 was conducted, except that 1-(2-iodophenyl)-(S,S)-1,2-propanediol (Preparation example 66) was used instead of 1-(2-chlorophenyl)-(S,S)-1,2-propanediol (Preparation example 14) to obtain the title compound (3.1 g, yield 90~120%).

¹H NMR(400 MHz, CDCl₃)δ-0.053(s, 9H), 0.044(s, 9H), 1.27(d, J=6.4 Hz, 3H), 3.99(t, J=6.0 Hz, 1H), 4.81(d, J=4.0 Hz, 1H), 7.01~7.87(m, 4H)

Preparation Example 113

Preparation of 1-(2-iodophenyl)-(R,R)-1,2-(Bis-trimethylsilanyloxy)-propane

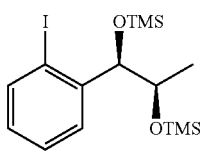

The substantially same method as described in Preparation Example 69 was conducted, except that 1-(2-iodophenyl)-(R,R)-1,2-propanediol (Preparation example 67) was used instead of 1-(2-chlorophenyl)-(S,S)-1,2-propanediol (Preparation example 14) to obtain the title compound (2.8 g, yield 90~120%).

¹H NMR(400 MHz, CDCl₃)δ-0.053(s, 9H), 0.044(s, 9H), 1.26(d, J=6.4 Hz, 3H), 3.98(t, J=6.2 Hz, 1H), 4.88(d, J=4.4 Hz, 1H), 7.00~7.87(m, 4H)

Preparation Example 114

Preparation of 1-(2-iodophenyl)-(S,S)-1,2-(Bis-trimethylsilanyloxy)-butane

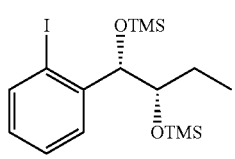

The substantially same method as described in Preparation Example 69 was conducted, except that 1-(2-iodophenyl)-(S,S)-1,2-butanediol (Preparation example 68) was used instead of 1-(2-chlorophenyl)-(S,S)-1,2-propanediol (Preparation example 14) to obtain the title compound (3.3 g, yield 90~120%).

¹H NMR(400 MHz, CDCl₃)δ-0.053(s, 9H), 0.044(s, 9H), 1.04(t, J=7.6 Hz, 3H), 1.60~1.71(m, 2H), 3.71~3.76(m, 1H), 4.87(d, J=4.8 Hz, 1H), 7.01~7.87(m, 4H)

Example 1

Preparation of 1-(2-chlorophenyl)-(S)-1-hydroxypropyl-(S)-2-carbamate (1)

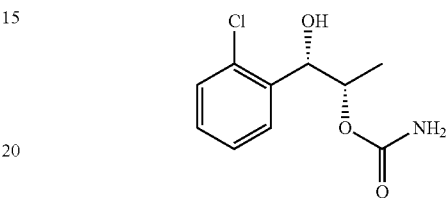

To a stirred solution of crude 1-(2-chlorophenyl)-(S,S)-1,2-(Bis-trimethylsilanyloxy)propane (preparation example 69, 104 g, 0.31 mol) in toluene (670 mL) was added by Chlorosulfonyl isocynate (62.5 mL, 0.71 mol) at 0° C. The reaction mixture was stirred for 2 hr. The reaction mixture was quenched with ice water and then was stirred by additional cold H₂O (500 mL) for 2 hr. After separation of organic layer, the aqueous was adjusted pH2~3 with sat. NaHCO₃ (400 mL) and extracted with EtOAc (300 mL x3). The EtOAc layer was washed with sat. NaHCO₃ (500 mL) and H₂O (500 mL). The organic phase was treated with Charcol for 1.5 hr. The organic phase was filtered with Cellite, dreid over MgSO₄. Filterion and concentration under vacuum provided the title compound of white solid (yield 85% (71.1 g), ee=99.9% MP=83~84° C., [α]_D=+57.8(c=0.25, MeOH))

¹H NMR(400 MHz, CDCl₃) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

¹³C NMR(100 MHz, CDCl₃) δ16.4, 73.1, 75.0, 127.0, 128.4, 129.1, 129.5, 132.7, 138.0, 156.6

Example 2

Preparation of 1-(2-chlorophenyl)-(R)-1-hydroxypropyl-(R)-2-carbamate (2)

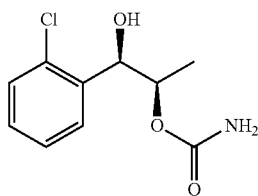

The substantially same method as described in Example 1 was conducted, except that 1-(2-chlorophenyl)-(R,R)-1,2-(Bis-trimethylsilanyloxy) propane (Preparation example 70) was used instead of 1-(2-chlorophenyl)-(S,S)-1,2-(Bis-trimethylsilanyloxy)propane (Preparation example 69) to obtain the title compound (5.7 g, yield 60~90%).

¹H NMR(400 MHz, CDCl₃) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 3

Preparation of 1-(2-chlorophenyl)-1-hydroxypropyl-2-carbamate (3)

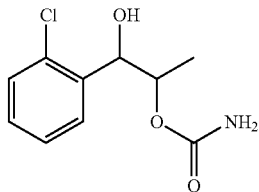

The substantially same method as described in Example 1 was conducted, except that 1-(2-chlorophenyl)-1,2-(Bis-trimethylsilanyloxy)propane (Preparation example 71) was used instead of 1-(2-chlorophenyl)-(S,S)-1,2-(Bis-trimethylsilanyloxy)propane (Preparation example 69) to obtain the title compound (3.8 g, yield 60~90%).

$^1$H NMR(400 MHz, CDCl$_3$) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 4

Preparation of 1-(2-chlorophenyl)-(S)-1-hydroxypropyl-(R)-2-carbamate (4)

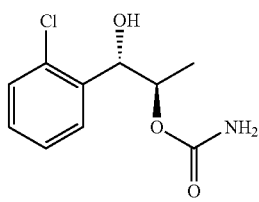

The substantially same method as described in Example 1 was conducted, except that 1-(2-chlorophenyl)-(S,R)-1,2-(Bis-trimethylsilanyloxy) propane (Preparation example 72) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR(400 MHz, CDCl$_3$) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 5

Preparation of 1-(2-chlorophenyl)-(R)-1-hydroxypropyl-(S)-2-carbamate (5)

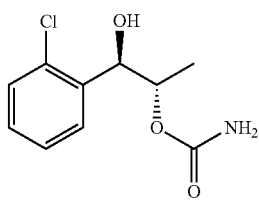

The substantially same method as described in Example 1 was conducted, except that 1-(2-chlorophenyl)-(R,S)-1,2-(Bis-trimethylsilanyloxy) propane (Preparation example 73) was used instead of 1-(2-chlorophenyl)-(S,S)-1,2-(Bis-trimethylsilanyloxy)propane (Preparation example 69) to obtain the title compound (2.3 g, yield 60~90%).

$^1$H NMR(400 MHz, CDCl$_3$) δ1.24(d, J=6.4, 3H), 2.91(d, J=4.8, 1H), 4.68(br s, 2H), 5.06~5.09(m, 1H), 5.18~5.21(m, 1H), 7.23~7.39(m, 3H), 7.55(dd, J=1.6, J=7.8, 1H)

Example 6

Preparation of 1-(2-chlorophenyl)-(S)-1-hydroxybutyl-(S)-2-carbamate (6)

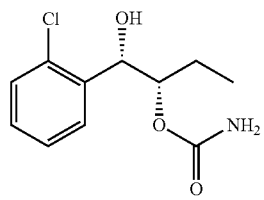 [SMILES: CC[C@H](OC(N)=O)[C@@H](O)c1ccccc1Cl]

The substantially same method as described in Example 1 was conducted, except that 1-(2-chlorophenyl)-(S,S)-1,2-(Bis-trimethylsilanyloxy)butane (Preparation example 74) was used instead of 1-(2-chlorophenyl)-(S,S)-1,2-(Bis-trimethylsilanyloxy)propane (Preparation example 69) to obtain the title compound (2.6 g, yield 60~90%).

$^1$H NMR(400 MHz, CDCl$_3$) δ0.96(t, J=7.4 Hz, 3H), 1.57~1.73(m, 2H), 3.01(d, J=5.6 Hz, 1H), 4.74(br s, 2H), 4.95(dt, J=7.2, 8.8 Hz, 1H), 5.23(t, J=5.6 Hz, 1H), 7.22~7.54 (m, 4H)

Example 7

Synthesis of 1-(2-chlorophenyl)-(R)-1-hydroxybtyl-(R)-2-carbamate (7)

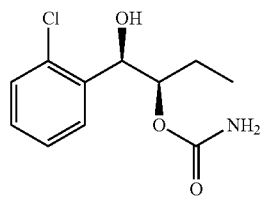 [SMILES: CC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)butane (Preparation Example 75) was used instead of 1-(2-chlorophenyl)-(S,S)-1,2-(Bis-trimethylsilanyloxy)propane (Preparation example 69) to obtain the title compound (2.5 g, yield 60~90%).

$^1$H NMR(400 MHz, CDCl$_3$) δ 0.94(t, J=7.4 Hz, 3H), 1.53~1.73(m, 2H), 2.92(s, 1H), 4.78(br s, 2H), 4.91~4.96(m, 1H), 5.22(d, J=5.5 Hz, 1H), 7.20~7.54(m, 4H)

Example 8

Synthesis of 1-(2-chlorophenyl)-1-hydroxybutyl-2-carbamate (8)

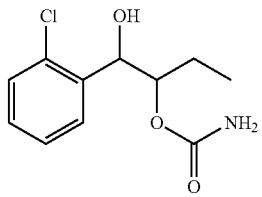 [SMILES: CCC(OC(N)=O)C(O)c1ccccc1Cl]

The substantially same method as described in Example 1 was conducted, except that 1-(2-chlorophenyl)-1,2-(Bis-trimethylsilanyloxy)butane (Preparation Example 76) was used instead of 1-(2-chlorophenyl)-(S,S)-1,2-(Bis-trimethylsilanyloxy)propane (Preparation example 69) to obtain the title compound (1.9 g, yield 60~90%).

$^1$H NMR(400 MHz, CDCl$_3$) δ 0.97(t, J=7 Hz, 3H), 1.58~1.74(m, 2H), 2.94(d, J=6 Hz, 1H), 4.69(br s, 2H), 4.94~4.99(m, 1H), 5.24(t, J=6 Hz, 1H), 7.23~7.56(m, 4H)

Example 9

Synthesis of 1-(2-chlorophenyl)-(S)-1-hydroxy-3-methyl-butyl-(S)-2-carbamate (9)

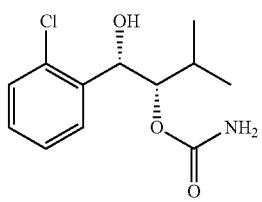 [SMILES: CC(C)[C@H](OC(N)=O)[C@@H](O)c1ccccc1Cl]

The substantially same method as described in Example 1 was conducted, except that 1-(2-chlorophenyl)-3-methyl-(S,S)-1,2-(Bis-trimethylsilanyloxy)butane (Preparation Example 77) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR(400 MHz, CDCl$_3$) δ1.01(d, J=6.4 Hz, 3H), 1.09 (d, J=6.8 Hz, 3H), 2.06(m, 1H), 2.75(d, J=6.8 Hz, 1H), 4.58 (br s, 2H), 4.85~4.88(m, 1H), 5.34~5.37(m, 1H), 7.22~7.33 (m, 2H), 7.35~7.37(m, 1H), 7.51~7.53(m, 1H)

Example 10

Synthesis of 1-(2-chlorophenyl)-(R)-1-hydroxy-3-methyl-butyl-(R)-2-carbamate (10)

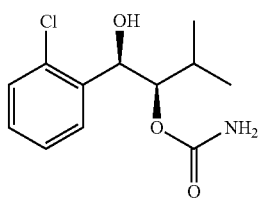 [SMILES: CC(C)[C@@H](OC(N)=O)[C@H](O)c1ccccc1Cl]

The substantially same method as described in Example 1 was conducted, except that 1-(2-chlorophenyl)-3-methyl-(R,R)-1,2-(Bis-trimethylsilanyloxy)butane (Preparation Example 78) was used instead of 1-(2-chlorophenyl)-(S,S)-1,2-(Bis-trimethylsilanyloxy)propane (Preparation example 69) to obtain the title compound (1.6 g, yield 60~90%).

$^1$H NMR(400 MHz, CDCl$_3$) δ1.01(d, J=6.8 Hz, 3H), 1.09 (d, J=6.8 Hz, 3H), 2.06(m, 1H), 2.73(d, J=6.8 Hz, 1H), 4.57 (br s, 2H), 4.85~4.88(m, 1H), 5.34~5.37(m, 1H), 7.24~7.30 (m, 2H), 7.35~7.37(m, 1H), 7.51~7.53(m, 1H)

Example 11

Synthesis of 1-(2-chlorophenyl)-1-hydroxy-3-methyl-butyl-2-carbamate (11)

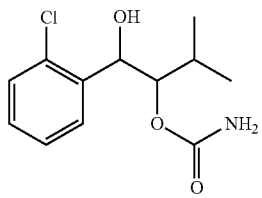 [SMILES: CC(C)C(OC(N)=O)C(O)c1ccccc1Cl]

The substantially same method as described in Example 1 was conducted, except that 1-(2-chlorophenyl)-3-methyl-1,2-(Bis-trimethylsilanyloxy)butane (Preparation Example 79) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR(400 MHz, CDCl$_3$) δ1.00(d, J=6.4 Hz, 3H), 1.09 (d, J=6.4 Hz, 3H), 2.08(m, 1H), 2.76(d, J=6.0 Hz, 1H), 4.59 (br s, 2H), 4.87(dd, J=7.2 Hz, 4.4 Hz, 1H), 5.36(t, J=4.6, 1H), 7.23~7.54(m, 4H)

Example 12

Synthesis of 1-(2-chlorophenyl)-(S)-1-hydroxy-hexyl-(S)-2-carbamate (12)

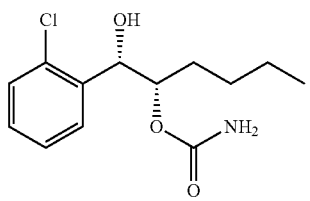 [SMILES: CCCC[C@H](OC(N)=O)[C@@H](O)c1ccccc1Cl]

The substantially same method as described in Example 1 was conducted, except that 1-(2-chlorophenyl)-(S,S)-1,2-(Bis-trimethylsilanyloxy)hexane (Preparation Example 80) was used instead of 1-(2-chlorophenyl)-(S,S)-1,2-(Bis-trimethylsilanyloxy)propane (Preparation example 69) to obtain the title compound (2.3 g, yield 60~90%).

$^1$H NMR(400 MHz, CDCl$_3$) δ0.88(t, J=7 Hz, 3H), 1.33~1.42(m, 4H), 1.53~1.71(m, 2H), 2.89(d, J=5.6 Hz, 1H) 4.64(br s, 2H), 5.04(dt, J=5.0, 9.0 Hz, 1H), 5.20(t, J=5.6 Hz, 1H), 7.23~7.55(m, 4H)

Example 13

Synthesis of 1-(2-chlorophenyl)-(R)-1-hydroxy-hexyl-(R)-2-carbamate (13)

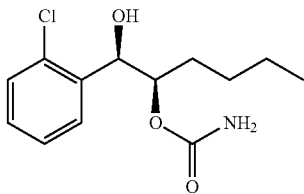 [SMILES: CCCC[C@@H](OC(N)=O)[C@H](O)c1ccccc1Cl]

The substantially same method as described in Example 1 was conducted, except that 1-(2-chlorophenyl)-(R,R)-1,2-(Bis-trimethylsilanyloxy)hexane (Preparation Example 81) was used instead of 1-(2-chlorophenyl)-(S,S)-1,2-(Bis-trimethylsilanyloxy)propane (Preparation example 69) to obtain the title compound (2.2 g, yield 60~90%).

$^1$H NMR(400 MHz, CDCl$_3$) δ 0.89(dd, J=5 Hz, 3H), 1.28~1.43(m, 4H), 1.52~1.58(m, 1H), 1.65~1.72(m, 1H), 2.90(d, J=6 Hz, 1H), 4.64(br s, 2H), 5.01~5.06(m, 1H), 5.22 (t, J=6 Hz, 1H), 7.22~7.56(m, 4H)

Example 14

Synthesis of 1-(2-chlorophenyl)-1-hydroxyhexyl-2-carbamate (14)

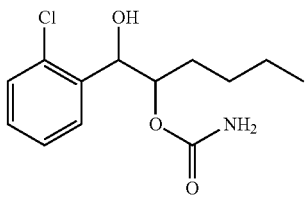 [SMILES: CCCCC(OC(N)=O)C(O)c1ccccc1Cl]

The substantially same method as described in Example 1 was conducted, except that 1-(2-chlorophenyl)-1,2-(Bis-trimethylsilanyloxy)hexane (Preparation Example 82) was used instead of 1-(2-chlorophenyl)-(S,S)-1,2-(Bis-trimethylsilanyloxy)propane (Preparation example 69) to obtain the title compound (2.1 g, yield 60~90%).

$^1$H NMR(400 MHz, CDCl$_3$) δ 0.88(dd, J=5 Hz, 3H), 1.31~1.43(m, 4H), 1.63~1.70(m, 1H), 1.52~1.60(m, 1H), 3.06(d, J=6 Hz, 1H), 4.75(br s, 2H), 5.00~5.05(m, 1H), 5.21 (t, J=6 Hz, 1H), 7.22~7.55(m, 4H)

Example 15

Synthesis of 1-(2-chlorophenyl)-(S)-1-hydroxypropyl-(S)-2-N-methylcarbamate (15)

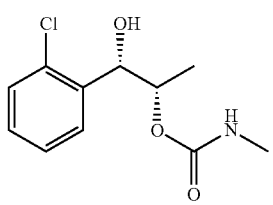 [SMILES: CNC(=O)O[C@@H](C)[C@@H](O)c1ccccc1Cl]

1-(2-chlorophenyl)-(S,S)-1,2-propanediol (2.4 g) obtained in Preparation Example 14, tetrahydrofuran (THF, 12 ml), and carbonyldiimidazole (CDI, 3.12 g) were put into a flask and stirred at the room temperature. After approximately 3 hours, methylamine solution (CH$_3$NH$_2$, 4 ml (33% in EtOH)) was added thereto. When the reaction was completed, the obtained product was washed with 1M HCl solution and ethylacetate (EA). The separated organic layer was dehydrated with anhydrous magnesium sulfate (MgSO$_4$), filtrated, and concented under reduced pressure. The concentrated residue was purified by a silica gel column chromatography, to obtain the title compound (1.6 g, yield 51%).

$^1$H NMR(400 MHz, CDCl$_3$) δ1.03~1.25(m, 3H), 2.76(s, 3H), 3.34(s, 1H), 4.80(br s 1H), 5.04(t, J=12.5 Hz, 1H), 5.14(s, 1H), 7.20~7.53(m, 4H)

Example 16

Synthesis of 1-(2-chlorophenyl)-(S)-1-hydroxypropyl-(S)-2-N-propylcarbamate (16)

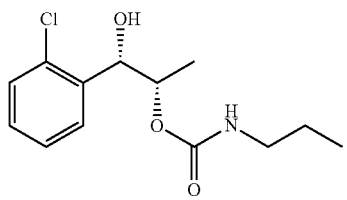 [SMILES: CCCNC(=O)O[C@@H](C)[C@@H](O)c1ccccc1Cl]

The substantially same method as described in Example 15 was conducted, except that propylamine was used instead of methylamine solution (CH$_3$NH$_2$ in EtOH), to obtain the title compound (0.79 g, yield 25%).

$^1$H NMR(400 MHz, CDCl$_3$) δ0.90(t, J=6.8 Hz, 3H), 1.20 (d, J=5.96 Hz, 3H), 1.49(dd, J=14.2 Hz, 2H), 3.11(d, J=6.28 Hz, 2H), 3.34(s, 1H), 4.84(br s, 1H), 5.05(t, J=5.88 Hz, 1H), 5.14(s, 1H), 7.22~7.53(m, 4H)

Example 17

Synthesis of 1-(2-chlorophenyl)-(S)-1-hydroxypropyl-(R)-2-N-isopropylcarbamate (17)

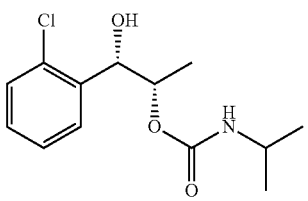 [SMILES: CC(C)NC(=O)O[C@@H](C)[C@@H](O)c1ccccc1Cl]

The substantially same method as described in Example 15 was conducted, except that isopropylamine was used instead of methylamine solution (CH$_3$NH$_2$ in EtOH), to obtain the title compound (1.5 g, yield 41%).

$^1$H NMR(400 MHz, CDCl$_3$) δ1.14(dd, J=6.5 Hz, 6H), 1.19 (d, J=6.4 Hz, 3H), 3.21(s, 1H), 3.73~3.82(m, 1H), 4.59(br s, 1H), 5.01~5.07(m, 1H), 5.14(t, J=5.8 Hz, 1H), 7.20~7.53(m, 4H)

Example 18

Synthesis of 1-(2-chlorophenyl)-(S)-1-hydroxypropyl-(R)-2-N-cyclopropylcarbamate (18)

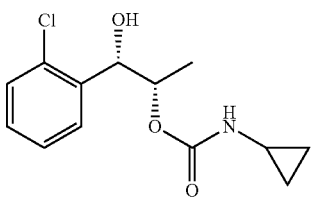

The substantially same method as described in Example 15 was conducted, except that cyclopropylamine was used instead of methylamine solution (CH$_3$NH$_2$ in EtOH), to obtain the title compound (2.2 g, yield 43%).

$^1$H NMR(400 MHz, CDCl$_3$) δ0.50~0.56(m, 2H), 0.74(d, J=7.21 Hz, 2H), 1.25(s, 3H), 2.56~2.61(m, 1H), 3.72(s, 1H), 4.98(br s, 1H), 5.05~5.11(m, 1H), 7.16(s, 1H), 7.23~7.54(m, 4H)

Example 19

Synthesis of 1-(2-chlorophenyl)-(S)-1-hydroxypropyl-(R)-2-N-cyclohexyl carbamate (19)

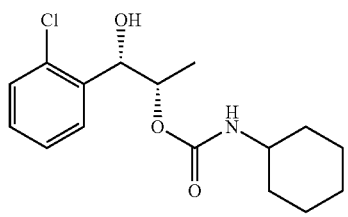 [SMILES: C[C@H](OC(=O)NC1CCCCC1)[C@@H](O)c1ccccc1Cl]

The substantially same method as described in Example 15 was conducted, except that cyclohexylamine was used instead of methylamine solution (CH$_3$NH$_2$ in EtOH), to obtain the title compound (1.1 g, yield 26%).

$^1$H NMR(400 MHz, CDCl$_3$) δ1.06~1.40(m, 7H), 1.56~1.61(m, 2H), 1.69~1.71(m, 2H), 1.87~1.94(m, 2H), 3.19(d, J=4.32 Hz, 1H), 3.45(s, 1H), 4.64(br s 1H), 5.02~5.07(m, 1H), 5.14(t, J=6.08 Hz, 1H) 7.20~7.53(m, 4H)

Example 20

Synthesis of 1-(2-chlorophenyl)-(S)-1-hydroxypropyl-(S)-2-N-benzyl carbamate (20)

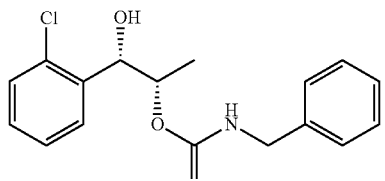

The substantially same method as described in Example 15 was conducted, except that benzylamine was used instead of methylamine solution (CH$_3$NH$_2$ in EtOH), to obtain the title compound (1.2 g, yield 18%).

$^1$H NMR(400 MHz, CDCl$_3$) δ 1.27(d, J=10 Hz, 3H), 3.12 (d, J=5 Hz, 1H), 4.37(d, J=6 Hz, 2H), 5.12~5.19(m, 3H), 7.15~7.56(m, 9H)

Example 21

Synthesis of 1-(2-chlorophenyl)-(S)-1-hydroxypropyl-(S)-2-N-bicyclo[2,2,1]heptanescarbamate (21)

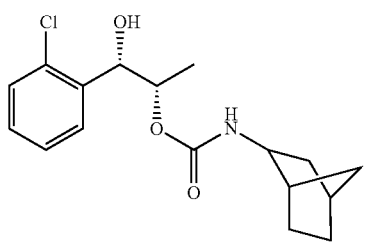 [SMILES: C[C@H](OC(=O)NC1CC2CCC1C2)[C@@H](O)c1ccccc1Cl]

The substantially same method as described in Example 15 was conducted, except that 2-aminonorbornane was used instead of methylamine solution (CH$_3$NH$_2$ in EtOH), to obtain the title compound (1.7 g, yield 32%).

$^1$H NMR(400 MHz, CDCl$_3$) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 22

Synthesis of 1-(2-chlorophenyl)-(R)-1-hydroxypropyl-(R)-2-N-methylcarbamate (22)

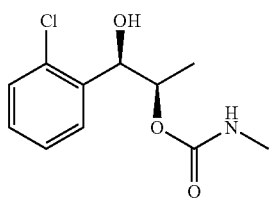 [SMILES: CNC(=O)O[C@H](C)[C@H](O)c1ccccc1Cl]

The substantially same method as described in Example 15 was conducted, except that 1-(2-chlorophenyl)-(R,R)-1,2-propanediol (Preparation example 15) was used instead of 1-(2-chlorophenyl)-(S,S)-1,2-propanediol (Preparation example 14), to obtain the title compound (3.36 g, yield 60%).

$^1$H NMR(400 MHz, CDCl$_3$) δ 1.20(d, J=6.8 Hz, 3H), 2.80 (d, J=4.8 Hz, 3H), 3.20(d, J=4.4 Hz, 1H), 4.75(br s, 1H), 5.03~5.09(m, 1H), 5.14~5.17(m, 1H), 7.22~7.55(m, 4H)

Example 23

Synthesis of 1-(2-chlorophenyl)-(R)-1-hydroxypropyl-(R)-2-N-propylcarbamate (23)

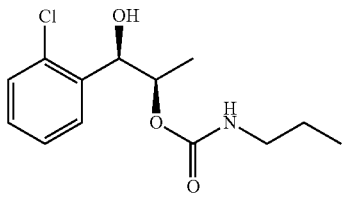 [SMILES: CCCNC(=O)O[C@H](C)[C@H](O)c1ccccc1Cl]

The substantially same method as described in Example 22 was conducted, except that propylamine was used instead of methylamine solution (CH$_3$NH$_2$ in EtOH), to obtain the title compound (3.1 g, yield 53%).

$^1$H NMR(400 MHz, CDCl$_3$) δ0.92(t, J=7.6 Hz, 3H), 1.21 (d, J=6.4 Hz, 3H), 1.51(m, 2H), 3.09~3.14(m, 2H), 3.28(d, J=4.4 Hz, 1H), 4.82(br s, 1H), 5.03~5.09(m, 1H), 5.14~5.17 (m, 1H), 7.22~7.55(m, 4H)

Example 24

Synthesis of 1-(2-chlorophenyl)-(R)-1-hydroxypropyl-(R)-2-N-isopropylcarbamate (24)

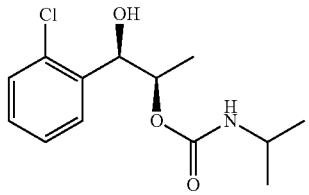 [SMILES: CC(C)NC(=O)O[C@H](C)[C@H](O)c1ccccc1Cl]

The substantially same method as described in Example 22 was conducted, except that isopropylamine was used instead of methylamine solution (CH$_3$NH$_2$ in EtOH), to obtain the title compound (0.16 g, yield 27%).

$^1$H NMR(400 MHz, CDCl$_3$) δ0.88~1.16(m, 6H), 1.19~1.26(m, 3H), 3.34(s, 1H), 3.71~3.78(m, 1H), 4.62(br s, 1H), 5.03(t, J=5.8 Hz, 1H), 5.13(d, J=4.9 Hz, 1H), 7.20~7.53 (m, 4H)

Example 25

Synthesis of 1-(2-chlorophenyl)-(R)-1-hydroxypropyl-(R)-2-N-cyclopropylcarbamate (25)

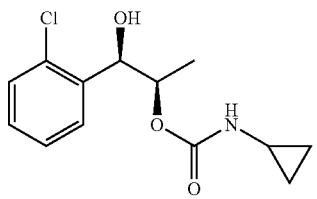 [SMILES: C[C@@H](OC(=O)NC1CC1)[C@H](O)c1ccccc1Cl]

The substantially same method as described in Example 22 was conducted, except that cyclopropylamine was used instead of methylamine solution (CH$_3$NH$_2$ in EtOH), to obtain the title compound (3.7 g, yield 60%).

$^1$H NMR(400 MHz, CDCl$_3$) δ0.49~0.54(m, 2H), 0.74(d, J=7.2 Hz, 2H), 1.22(s, 3H), 2.55~2.60(m, 1H), 3.16(s, 1H), 5.00(s, 1H), 5.04~5.11(m, 1H), 5.16(s, 1H), 7.23~7.54(m, 4H)

Example 26

Synthesis of 1-(2-chlorophenyl)-(R)-1-hydroxypropyl-(R)-2-N-cyclohexyl carbamate (26)

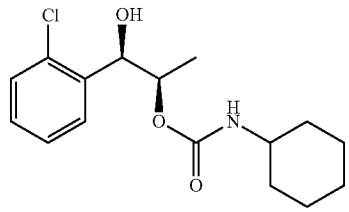 [SMILES: C[C@@H](OC(=O)NC1CCCCC1)[C@H](O)c1ccccc1Cl]

The substantially same method as described in Example 22 was conducted, except that cyclohexylamine was used instead of methylamine solution (CH$_3$NH$_2$ in EtOH), to obtain the title compound (1.9 g, yield 28%).

$^1$H NMR(400 MHz, CDCl$_3$) δ1.05~1.38(m, 8H), 1.58~1.70(m, 3H), 1.85~1.95(m, 2H), 3.39~3.47(m, 1H), 3.56(s, 1H), 4.79(br s, 1H), 5.01~5.07(m, 1H), 5.14(t, J=5.2 Hz, 1H), 7.20~7.54(m, 4H)

Example 27

Synthesis of 1-(2-chlorophenyl)-(R)-1-hydroxypropyl-(R)-2-N-benzylcarbamate (27)

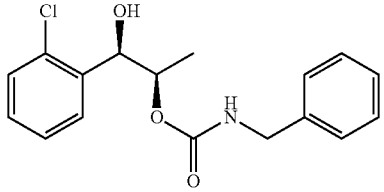 [SMILES: C[C@@H](OC(=O)NCc1ccccc1)[C@H](O)c1ccccc1Cl]

The substantially same method as described in Example 22 was conducted, except that benzylamine was used instead of methylamine solution (CH$_3$NH$_2$ in EtOH), to obtain the title compound (0.52 g, yield 19%).

$^1$H NMR(400 MHz, CDCl$_3$) δ1.25(d, J=6 Hz, 3H), 1.64(s, 1H), 3.13(d, J=4.4 Hz, 1H), 4.37(d, J=5.6 Hz, 2H), 5.12~5.19 (m, 2H), 7.23~7.55(m, 9H)

Example 28

Synthesis of 1-(2-chlorophenyl)-(R)-1-hydroxypropyl-(R)-2-N-bicyclo[2,2,1]heptanecarbamate (28)

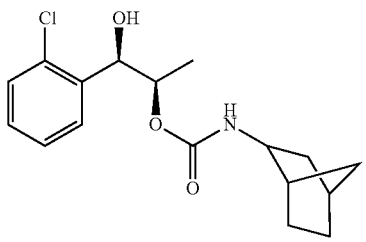 [SMILES: C[C@@H](OC(=O)NC1CC2CCC1C2)[C@H](O)c1ccccc1Cl]

The substantially same method as described in Example 22 was conducted, except that 2-aminonorbornane was used instead of methylamine solution (CH$_3$NH$_2$ in EtOH), to obtain the title compound (1.7 g, yield 20~50%).

$^1$H NMR(400 MHz, CDCl$_3$) δ 1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 29

Synthesis of 1-(2-chlorophenyl)-1-hydroxypropyl-2-N-methylcarbamate (29)

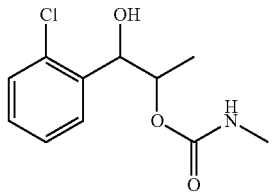 [SMILES: CNC(=O)OC(C)C(O)c1ccccc1Cl]

The substantially same method as described in Example 15 was conducted, except that 1-(2-chlorophenyl)-1,2-propanediol (Preparation example 16) was used instead of 1-(2-chlorophenyl)-(S,S)-1,2-propanediol (Preparation example 14), to obtain the title compound (2.6 g, yield 45%).

$^1$H NMR(400 MHz, CDCl$_3$) δ 1.21(d, J=6 Hz, 3H), 2.81(d, J=5 Hz, 3H), 3.14(d, J=4 Hz, 1H), 4.72(br s, 1H), 5.07(dd, J=6 Hz, 1H), 5.16(t, J=6 Hz, 1H), 7.22~7.56(m, 4H)

Example 30

Synthesis of 1-(2-chlorophenyl)-1-hydroxypropyl-2-N-propylcarbamate (30)

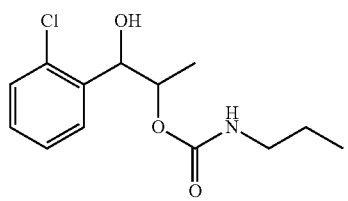 [SMILES: CCCNC(=O)OC(C)C(O)c1ccccc1Cl]

The substantially same method as described in Example 29 was conducted, except that propylamine was used instead of methylamine solution (CH$_3$NH$_2$ in EtOH), to obtain the title compound (1.0 g, yield 17%).

$^1$H NMR(400 MHz, CDCl$_3$) δ 0.92(t, J=7 Hz, 3H), 1.21(d, J=6 Hz, 3H), 1.53(dd, J=7 Hz, 2H), 3.13(dd, J=7 Hz, 2H), 3.28(d, 1H), 4.82(S, 1H), 5.06(dd, J=7 Hz, 1H), 5.16(t, J=5 Hz, 1H), 7.21~7.56(m, 4H)

Example 31

Synthesis of 1-(2-chlorophenyl)-1-hydroxypropyl-2-N-isopropylcarbamate (31)

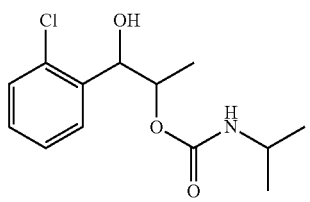 [SMILES: CC(C)NC(=O)OC(C)C(O)c1ccccc1Cl]

The substantially same method as described in Example 29 was conducted, except that isopropylamine was used instead of methylamine solution (CH$_3$NH$_2$ in EtOH), to obtain the title compound (0.54 g, yield 16%).

$^1$H NMR(400 MHz, CDCl$_3$) δ 1.16(dd, J=6 Hz, 6H), 1.21 (d, J=6 Hz, 3H), 3.23(d, J=6 Hz, 1H), 3.75~3.84(m, 1H), 4.61(br s, 1H), 5.06(t, J=6 Hz, 1H), 5.16(t, J=6 Hz, 1H), 7.22~7.56(m, 4H)

Example 32

Synthesis of 1-(2-chlorophenyl)-1-hydroxypropyl-2-N-cyclopropylcarbamate (32)

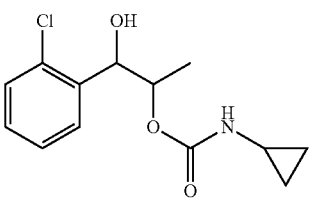 [SMILES: CC(OC(=O)NC1CC1)C(O)c1ccccc1Cl]

The substantially same method as described in Example 29 was conducted, except that cyclopropylamine was used instead of methylamine solution (CH$_3$NH$_2$ in EtOH), to obtain the title compound (1.0 g, yield 17%).

$^1$H NMR(400 MHz, CDCl$_3$) δ 0.50(t, J=6 Hz, 2H), 0.77(t, J=3 Hz, 2H), 1.12(d, J=7 Hz, 3H), 2.53~2.59(m, 1H), 3.22(d, J=4 Hz, 1H), 5.08(dd, J=6 Hz, 1H), 5.15(S, 1H), 7.22~7.55 (m, 4H)

Example 33

Synthesis of 1-(2-chlorophenyl)-1-hydroxypropyl-2-N-cyclohexylcarbamate (33)

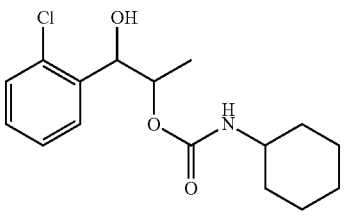

The substantially same method as described in Example 29 was conducted, except that cyclohexylamine was used instead of methylamine solution (CH$_3$NH$_2$ in EtOH), to obtain the title compound (2.2 g, yield 33%).

$^1$H NMR(400 MHz, CDCl$_3$) δ 1.07~1.17(m, 3H), 1.21(d, J=6 Hz, 3H), 1.29~1.42(m, 3H), 1.72(dd, J=6 Hz, 2H), 1.92 (dd, J=6 Hz, 2H), 3.26(d, J=4 Hz, 1H), 3.46(t, J=4 Hz, 1H), 4.68(d, J=6 Hz, 1H), 5.07(dd, J=6 Hz, 1H), 5.16(t, J=6 Hz, 1H), 7.22~7.55(m, 4H)

Example 34

Synthesis of 1-(2-chlorophenyl)-1-hydroxypropyl-2-N-benzylcarbamate (34)

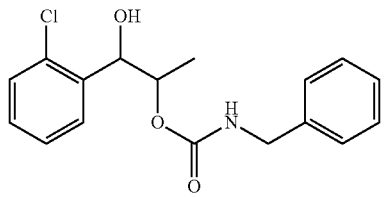 [SMILES: CC(OC(=O)NCc1ccccc1)C(O)c1ccccc1Cl]

The substantially same method as described in Example 29 was conducted, except that benzylamine was used instead of methylamine solution (CH$_3$NH$_2$ in EtOH), to obtain the title compound (1.3 g, yield 19%).

$^1$H NMR(400 MHz, CDCl$_3$) δ 1.25(d, J=6 Hz, 3H), 3.16(d, J=4 Hz, 1H), 4.36(d, J=6 Hz, 2H), 5.14(dd, J=6 Hz, 3H), 7.23~7.56(m, 9H), yield: 19% (1.3 g)

Example 35

Synthesis of 1-(2-chlorophenyl)-1-hydroxypropyl-2-N-bicyclo[2,2,1]heptanecarbamate (35)

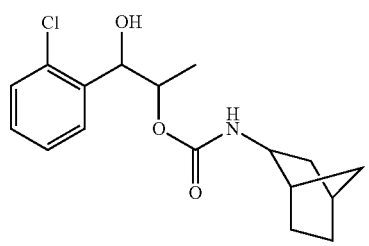 [SMILES: CC(OC(=O)NC1CC2CCC1C2)C(O)c1ccccc1Cl]

The substantially same method as described in Example 29 was conducted, except that 2-aminonorbornane was used instead of methylamine solution (CH$_3$NH$_2$ in EtOH), to obtain the title compound (1.7 g, yield 20~50%).

$^1$H NMR(400 MHz, CDCl$_3$) δ1.08~1.35(m, 9H), 1.65(br s, 1H), 1.75~1.71(m, 1H), 2.14~2.24(m, 1H), 2.27~2.30(m, 1H), 3.23~3.29(m, 1H), 3.47~3.52(m, 1H), 4.67(br s, 1H), 5.01~5.09(m, 1H), 5.12~5.18(m, 1H), 7.22~7.55(m, 4H)

Example 36

Synthesis of 1-(2,4-dichlorophenyl)-(S)-1-hydroxypropyl-(S)-2-carbamate (36)

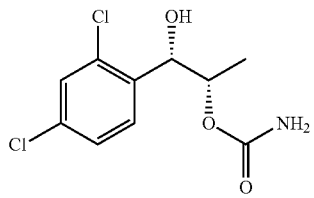 [SMILES: C[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)propane (Preparation Example 83) was used instead of 1-(2-chlorophenyl)-(S,S)-1,2-(Bis-trimethylsilanyloxy)propane (Preparation example 69) to obtain the title compound (1.8 g, yield 60~90%).

$^1$H NMR(400 MHz, CDCl$_3$) δ1.22(d, J=6.4 Hz, 3H), 4.16 (br t, 1H) 4.96(br t, 3H), 5.07(t, J=4.8 Hz, 1H), 7.23~7.52(m, 3H)

Example 37

Synthesis of 1-(2,6-dichlorophenyl)-(S)-1-hydroxypropyl-(S)-2-carbamate (37)

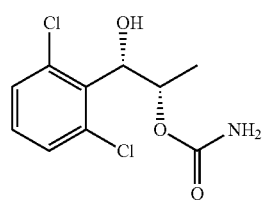 [SMILES: C[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)propane (Preparation Example 84) was used instead of 1-(2-chlorophenyl)-(S,S)-1,2-(Bis-trimethylsilanyloxy)propane (Preparation example 69) to obtain the title compound (2.6 g, yield 60~90%)

Example 38

Synthesis of 1-(2,3-dichlorophenyl)-(S)-1-hydroxypropyl-(S)-2-carbamate (38)

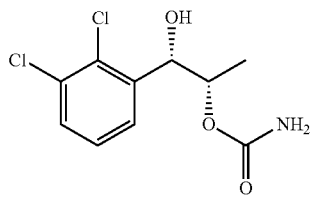 [SMILES: C[C@H](OC(N)=O)[C@@H](O)c1cccc(Cl)c1Cl]

The substantially same method as described in Example 1 was conducted, except that 1-(2,3-dichlorophenyl)-(S,S)-1,2-(Bis-trimethylsilanyloxy)propane (Preparation Example 85) was used instead of 1-(2-chlorophenyl)-(S,S)-1,2-(Bis-trimethylsilanyloxy)propane (Preparation example 69) to obtain the title compound (1.4 g, yield 60~90%)

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 39

Synthesis of 1-(2,4-dichlorophenyl)-(S)-1-hydroxy-butyl-(S)-2-carbamate (39)

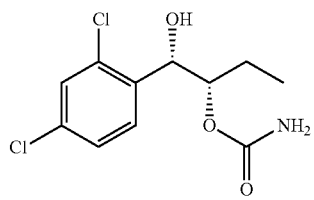 [SMILES: CC[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)butane (Preparation Example 86) was used instead of 1-(2-chlorophenyl)-(S,S)-1,2-(Bis-trimethylsilanyloxy)propane (Preparation example 69) to obtain the title compound (2.3 g, yield 60~90%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 40

Synthesis of 1-(2,6-dichlorophenyl)-(S)-1-hydroxy-butyl-(S)-2-carbamate (40)

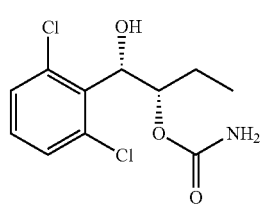 [SMILES: CC[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)butane (Preparation Example 87) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 41

Synthesis of 1-(2,4-dichlorophenyl)-(S)-1-hydroxy-3-methyl-butyl-(S)-2-carbamate (41)

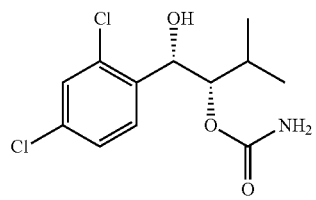 [SMILES: CC(C)[C@H](OC(N)=O)[C@@H](O)c1ccc(Cl)cc1Cl]

The substantially same method as described in Example 1 was conducted, except that 1-(2,4-dichlorophenyl)-3-methyl-(S,S)-1,2-(Bis-trimethylsilanyloxy)butane (Preparation Example 88) was used instead of 1-(2-chlorophenyl)-(S,S)-1,2-(Bis-trimethylsilanyloxy)propane (Preparation example 69) to obtain the title compound (1.9 g, yield 60~90%).

$^1$H NMR(400 MHz, CDCl$_3$) δ1.00(1, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 42

Synthesis of 1-(2,6-dichlorophenyl)-(S)-1-hydroxy-3-methyl-butyl-(S)-2-carbamate (42)

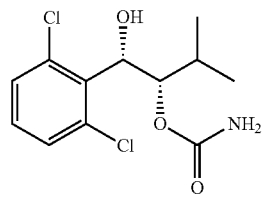 [SMILES: CC(C)[C@H](OC(N)=O)[C@@H](O)c1c(Cl)cccc1Cl]

The substantially same method as described in Example 1 was conducted, except that 1-(2,6-dichlorophenyl)-3-methyl-(S,S)-1,2-(Bis-trimethylsilanyloxy)butane (Preparation Example 89) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR(400 MHz, CDCl$_3$) δ1.00(1, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 43

Synthesis of 1-(2,4-dichlorophenyl)-(S)-1-hydroxy-hexyl-(S)-2-carbamate (43)

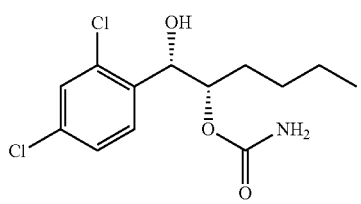 [SMILES: CCCC[C@H](OC(N)=O)[C@@H](O)c1ccc(Cl)cc1Cl]

The substantially same method as described in Example 1 was conducted, except that 1-(2,4-dichlorophenyl)-(S,S)-1,2-(Bis-trimethylsilanyloxy)hexane (Preparation Example 90) was used instead of 1-(2-chlorophenyl)-(S,S)-1,2-(Bis-trimethylsilanyloxy)propane (Preparation example 69) to obtain the title compound (2.2 g, yield 60~90%).

$^{1}$H NMR(400 MHz, CDCl$_{3}$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m 3H)

Example 44

Synthesis of 1-(2,6-dichlorophenyl)-(S)-1-hydroxy-hexyl-(S)-2-carbamate (44)

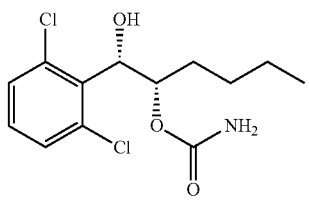 [SMILES: CCCC[C@H](OC(N)=O)[C@@H](O)c1c(Cl)cccc1Cl]

The substantially same method as described in Example 1 was conducted, except that 1-(2,6-dichlorophenyl)-(S,S)-1,2-(Bis-trimethylsilanyloxy)hexane (Preparation Example 91) was used instead of 1-(2-chlorophenyl)-(S,S)-1,2-(Bis-trimethylsilanyloxy)propane (Preparation example 69) to obtain the title compound (2.1 g, yield 60~90%)

$^{1}$H NMR(400 MHz, CDCl$_{3}$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 45

Synthesis of 1-(2,4-dichlorophenyl)-(R)-1-hydroxypropyl-(R)-2-carbamate (45)

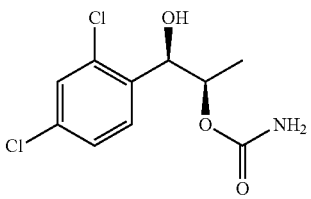 [SMILES: C[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)propane (Preparation Example 92) was used instead of 1-(2-chlorophenyl)-(S,S)-1,2-(Bis-trimethylsilanyloxy)propane (Preparation example 69) to obtain the title compound (1.2 g, yield 60~90%), $^{1}$H NMR(400 MHz, CDCl$_{3}$) δ1.22(d, J=6.4 Hz, 3H), 4.16 (br t, 1H) 4.96(br t, 3H), 5.07(t, J=4.8 Hz, 1H), 7.23~7.52(m, 3H)

Example 46

Synthesis of 1-(2,6-dichlorophenyl)-(R)-1-hydroxypropyl-(R)-2-carbamate (46)

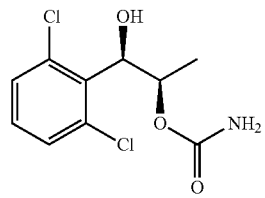 [SMILES: C[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)propane (Preparation Example 93) was used instead of 1-(2-chlorophenyl)-(S,S)-1,2-(Bis-trimethylsilanyloxy)propane (Preparation example 69) to obtain the title compound (1.7 g, yield 60~90%), $^{1}$H NMR(400 MHz, CDCl$_{3}$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H), Example 47

Synthesis of 1-(2,3-dichlorophenyl)-(R)-1-hydroxypropyl-(R)-2-carbamate (47)

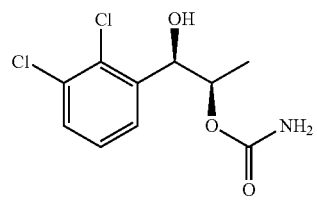 [SMILES: C[C@@H](OC(N)=O)[C@H](O)c1cccc(Cl)c1Cl]

The substantially same method as described in Example 1 was conducted, except that 1-(2,3-dichlorophenyl)-(R,R)-1,2-(Bis-trimethylsilanyloxy)propane (Preparation Example 94) was used instead of 1-(2-chlorophenyl)-(S,S)-1,2-(Bis-trimethylsilanyloxy)propane (Preparation example 69) to obtain the title compound (2.0 g, yield 60~90%)

$^{1}$H NMR(400 MHz, CDCl$_{3}$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 48

Synthesis of 1-(2,4-dichlorophenyl)-(R)-1-hydroxy-butyl-(R)-2-carbamate (48)

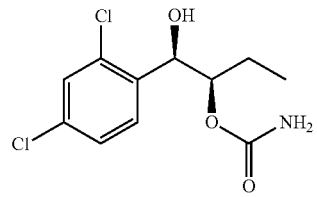 [SMILES: CC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)butane (Preparation Example 95) was used instead of 1-(2-chlorophenyl)-(S,S)-1,2-(Bis-trimethylsilanyloxy)propane (Preparation example 69) to obtain the title compound (2.3 g, yield 60~90%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 49

Synthesis of 1-(2,6-dichlorophenyl)-(R)-1-hydroxy-butyl-(R)-2-carbamate (49)

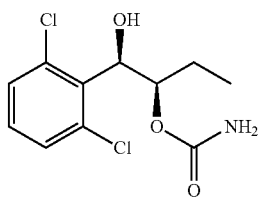 [SMILES: CC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)butane (Preparation Example 96) was used instead of 1-(2-chlorophenyl)-(S,S)-1,2-(Bis-trimethylsilanyloxy)propane (Preparation example 69) to obtain the title compound (2.5 g, yield 60~90%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 50

Synthesis of 1-(2,4-dichlorophenyl)-(R)-1-hydroxy-3-methyl-butyl-(R)-2-carbamate (50)

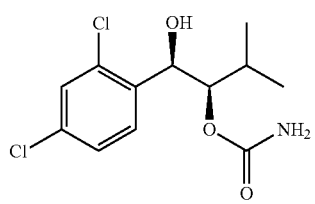 [SMILES: CC(C)[C@@H](OC(N)=O)[C@H](O)c1ccc(Cl)cc1Cl]

The substantially same method as described in Example 1 was conducted, except that 1-(2,4-dichlorophenyl)-3-methyl-(R,R)-1,2-(Bis-trimethylsilanyloxy)butane (Preparation Example 97) was used instead of 1-(2-chlorophenyl)-(S,S)-1,2-(Bis-trimethylsilanyloxy)propane (Preparation example 69) to obtain the title compound (2.8 g, yield 60~90%).

$^1$H NMR(400 MHz, CDCl$_3$) δ1.00(1, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 51

Synthesis of 1-(2,6-dichlorophenyl)-(R)-1-hydroxy-3-methyl-butyl-(R)-2-carbamate (51)

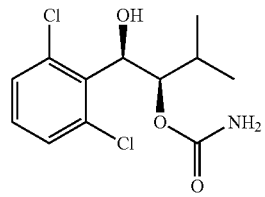 [SMILES: CC(C)[C@@H](OC(N)=O)[C@H](O)c1c(Cl)cccc1Cl]

The substantially same method as described in Example 1 was conducted, except that 1-(2,6-dichlorophenyl)-3-methyl-(R,R)-1,2-(Bis-trimethylsilanyloxy)butane (Preparation Example 98) was used instead of 1-(2-chlorophenyl)-(S,S)-1,2-(Bis-trimethylsilanyloxy)propane (Preparation example 69) to obtain the title compound (2.6 g, yield 60~90%).

$^1$H NMR(400 MHz, CDCl$_3$) δ1.00(1, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 52

Synthesis of 1-(2,4-dichlorophenyl)-(R)-1-hydroxy-hexyl-(R)-2-carbamate (52)

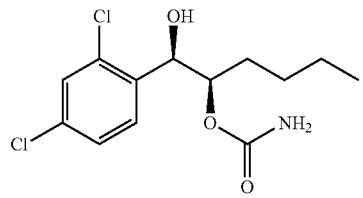 [SMILES: CCCC[C@@H](OC(N)=O)[C@H](O)c1ccc(Cl)cc1Cl]

The substantially same method as described in Example 1 was conducted, except that 1-(2,4-dichlorophenyl)-(R,R)-1,2-(Bis-trimethylsilanyloxy)hexane (Preparation Example 99) was used instead of 1-(2-chlorophenyl)-(S,S)-1,2-(Bis-trimethylsilanyloxy)propane (Preparation example 69) to obtain the title compound (2.5 g, yield 60~90%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m, 3H)

Example 53

Synthesis of 1-(2,6-dichlorophenyl)-(R)-1-hydroxy-hexyl-(R)-2-carbamate (53)

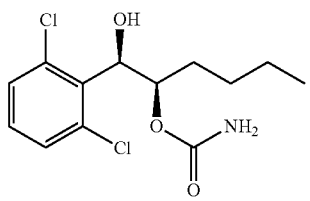 [SMILES: CCCC[C@@H](OC(N)=O)[C@H](O)c1c(Cl)cccc1Cl]

The substantially same method as described in Example 1 was conducted, except that 1-(2,6-dichlorophenyl)-(R,R)-1,2-(Bis-trimethylsilanyloxy)hexane (Preparation Example 100) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 54

Synthesis of
1-(2,4-dichlorophenyl)-1-hydroxypropyl-2-carbamate
(54)

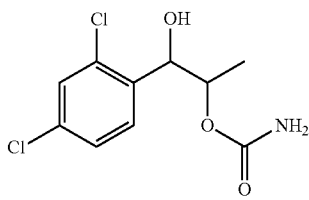 [SMILES: CC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)propane (Preparation Example 101) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR(400 MHz, CDCl$_3$) δ1.22(d, J=6.4 Hz, 3H), 4.16 (br t, 1H) 4.96(br t, 3H), 5.07(t, J=4.8 Hz, 1H), 7.23~7.52(m, 3H)

Example 55

Synthesis of
1-(2,6-dichlorophenyl)-1-hydroxypropyl-2-carbamate
(55)

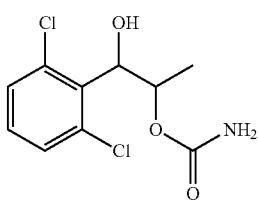 [SMILES: CC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)propane (Preparation Example 102) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 56

Synthesis of
1-(2,3-dichlorophenyl)-1-hydroxypropyl-2-carbamate
(56)

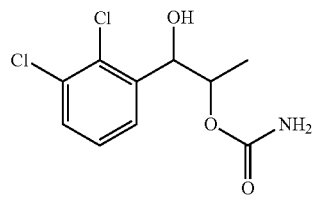 [SMILES: CC(OC(N)=O)C(O)c1cccc(Cl)c1Cl]

The substantially same method as described in Example 1 was conducted, except that 1-(2,3-dichlorophenyl)-1,2-(Bis-trimethylsilanyloxy)propane (Preparation Example 103) was used instead of 1-(2-chlorophenyl)-(S,S)-1,2-(Bis-trimethylsilanyloxy)propane (Preparation example 69) to obtain the title compound (1.6 g, yield 60~90%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 57

Synthesis of
1-(2,4-dichlorophenyl)-1-hydroxybutyl-2-carbamate
(57)

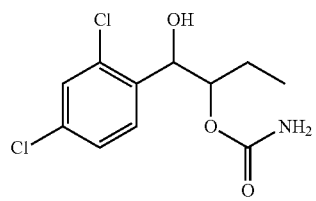 [SMILES: CCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)butane (Preparation Example 104) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR(400 MHz, CDCl$_3$) δ0.96(t, J=7.4 Hz, 3H), 1.58~1.74(m, 2H), 2.98(d, J=5.6 Hz, 1H) 4.68(br s, 2H), 5.59(dt, J=5.2, 8.8 Hz, 1H), 5.19(t, J=5.4 Hz, 1H), 7.30~7.50 (m, 3H)

Example 58

Synthesis of
1-(2,6-dichlorophenyl)-1-hydroxybutyl-2-carbamate
(58)

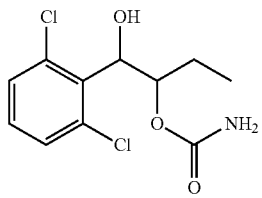 [SMILES: CCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)butane (Preparation Example 105) was used instead of 1-(2-chlorophenyl)-(S,S)-1,2-(Bis-trimethylsilanyloxy)propane (Preparation example 69) to obtain the title compound (2.4 g, yield 60~90%).

$^1$H NMR(400 MHz, CDCl$_3$) δ0.92(t, J=7.4 Hz, 3H), 1.30~1.38(m, 1H), 1.57~1.64(m, 1H), 3.74(d, J=9.2 Hz, 1H), 4.80(br s, 2H), 5.40~5.50(m, 2H), 7.17~7.34(m, 3H)

Example 59

Synthesis of 1-(2,4-dichlorophenyl)-1-hydroxy-3-methyl-butyl-2-carbamate (59)

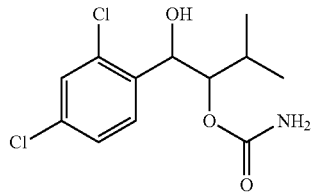 [SMILES: CC(C)C(OC(N)=O)C(O)c1ccc(Cl)cc1Cl]

The substantially same method as described in Example 1 was conducted, except that 1-(2,4-dichlorophenyl)-3-methyl-1,2-(Bis-trimethylsilanyloxy)butane (Preparation Example 106) was used instead of 1-(2-chlorophenyl)-(S,S)-1,2-(Bis-trimethylsilanyloxy)propane (Preparation example 69) to obtain the title compound (1.9 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.30~7.50(m, 3H)

Example 60

Synthesis of 1-(2,6-dichlorophenyl)-1-hydroxy-3-methyl-butyl-2-carbamate (60)

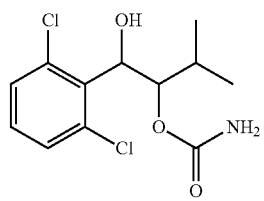 [SMILES: CC(C)C(OC(N)=O)C(O)c1c(Cl)cccc1Cl]

The substantially same method as described in Example 1 was conducted, except that 1-(2,6-dichlorophenyl)-3-methyl-1,2-(Bis-trimethylsilanyloxy)butane (Preparation Example 107) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR(400 MHz, CDCl$_3$) δ1.00(t, J=7.2 Hz, 6H), 1.73~1.79(m, 1H), 3.67~3.69(m, 1H), 4.85(br s, 2H), 5.40~5.43(m, 1H), 5.49~5.54(m, 1H), 7.16~7.33(m, 3H)

Example 61

Synthesis of 1-(2,4-dichlorophenyl)-1-hydroxyhexyl-2-carbamate (61)

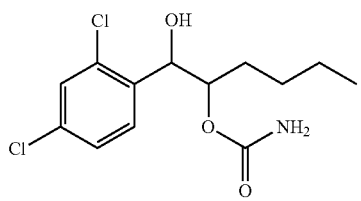 [SMILES: CCCCC(OC(N)=O)C(O)c1ccc(Cl)cc1Cl]

The substantially same method as described in Example 1 was conducted, except that 1-(2,4-dichlorophenyl)-1,2-(Bis-trimethylsilanyloxy)hexane (Preparation Example 108) was used instead of 1-(2-chlorophenyl)-(S,S)-1,2-(Bis-trimethylsilanyloxy)propane (Preparation example 69) to obtain the title compound (2.6 g, yield 60~90%).

$^1$H NMR(400 MHz, CDCl$_3$) δ0.89(t, J=3.6 Hz, 3H), 1.28~1.42(m, 4H), 1.52~1.59(m, 1H), 1.64~1.71(m, 1H), 2.98(d, J=5.6 Hz, 1H), 4.67(br s, 2H), 4.96~5.00(m, 1H), 5.17(t, J=5.6 Hz, 1H), 7.30~7.49(m, 3H)

Example 62

Synthesis of 1-(2,6-dichlorophenyl)-1-hydroxyhexyl-2-carbamate (62)

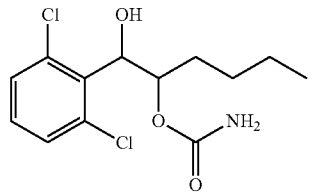 [SMILES: CCCCC(OC(N)=O)C(O)c1c(Cl)cccc1Cl]

The substantially same method as described in Example 1 was conducted, except that 1-(2,6-dichlorophenyl)-1,2-(Bis-trimethylsilanyloxy)hexane (Preparation Example 109) was used instead of 1-(2-chlorophenyl)-(S,S)-1,2-(Bis-trimethylsilanyloxy)propane (Preparation example 69) to obtain the title compound (2.5 g, yield 60~90%).

$^1$H NMR(400 MHz, CDCl$_3$) δ0.84(t, J=7.0 Hz, 3H), 1.20~1.35(m, 4H), 1.36~1.41(m, 1H), 1.59~1.63(m, 1H), 3.71(d, J=10.0 Hz, 1H), 4.74(br s, 2H), 5.40~5.44(m, 1H), 5.52~5.57(m, 1H), 7.17~7.35(m, 3H)

Example 63

Synthesis of 1-(2-fluorophenyl)-(S)-1-hydroxypropyl-(S)-2-carbamate (63)

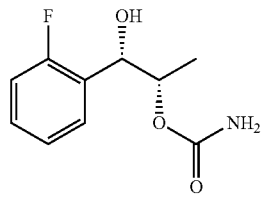

Example 64

Synthesis of 1-(2-fluorophenyl)-(R)-1-hydroxypropyl-(R)-2-carbamate (64)

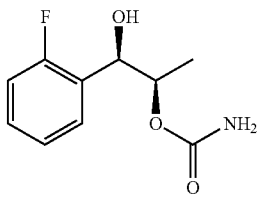

The substantially same method as described in Example 1 was conducted, except that 1-(2-fluorophenyl)-(R,R)-1,2-(Bis-trimethylsilanyloxy)propane (Preparation Example 111) was used instead of 1-(2-chlorophenyl)-(S,S)-1,2-(Bis-trimethylsilanyloxy)propane (Preparation example 69) to obtain the title compound (1.6 g, yield 60~90%).

$^1$H NMR(400 MHz, CDCl$_3$) δ1.19(d, J=5.2 Hz, 3H), 2.93 (d, J=4.4 Hz, 1H), 4.71(br s, 2H), 4.99~5.06(m, H), 7.04~7.48 (m, 4H)

Example 65

Synthesis of 1-(2-iodophenyl)-(S)-1-hydroxypropyl-(S)-2-carbamate (65)

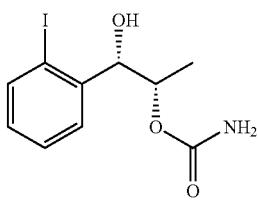

The substantially same method as described in Example 1 was conducted, except that 1-(2-iodophenyl)-(S,S)-1,2-(Bis-trimethylsilanyloxy)propane (Preparation Example 112) was used instead of 1-(2-chlorophenyl)-(S,S)-1,2-(Bis-trimethylsilanyloxy)propane (Preparation example 69) to obtain the title compound (2.2 g, yield 60~90%).

$^1$H NMR(400 MHz, CDCl$_3$) δ1.27(d, J=6.4 Hz, 3H), 3.09 (br s, 1H), 4.83(br s, 2H), 5.00~5.10(m, 2H), 7.00~7.76(m, 4H)

Example 66

Synthesis of 1-(2-iodophenyl)-(R)-1-hydroxypropyl-(R)-2-carbamate (66)

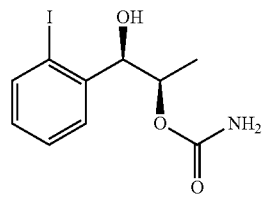

The substantially same method as described in Example 1 was conducted, except that 1-(2-iodophenyl)-(R,R)-1,2-(Bis-trimethylsilanyloxy)propane (Preparation Example 113) was used instead of 1-(2-chlorophenyl)-(S,S)-1,2-(Bis-trimethylsilanyloxy)propane (Preparation example 69) to obtain the title compound (1.7 g, yield 60~90%).

$^1$H NMR(400 MHz, CDCl$_3$) δ1.27(d, J=6.4 Hz, 3H), 2.95 (d, J=3.6 Hz, 1H), 4.73(br s, 2H), 5.01~5.11(m, 2H), 7.01~7.86(m, 4H)

Example 67

Synthesis of 1-(2-iodophenyl)-(S)-1-hydroxybutyl-(S)-2-carbamate (67)

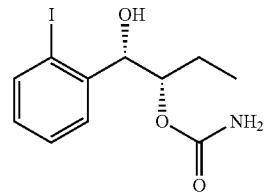 [SMILES: CC[C@H](OC(N)=O)[C@@H](O)c1ccccc1I]

The substantially same method as described in Example 1 was conducted, except that 1-(2-iodophenyl)-(S,S)-1,2-(Bis-trimethylsilanyloxy)butane (Preparation Example 114) was used instead of 1-(2-chlorophenyl)-(S,S)-1,2-(Bis-trimethylsilanyloxy)propane (Preparation example 69) to obtain the title compound (2.1 g, yield 60~90%).

$^1$H NMR(400 MHz, CDCl$_3$) δ1.27(d, J=6.4 Hz, 3H), 3.09 (br s, 1H), 4.83(br s, 2H), 5.00~5.10(m, 2H), 7.00~7.76(m, 4H)

Example 68

Synthesis of 1-(2-chlorophenyl)-(S)-2-hydroxypropyl-(S)-1-carbamate (68)

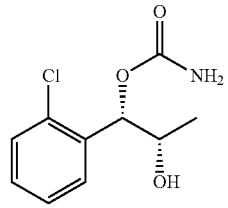

The substantially same method as described in Example 1 was conducted, except that 1-(2-fluorophenyl)-(S,S)-1,2-(Bis-trimethylsilanyloxy)propane (Preparation Example 110) was used instead of 1-(2-chlorophenyl)-(S,S)-1,2-(Bis-trimethylsilanyloxy)propane (Preparation example 69) to obtain the title compound (1.8 g, yield 60~90%).

$^1$H NMR(400 MHz, CDCl$_3$) δ1.19(d, J=5.2 Hz, 3H), 2.93 (d, J=4.4 Hz, 1H), 4.71(br s, 2H), 4.99~5.06(m, H), 7.04~7.48 (m, 4H)

1-(2-chlorophenyl)-(S,S)-1,2-propanediol (2.33 g, Preparation example 14) obtained in Preparation Example 14, tetrahydrofuran (THF, 12 ml), and carbonyldiimidazole (CDI, 3.04 g) were put into a flask and stirred at the room temperature. After approximately 3 hours, ammonia solution (NH₄OH, 4 ml) was added thereto. When the reaction was completed, the obtained product was washed with 1M HCl solution and ethylacetate (EA). The separated organic layer was dehydrated with anhydrous magnesium sulfate (MgSO₄), filtrated, and concented under reduced pressure. The concentrated residue was purified by a silica gel column chromatography, to obtain the title compound (0.28 g, yield 10~30%).

¹H NMR(400 MHz, CDCl₃) δ1.24(d, J=6.8 Hz, 3H), 2.13 (d, J=4.4 Hz, 1H), 4.12~4.16(m, 1H), 4.85(br s, 2H), 5.98(d, J=5.6 Hz, 1H), 7.24~7.43(m, 4H)

Example 69

Synthesis of 1-(2-chlorophenyl)-(R)-2-hydroxypropyl-(R)-1-carbamate (69)

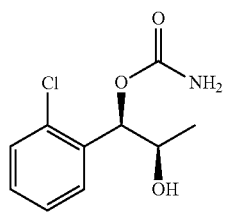

The substantially same method as described in Example 68 was conducted, except that 1-(2-chlorophenyl)-(R,R)-1,2-propanediol (Preparation Example 15) was used instead of 1-(2-chlorophenyl)-(S,S)-1,2-propanediol (Preparation example 14) to obtain the title compound (0.77 g, yield 16%).

¹H NMR(400 MHz, CDCl₃) δ1.24(d, J=6.4 Hz, 3H), 2.04 (d, J=4.8 Hz, 1H), 4.11~4.18(m, 1H), 4.74(br s, 2H), 6.00(d, J=5.6 Hz, 1H), 7.24~7.43(m, 4H)

Example 70

Synthesis of 1-(2-chlorophenyl)-2-hydroxypropyl-1-carbamate (70)

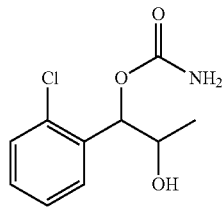

The substantially same method as described in Example 68 was conducted, except that 1-(2-chlorophenyl)-(R,R)-1,2-propanediol (Preparation Example 16) was used instead of 1-(2-chlorophenyl)-(S,S)-1,2-propanediol (Preparation example 14) to obtain the title compound (0.16 g, yield 10~30%).

¹H NMR(400 MHz, CDCl₃) δ1.24(d, J=6.4 Hz, 3H), 2.04 (d, J=4.8 Hz, 1H), 4.11~4.18(m, 1H), 4.74(br s, 2H), 6.00(d, J=5.6 Hz, 1H), 7.24~7.43(m, 4H)

Example 71

Synthesis of 1-(2-chlorophenyl)-(S)-2-hydroxypropyl-(S)-1-N-methylcarbamate (71)

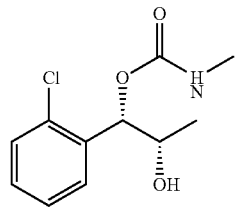 [SMILES: CNC(=O)O[C@@H](c1ccccc1Cl)[C@H](C)O]

A regioisomer of monocarbamate was separated and purified by conducting the silica gel column chromatography as described in Example 15, to obtain the title compound (0.70 g, yield 10~30%).

¹H NMR(400 MHz, CDCl₃) δ1.21(d, J=6.4 Hz, 3H), 2.80 (d, J=4.8 Hz, 3H), 3.12(s, 1H), 4.09~4.16(m, 1H), 4.86(br s, 1H), 5.99(d, J=6.0 Hz, 1H), 7.23~7.40(m, 4H)

Example 72

Synthesis of 1-(2-chlorophenyl)-(R)-2-hydroxypropyl-(R)-1-N-methylcarbamate (72)

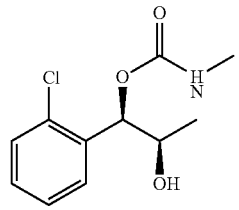 [SMILES: CNC(=O)O[C@H](c1ccccc1Cl)[C@@H](C)O]

A regioisomer of monocarbamate was separated and purified by conducting the silica gel column chromatography as described in Example 22, to obtain the title compound (0.69 g, yield 10~30%).

¹H NMR(400 MHz, CDCl₃) δ1.21(d, J=6.4 Hz, 3H), 2.80 (d, J=4.8 Hz, 3H), 3.12(s, 1H), 4.09~4.16(m, 1H), 4.86(br s, 1H), 5.99(d, J=6.0 Hz, 1H), 7.23~7.40(m, 4H)

Example 73

Synthesis of 1-(2-chlorophenyl)-2-hydroxypropyl-1-N-methylcarbamate (73)

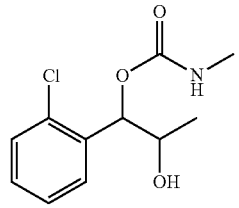 [SMILES: CNC(=O)OC(c1ccccc1Cl)C(C)O]

A regioisomer of monocarbamate was separated and purified by conducting the silica gel column chromatography as described in Example 29, to obtain the title compound (0.73 g, yield 10~30%).

$^1$H NMR(400 MHz, CDCl$_3$) δ 1.22(d, J=6 Hz, 3H), 2.15(d, J=4 Hz, 1H), 2.81(d, J=5 Hz, 3H), 4.12(dd, J=6 Hz, 1H), 4.83(br s, 1H), 6.00(d, J=6 Hz, 1H), 7.23~7.41(m, 4H)

Example 74

Synthesis of 1-(2-chlorophenyl)-(S)-2-hydroxypropyl-(S)-1-N-propylcarbamate (74)

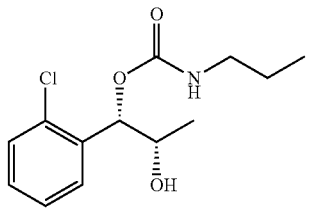 [SMILES: CCCNC(=O)O[C@@H](c1ccccc1Cl)[C@H](C)O]

A regioisomer of monocarbamate was separated and purified by conducting the silica gel column chromatography as described in Example 16, to obtain the title compound (0.15 g, yield 10~30%).

$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 75

Synthesis of 1-(2-chlorophenyl)-(R)-2-hydroxypropyl-(R)-1-N-propylcarbamate (75)

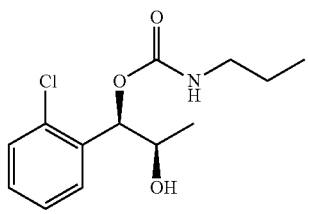 [SMILES: CCCNC(=O)O[C@H](c1ccccc1Cl)[C@@H](C)O]

A regioisomer of monocarbamate was separated and purified by conducting the silica gel column chromatography as described in Example 23, to obtain the title compound (0.04 g, yield 10~30%).

$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 76

Synthesis of 1-(2-chlorophenyl)-2-hydroxypropyl-1-N-propylcarbamate (76)

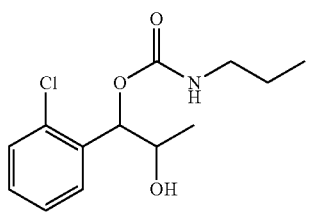 [SMILES: CCCNC(=O)OC(c1ccccc1Cl)C(C)O]

A regioisomer of monocarbamate was separated and purified by conducting the silica gel column chromatography as described in Example 30, to obtain the title compound (0.15 g, yield 10~30%).

$^1$H NMR(400 MHz, CDCl$_3$) δ 0.91(t, J=7 Hz, 3H), 1.22(d, J=6 Hz, 3H), 1.52(dd, J=7 Hz, 2H), 2.23(d, J=4 Hz, 1H), 3.09~3.21(m, 2H), 4.09~4.17(m, 1H), 4.93(s, 1H), 5.99(d, J=6 Hz, 1H), 7.23~7.47(m, 4H)

Example 77

Synthesis of 1-(2-chlorophenyl)-(S)-2-hydroxypropyl-(S)-1-N-isopropylcarbamate (77)

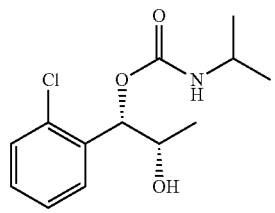 [SMILES: CC(C)NC(=O)O[C@@H](c1ccccc1Cl)[C@H](C)O]

A regioisomer of monocarbamate was separated and purified by conducting the silica gel column chromatography as described in Example 17, to obtain the title compound (0.42 g, yield 10~30%).

$^1$H NMR(400 MHz, CDCl$_3$) δ 1.10(d, J=6.0 Hz, 3H), 1.15~1.19(m, 6H), 2.41(s, 1H), 3.76~4.08(m, 1H), 4.34(s, 1H), 4.83(br s 1H), 5.95(d, J=5.3 Hz, 1H), 7.19~7.39(m, 4H)

Example 78

Synthesis of 1-(2-chlorophenyl)-(R)-2-hydroxypropyl-(R)-1-N-isopropylcarbamate (78)

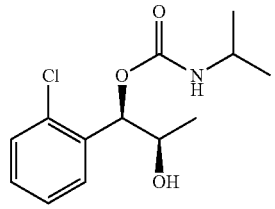 [SMILES: CC(C)NC(=O)O[C@H](c1ccccc1Cl)[C@@H](C)O]

A regioisomer of monocarbamate was separated and purified by conducting the silica gel column chromatography as described in Example 24, to obtain the title compound (0.5 g, yield 10~30%).

$^1$H NMR(400 MHz, CDCl$_3$) δ1.13(d, J=6 Hz, 3H), 1.20 (dd, J=9.2 Hz, 6H), 2.23(s, 1H), 3.77~3.82(m, 1H), 4.10(s, 1H), 4.76(br s, 1H), 5.98(d, J=5.6 Hz, 1H), 7.23~7.41(m, 4H)

Example 79

Synthesis of 1-(2-chlorophenyl)-2-hydroxypropyl-1-N-isopropylcarbamate (79)

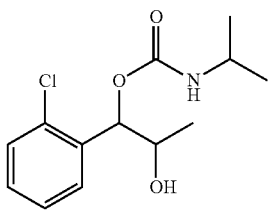 [SMILES: CC(C)NC(=O)OC(c1ccccc1Cl)C(C)O]

A regioisomer of monocarbamate was separated and purified by conducting the silica gel column chromatography as described in Example 31, to obtain the title compound (0.09 g, yield 10~30%).

$^1$H NMR(400 MHz, CDCl$_3$) δ 1.14(d, J=6 Hz, 3H), 1.21 (dd, J=6 Hz, 6H), 2.16(d, J=5 Hz, 1H), 3.81(t, J=6 Hz, 1H), 4.11(d, J=5 Hz, 1H), 4.73(br s, 1H), 5.98(d, J=5 Hz, 1H), 7.24~741(m, 4H)

Example 80

Synthesis of 1-(2-chlorophenyl)-(S)-2-hydroxypropyl-(S)-1-N-cyclopropylcarbamate (80)

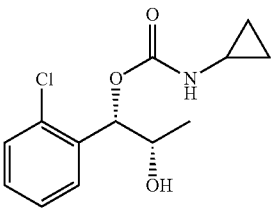 [SMILES: C[C@H](O)[C@@H](OC(=O)NC1CC1)c1ccccc1Cl]

A regioisomer of monocarbamate was separated and purified by conducting the silica gel column chromatography as described in Example 18, to obtain the title compound (0.53 g, yield 10~30%).

$^1$H NMR(400 MHz, CDCl$_3$) δ0.53~0.60(m, 2H), 0.74(s, 2H), 1.21(d, J=6.0 Hz, 3H), 2.19(s, 1H), 2.59(s, 1H), 4.11~4.15(m, 1H), 5.13(br s, 1H), 5.99(d, J=5.20 Hz, 1H), 7.23~7.40(m, 4H)

Example 81

Synthesis of 1-(2-chlorophenyl)-(R)-2-hydroxypropyl-(R)-1-N-cyclopropylcarbamate (81)

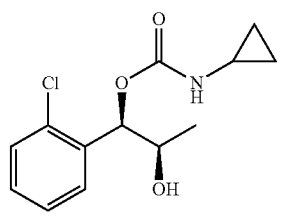 [SMILES: C[C@@H](O)[C@H](OC(=O)NC1CC1)c1ccccc1Cl]

A regioisomer of monocarbamate was separated and purified by conducting the silica gel column chromatography as described in Example 25, to obtain the title compound (0.58 g, yield 10%).

$^1$H NMR(400 MHz, CDCl$_3$) δ0.53~0.60(m, 2H), 0.74(s, 2H), 1.21(d, J=6.0 Hz, 3H), 2.19(s, 1H), 2.59(s, 1H), 4.11~4.15(m, 1H), 5.13(br s, 1H), 5.99(d, J=5.20 Hz, 1H), 7.23~7.40(m, 4H)

Example 82

Synthesis of 1-(2-chlorophenyl)-2-hydroxypropyl-1-N-cyclopropylcarbamate (82)

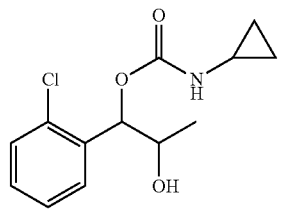 [SMILES: CC(O)C(OC(=O)NC1CC1)c1ccccc1Cl]

A regioisomer of monocarbamate was separated and purified by conducting the silica gel column chromatography as described in Example 32, to obtain the title compound (0.38 g, yield 14%).

$^1$H NMR(400 MHz, CDCl$_3$) δ 0.71(s, 2H), 1.19(d, J=6 Hz, 3H), 2.45(S, 1H), 2.57(S, 1H), 4.08~4.12(m, 1H), 5.26(s, 1H), 5.97(d, J=4 Hz, 1H), 7.22~7.54(m, 4H)

Example 83

Synthesis of 1-(2-chlorophenyl)-(S)-2-hydroxypropyl-(S)-1-N-cyclohexylcarbamate (83)

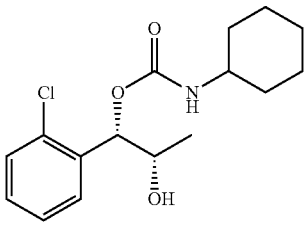 [SMILES: C[C@H](O)[C@@H](OC(=O)NC1CCCCC1)c1ccccc1Cl]

A regioisomer of monocarbamate was separated and purified by conducting the silica gel column chromatography as described in Example 19, to obtain the title compound (0.24 g, yield 10~30%).

$^1$H NMR(400 MHz, CDCl$_3$) δ1.10~1.39(m, 7H), 1.61(s, 3H), 1.71~1.74(m, 2H), 1.87(d, J=11.2 Hz, 1H), 2.48(d, J=10.8 Hz, 1H), 3.46(t, J=4 Hz, 1H), 4.10~4.11(m, 1H), 4.80(br s 1H), 5.97(d, J=5.6 Hz, 1H), 7.23~7.41(m, 4H)

Example 84

Synthesis of 1-(2-chlorophenyl)-(R)-2-hydroxypropyl-(R)-1-N-cyclohexylcarbamate (84)

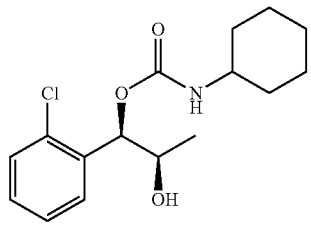 [SMILES: C[C@@H](O)[C@H](OC(=O)NC1CCCCC1)c1ccccc1Cl]

A regioisomer of monocarbamate was separated and purified by conducting the silica gel column chromatography as described in Example 26, to obtain the title compound (0.35 g, yield 10%).

$^1$H NMR(400 MHz, CDCl$_3$) δ1.10~1.39(m, 7H), 1.61(s, 3H), 1.71~1.74(m, 2H), 1.87(d, J=11.2 Hz, 1H), 2.48(d, J=10.8 Hz, 1H), 3.46(t, J=4 Hz, 1H), 4.10~4.11(m, 1H), 4.80(br s 1H), 5.97(d, J=5.6 Hz, 1H), 7.23~7.41(m, 4H)

Example 85

Synthesis of 1-(2-chlorophenyl)-2-hydroxypropyl-1-N-cyclohexylcarbamate (85)

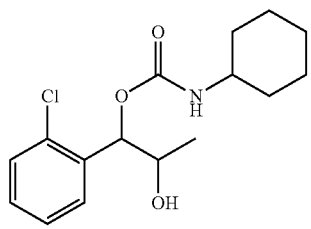 [SMILES: CC(O)C(OC(=O)NC1CCCCC1)c1ccccc1Cl]

A regioisomer of monocarbamate was separated and purified by conducting the silica gel column chromatography as described in Example 33, to obtain the title compound (0.26 g, yield 10%).

$^1$H NMR(400 MHz, CDCl$_3$) δ 1.12~1.19(m, 3H), 1.22(d, J=6 Hz, 3H), 1.27~1.37(m, 1H), 1.71(t, J=6 Hz, 2H), 1.86~1.88(m, 1H), 1.97~2.00(m, 1H), 2.18(d, J=4 Hz, 1H), 3.47(S, 1H), 4.12(t, J=6 Hz, 1H), 4.78(S, 1H), 5.97(d, J=6 Hz, 1H), 7.23~7.40(m, 4H)

Example 86

Synthesis of 1-(2-chlorophenyl)-(S)-2-hydroxypropyl-(S)-1-N-benzylcarbamate (86)

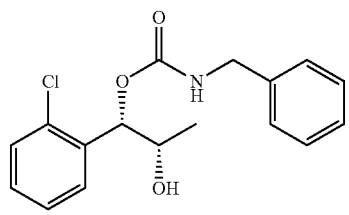 [SMILES: C[C@H](O)[C@@H](OC(=O)NCc1ccccc1)c1ccccc1Cl]

A regioisomer of monocarbamate was separated and purified by conducting the silica gel column chromatography as described in Example 20, to obtain the title compound (0.19 g, yield 10~30%).

$^1$H NMR(400 MHz, CDCl$_3$) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 87

Synthesis of 1-(2-chlorophenyl)-(R)-2-hydroxypropyl-(R)-1-N-benzylcarbamate (87)

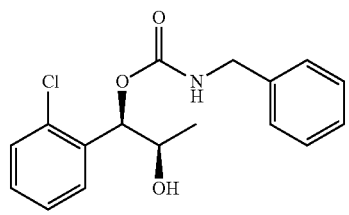 [SMILES: C[C@@H](O)[C@H](OC(=O)NCc1ccccc1)c1ccccc1Cl]

A regioisomer of monocarbamate was separated and purified by conducting the silica gel column chromatography as described in Example 27, to obtain the title compound (0.07 g, yield 10~30%).

$^1$H NMR(400 MHz, CDCl$_3$) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 88

Synthesis of 1-(2-chlorophenyl)-2-hydroxypropyl-1-N-benzylcarbamate (88)

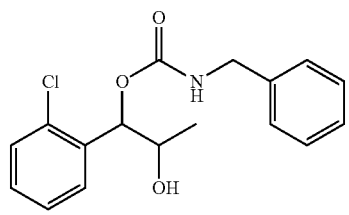 [SMILES: CC(O)C(OC(=O)NCc1ccccc1)c1ccccc1Cl]

A regioisomer of monocarbamate was separated and purified by conducting the silica gel column chromatography as described in Example 34, to obtain the title compound (0.21 g, yield 14%).

$^1$H NMR(400 MHz, CDCl$_3$) δ 1.23(d, J=6 Hz, 3H), 2.16(d, J=4 Hz, 1H), 4.12(t, J=6 Hz, 1H), 4.31~4.44(m, 2H), 5.22(br S, 1H), 6.04(d, J=6 Hz, 1H), 7.27~7.42(m, 9H)

Example 89

Synthesis of 1-(2,4-dichlorophenyl)-(S)-2-hydroxypropyl-(S)-1-carbamate (89)

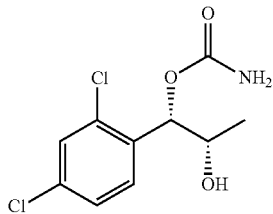 [SMILES: C[C@H](O)[C@@H](OC(N)=O)c1ccc(Cl)cc1Cl]

The substantially same method as described in Example 68 was conducted, except that 1-(2,4-dichlorophenyl)-(S,S)-1,2-propanediol (Preparation example 26) was used instead of 1-(2-chlorophenyl)-(S,S)-1,2-propanediol (Preparation example 14), to obtain the title compound (0.05 g, yield 10~30%).

$^1$H NMR(400 MHz, CDCl$_3$) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.30(d, J=8.4 Hz, 1H), 7.39(d, J=2.0 Hz, 2H), 7.50(dd, J=8.4 Hz, 2.0 Hz, 1H)

Example 90

Synthesis of 1-(2,6-dichlorophenyl)-(S)-2-hydroxypropyl-(S)-1-carbamate (90)

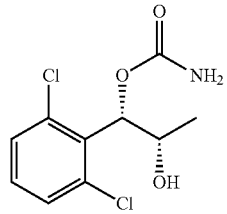 [SMILES: C[C@H](O)[C@@H](OC(N)=O)c1c(Cl)cccc1Cl]

The substantially same method as described in Example 68 was conducted, except that 1-(2,6-dichlorophenyl)-(S,S)-1,2-propanediol (Preparation example 38) was used instead of 1-(2-chlorophenyl)-(S,S)-1,2-propanediol (Preparation example 14), to obtain the title compound (0.07 g, yield 24%).

$^1$H NMR(400 MHz, CDCl$_3$) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.25~7.40(m, 3H)

Example 91

Synthesis of 1-(2,3-dichlorophenyl)-(S)-2-hydroxypropyl-(S)-1-carbamate (91)

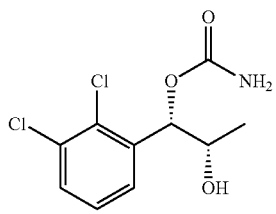 [SMILES: C[C@H](O)[C@@H](OC(N)=O)c1cccc(Cl)c1Cl]

The substantially same method as described in Example 68 was conducted, except that 1-(2,3-dichlorophenyl)-(S,S)-1,2-propanediol (Preparation example 57) was used instead of 1-(2-chlorophenyl)-(S,S)-1,2-propanediol (Preparation example 14), to obtain the title compound (0.08 g, yield 10~30%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 92

Synthesis of 1-(2,4-dichlorophenyl)-(S)-2-hydroxybutyl-(S)-1-carbamate (92)

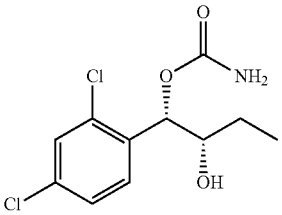 [SMILES: CC[C@H](O)[C@@H](OC(N)=O)c1ccc(Cl)cc1Cl]

The substantially same method as described in Example 68 was conducted, except that 1-(2,4-dichlorophenyl)-(S,S)-1,2-butanediol (Preparation example 29) was used instead of 1-(2-chlorophenyl)-(S,S)-1,2-propanediol (Preparation example 14), to obtain the title compound (0.07 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 93

Synthesis of 1-(2,6-dichlorophenyl)-(S)-2-hydroxybutyl-(S)-1-carbamate (93)

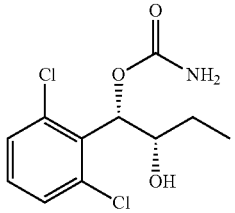 [SMILES: CC[C@H](O)[C@@H](OC(N)=O)c1c(Cl)cccc1Cl]

The substantially same method as described in Example 68 was conducted, except that 1-(2,6-dichlorophenyl)-(S,S)-1,2-butanediol (Preparation example 41) was used instead of 1-(2-chlorophenyl)-(S,S)-1,2-propanediol (Preparation example 14), to obtain the title compound (0.11 g, yield 29%).

¹H NMR(400 MHz, CDCl₃) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 94

Synthesis of 1-(2,4-dichlorophenyl)-(S)-2-hydroxy-3-methyl-butyl-(S)-1-carbamate (94)

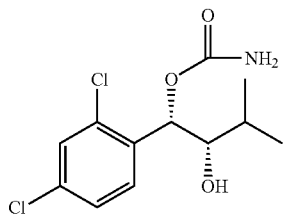 [SMILES: CC(C)[C@H](O)[C@@H](OC(N)=O)c1ccc(Cl)cc1Cl]

The substantially same method as described in Example 68 was conducted, except that 1-(2,4-dichlorophenyl)-3-methyl-(S,S)-1,2-butanediol (Preparation example 32) was used instead of 1-(2-chlorophenyl)-(S,S)-1,2-propanediol (Preparation example 14), to obtain the title compound (0.01 g, yield 10~30%).

¹H NMR(400 MHz, CDCl₃) δ1.00(1, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 95

Synthesis of 1-(2,6-dichlorophenyl)-(S)-2-hydroxy-3-methyl-butyl-(S)-1-carbamate (95)

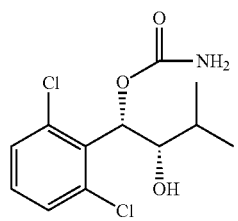

The substantially same method as described in Example 68 was conducted, except that 1-(2,6-dichlorophenyl)-3-methyl-(S,S)-1,2-butanediol (Preparation example 44) was used instead of 1-(2-chlorophenyl)-(S,S)-1,2-propanediol (Preparation example 14), to obtain the title compound (0.03 g, yield 10~30%).

¹H NMR(400 MHz, CDCl₃) δ1.00(1, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 96

Synthesis of 1-(2,4-dichlorophenyl)-(S)-2-hydroxy-hexyl-(S)-1-carbamate (96)

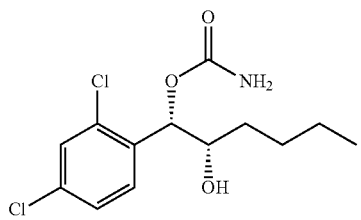 [SMILES: CCCC[C@H](O)[C@@H](OC(N)=O)c1ccc(Cl)cc1Cl]

The substantially same method as described in Example 68 was conducted, except that 1-(2,4-dichlorophenyl)-(S,S)-1,2-hexanediol (Preparation example 35) was used instead of 1-(2-chlorophenyl)-(S,S)-1,2-propanediol (Preparation example 14), to obtain the title compound (0.21 g, yield 10~30%).

¹H NMR(400 MHz, CDCl₃) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 97

Synthesis of 1-(2,6-dichlorophenyl)-(S)-2-hydroxy-hexyl-(S)-1-carbamate (97)

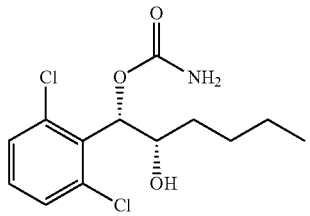 [SMILES: CCCC[C@H](O)[C@@H](OC(N)=O)c1c(Cl)cccc1Cl]

The substantially same method as described in Example 68 was conducted, except that 1-(2,6-dichlorophenyl)-(S,S)-1,2-hexanediol (Preparation example 47) was used instead of 1-(2-chlorophenyl)-(S,S)-1,2-propanediol (Preparation example 14), to obtain the title compound (0.06 g, yield 29%).

¹H NMR(400 MHz, CDCl₃) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Example 98

Synthesis of 1-(2,4-dichlorophenyl)-(R)-2-hydroxypropyl-(R)-1-carbamate (98)

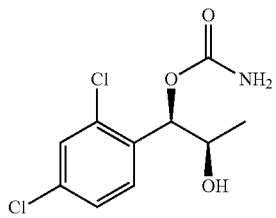 [SMILES: C[C@@H](O)[C@H](OC(N)=O)c1ccc(Cl)cc1Cl]

The substantially same method as described in Example 68 was conducted, except that 1-(2,4-dichlorophenyl)-(R,R)-1,2-propanediol (Preparation example 27) was used instead of 1-(2-chlorophenyl)-(S,S)-1,2-propanediol (Preparation example 14), to obtain the title compound (0.04 g, yield 10~30%).

$^1$H NMR(400 MHz, CDCl$_3$) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.30~7.50(m, 3H)

Example 99

Synthesis of 1-(2,6-dichlorophenyl)-(R)-2-hydroxypropyl-(R)-1-carbamate (99)

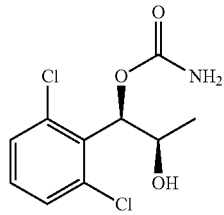 [SMILES: C[C@@H](O)[C@H](OC(N)=O)c1c(Cl)cccc1Cl]

The substantially same method as described in Example 68 was conducted, except that 1-(2,6-dichlorophenyl)-(R,R)-1,2-propanediol (Preparation example 39) was used instead of 1-(2-chlorophenyl)-(S,S)-1,2-propanediol (Preparation example 14), to obtain the title compound (0.09 g, yield 10~30%).

$^1$H NMR(400 MHz, CDCl$_3$) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.25~7.40(m, 3H)

Example 100

Synthesis of 1-(2,3-dichlorophenyl)-(R)-2-hydroxypropyl-(R)-1-carbamate (100)

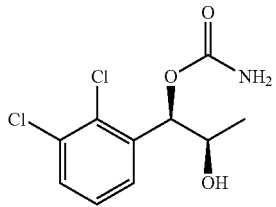 [SMILES: C[C@@H](O)[C@H](OC(N)=O)c1cccc(Cl)c1Cl]

The substantially same method as described in Example 68 was conducted, except that 1-(2,3-dichlorophenyl)-(R,R)-1,2-propanediol (Preparation example 58) was used instead of 1-(2-chlorophenyl)-(S,S)-1,2-propanediol (Preparation example 14), to obtain the title compound (0.25 g, yield 10~30%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 101

Synthesis of 1-(2,4-dichlorophenyl)-(R)-2-hydroxybutyl-(R)-1-carbamate (101)

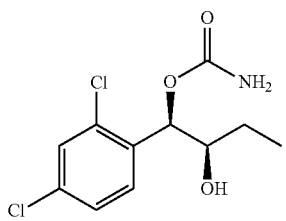 [SMILES: CC[C@@H](O)[C@H](OC(N)=O)c1ccc(Cl)cc1Cl]

The substantially same method as described in Example 68 was conducted, except that 1-(2,4-dichlorophenyl)-(R,R)-1,2-butanediol (Preparation example 30) was used instead of 1-(2-chlorophenyl)-(S,S)-1,2-propanediol (Preparation example 14), to obtain the title compound (0.08 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 102

Synthesis of 1-(2,6-dichlorophenyl)-(R)-2-hydroxybutyl-(R)-1-carbamate (102)

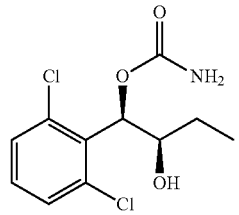 [SMILES: CC[C@@H](O)[C@H](OC(N)=O)c1c(Cl)cccc1Cl]

The substantially same method as described in Example 68 was conducted, except that 1-(2,6-dichlorophenyl)-(R,R)-1,2-butanediol (Preparation example 42) was used instead of 1-(2-chlorophenyl)-(S,S)-1,2-propanediol (Preparation example 14), to obtain the title compound (0.09 g, yield 10~30%). $^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 103

Synthesis of 1-(2,4-dichlorophenyl)-(R)-2-hydroxy-3-methyl-butyl-(R)-1-carbamate (103)

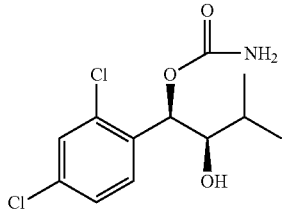 [SMILES: CC(C)[C@@H](O)[C@H](OC(N)=O)c1ccc(Cl)cc1Cl]

The substantially same method as described in Example 68 was conducted, except that 1-(2,4-dichlorophenyl)-3-methyl-(R,R)-1,2-propanediol (Preparation example 33) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 104

Synthesis of 1-(2,6-dichlorophenyl)-(R)-2-hydroxy-3-methyl-butyl-(R)-1-carbamate (104)

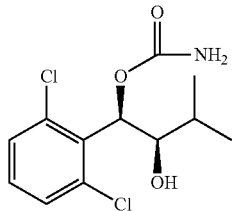 [SMILES: CC(C)[C@@H](O)[C@H](OC(N)=O)c1c(Cl)cccc1Cl]

The substantially same method as described in Example 68 was conducted, except that 1-(2,6-dichlorophenyl)-3-methyl-(R,R)-1,2-propanediol (Preparation example 45) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(1, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 105

Synthesis of 1-(2,4-dichlorophenyl)-(R)-2-hydroxy-hexyl-(R)-1-carbamate (105)

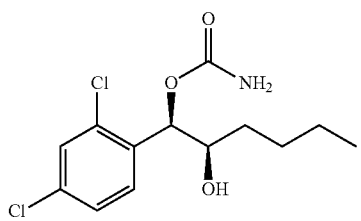 [SMILES: CCCC[C@@H](O)[C@H](OC(N)=O)c1ccc(Cl)cc1Cl]

The substantially same method as described in Example 68 was conducted, except that 1-(2,4-dichlorophenyl)-(R,R)-1,2-hexanediol (Preparation example 36) was used instead of 1-(2-chlorophenyl)-(S,S)-1,2-propanediol (Preparation example 14), to obtain the title compound (0.21 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 106

Synthesis of 1-(2,6-dichlorophenyl)-(R)-2-hydroxy-hexyl-(R)-1-carbamate (106)

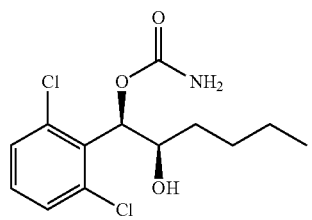 [SMILES: CCCC[C@@H](O)[C@H](OC(N)=O)c1c(Cl)cccc1Cl]

The substantially same method as described in Example 68 was conducted, except that 1-(2,6-dichlorophenyl)-(R,R)-1,2-hexanediol (Preparation example 48) was used instead of 1-(2-chlorophenyl)-(S,S)-1,2-propanediol (Preparation example 14), to obtain the title compound (0.12 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Example 107

Synthesis of 1-(2,4-dichlorophenyl)-2-hydroxypropyl-1-carbamate (107)

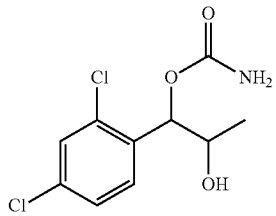 [SMILES: CC(O)C(OC(N)=O)c1ccc(Cl)cc1Cl]

The substantially same method as described in Example 68 was conducted, except that 1-(2,4-dichlorophenyl)-1,2-propanediol (Preparation example 28) was used instead of 1-(2-chlorophenyl)-(S,S)-1,2-propanediol (Preparation example 14), to obtain the title compound (0.05 g, yield 10~30%).

$^1$H NMR(400 MHz, CDCl$_3$) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.30~7.50(m, 3H)

Example 108

Synthesis of 1-(2,6-dichlorophenyl)-2-hydroxypropyl-1-carbamate (108)

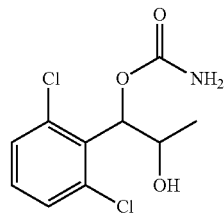 [SMILES: CC(O)C(OC(N)=O)c1c(Cl)cccc1Cl]

The substantially same method as described in Example 68 was conducted, except that 1-(2,6-dichlorophenyl)-1,2-propanediol (Preparation example 40) was used instead of 1-(2-chlorophenyl)-(S,S)-1,2-propanediol (Preparation example 14), to obtain the title compound (0.06 g, yield 10~30%).

$^1$H NMR(400 MHz, CDCl$_3$) δ1.13(d, J=6.8 Hz, 3H), 2.49 (d, J=4.0 Hz, 1H), 4.66~4.74(m, 1H), 4.76(br s, 2H), 6.20(d, J=8.8 Hz, 1H), 7.25~7.40(m, 3H)

Example 109

Synthesis of 1-(2,3-dichlorophenyl)-(R)-2-hydroxypropyl-(R)-1-carbamate (109)

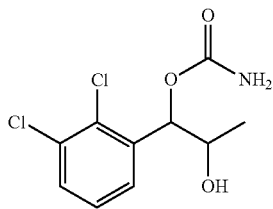 [SMILES: CC(O)C(OC(N)=O)c1cccc(Cl)c1Cl]

The substantially same method as described in Example 68 was conducted, except that 1-(2,3-dichlorophenyl)-1,2-propanediol (Preparation example 59) was used instead of 1-(2-chlorophenyl)-(S,S)-1,2-propanediol (Preparation example 14), to obtain the title compound (0.02 g, yield 10~30%).

$^1$H NMR(400 MHz, CDCl$_3$) δ1.15(d, J=6.4 Hz, 3H), 3.66 (d, J=9.2 Hz, 1H), 4.73(br s, 2H), 5.43(t, J=9.0 Hz, 1H), 5.62~5.69(m, 1H), 7.18~7.22(m, 3H),

Example 110

Synthesis of 1-(2,4-dichlorophenyl)-2-hydroxybutyl-1-carbamate (110)

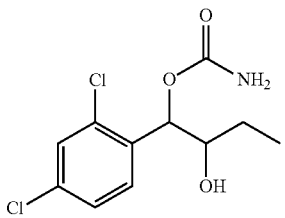 [SMILES: CCC(O)C(OC(N)=O)c1ccc(Cl)cc1Cl]

The substantially same method as described in Example 68 was conducted, except that 1-(2,4-dichlorophenyl)-1,2-butanediol (Preparation example 31) was used instead of 1-(2-chlorophenyl)-(S,S)-1,2-propanediol (Preparation example 14), to obtain the title compound (0.07 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.30~7.50(m, 3H)

Example 111

Synthesis of 1-(2,6-dichlorophenyl)-2-hydroxybutyl-1-carbamate (111)

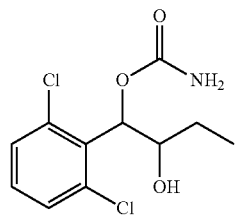 [SMILES: CCC(O)C(OC(N)=O)c1c(Cl)cccc1Cl]

The substantially same method as described in Example 68 was conducted, except that 1-(2,6-dichlorophenyl)-1,2-butanediol (Preparation example 43) was used instead of 1-(2-chlorophenyl)-(S,S)-1,2-propanediol (Preparation example 14), to obtain the title compound (0.10 g, yield 10~30%).

$^1$H NMR(400 MHz, CDCl$_3$) δ0.77(t, J=7.4 Hz, 3H), 0.92~1.01(m, 1H), 1.18~1.28(m, 1H), 4.06~4.13(m, 1H), 4.96(d, J=6.0 Hz, 1H), 5.91(d, J=8.8 Hz, 1H), 6.4(br s, 2H), 7.25~7.40(m, 3H)

Example 112

Synthesis of 1-(2,4-dichlorophenyl)-2-hydroxy-3-methyl-butyl-1-carbamate (112)

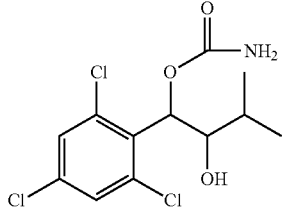 [SMILES: CC(C)C(O)C(OC(N)=O)c1c(Cl)cc(Cl)cc1Cl]

The substantially same method as described in Example 68 was conducted, except that 1-(2,4-dichlorophenyl)-3-methyl-1,2-propanediol (Preparation example 34) was used instead of 1-(2-chlorophenyl)-(S,S)-1,2-propanediol (Preparation example 14), to obtain the title compound (0.04 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.30~7.50(m, 3H)

Example 113

Synthesis of 1-(2,6-dichlorophenyl)-2-hydroxy-3-methyl-butyl-1-carbamate (113)

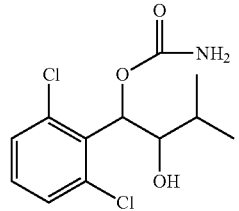 [SMILES: CC(C)C(O)C(OC(N)=O)c1c(Cl)cccc1Cl]

The substantially same method as described in Example 68 was conducted, except that 1-(2,6-dichlorophenyl)-3-methyl-1,2-propanediol (Preparation example 46) was used instead of 1-(2-chlorophenyl)-(S,S)-1,2-propanediol (Preparation example 14), to obtain the title compound (0.01 g, yield 10~30%).

$^1$H NMR(400 MHz, CDCl$_3$) δ1.00(t, J=7.2 Hz, 6H), 1.73~1.79(m, 1H), 3.67~3.69(m, 1H), 4.96(d, J=6.0 Hz, 1H), 5.91(d, J=8.8 Hz, 1H), 6.42(br s, 2H), 7.25~7.40(m, 3H)

Example 114

Synthesis of
1-(2,4-dichlorophenyl)-2-hydroxyhexyl-1-carbamate
(114)

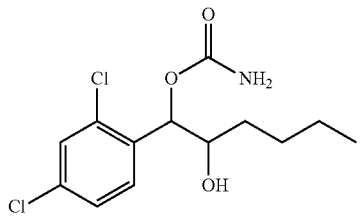 [SMILES: CCCCC(O)C(OC(N)=O)c1ccc(Cl)cc1Cl]

The substantially same method as described in Example 68 was conducted, except that 1-(2,4-dichlorophenyl)-1,2-hexanediol (Preparation example 37) was used instead of 1-(2-chlorophenyl)-(S,S)-1,2-propanediol (Preparation example 14), to obtain the title compound (0.21 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.30~7.50(m, 3H)

Example 115

Synthesis of
1-(2,6-dichlorophenyl)-2-hydroxyhexyl-1-carbamate
(115)

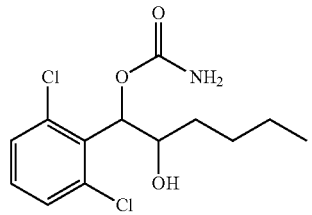 [SMILES: CCCCC(O)C(OC(N)=O)c1c(Cl)cccc1Cl]

The substantially same method as described in Example 68 was conducted, except that 1-(2,6-dichlorophenyl)-1,2-hexanediol (Preparation example 49) was used instead of 1-(2-chlorophenyl)-(S,S)-1,2-propanediol (Preparation example 14), to obtain the title compound (0.12 g, yield 10~30%).

$^1$H NMR(400 MHz, CDCl$_3$) δ0.85(t, J=7.2 Hz, 3H), 1.18~1.33(m, 4H), 1.48~1.55(m, 2H), 2.35(d, J=4.4 Hz, 1H), 4.45~4.50(m, 1H), 4.76(br s, 2H), 6.21(d, J=8.4 Hz, 1H), 7.16~7.34(m, 3H)

Compounds 1 to 115 produced in Examples 1 to 115 were summarized in following Tables 1 and 2.

TABLE 1

Compounds 1 to 67 having the structure of Chemical Formula 1 where 'A' is a carbamoyl derivative and 'B' is H

| No. | X | n (position) | 1$^{st}$ Chiral | 2$^{nd}$ Chiral | R$^1$ | A<br>A = carbamoyl derivative<br>R$^2$ = | B<br>B = H |
|---|---|---|---|---|---|---|---|
| 1 | Cl | 1(2-) | S | S | Me | H | H |
| 2 | Cl | 1(2-) | R | R | Me | H | H |
| 3 | Cl | 1(2-) | Rac. | Rac. | Me | H | H |
| 4 | Cl | 1(2-) | S | R | Me | H | H |
| 5 | Cl | 1(2-) | R | S | Me | H | H |
| 6 | Cl | 1(2-) | S | S | Et | H | H |
| 7 | Cl | 1(2-) | R | R | Et | H | H |
| 8 | Cl | 1(2-) | Rac. | Rac. | Et | H | H |
| 9 | Cl | 1(2-) | S | S | Isopropyl | H | H |
| 10 | Cl | 1(2-) | R | R | Isopropyl | H | H |
| 11 | Cl | 1(2-) | Rac. | Rac. | Isopropyl | H | H |
| 12 | Cl | 1(2-) | S | S | butyl | H | H |
| 13 | Cl | 1(2-) | R | R | butyl | H | H |
| 14 | Cl | 1(2-) | Rac. | Rac. | butyl | H | H |
| 15 | Cl | 1(2-) | S | S | Me | Me | H |
| 16 | Cl | 1(2-) | S | S | Me | Propyl | H |
| 17 | Cl | 1(2-) | S | S | Me | Isopropyl | H |
| 18 | Cl | 1(2-) | S | S | Me | Cyclopropyl | H |
| 19 | Cl | 1(2-) | S | S | Me | Cyclohexyl | H |
| 20 | Cl | 1(2-) | S | S | Me | Benzyl | H |
| 21 | Cl | 1(2-) | S | S | Me | Bicyclo[2.2.1]heptane | H |
| 22 | Cl | 1(2-) | R | R | Me | Me | H |
| 23 | Cl | 1(2-) | R | R | Me | Propyl | H |
| 24 | Cl | 1(2-) | R | R | Me | Isopropyl | H |
| 25 | Cl | 1(2-) | R | R | Me | Cyclopropyl | H |
| 26 | Cl | 1(2-) | R | R | Me | Cyclohexyl | H |
| 27 | Cl | 1(2-) | R | R | Me | Benzyl | H |
| 28 | Cl | 1(2-) | R | R | Me | Bicyclo[2.2.1]heptane | H |
| 29 | Cl | 1(2-) | Rac. | Rac. | Me | Me | H |
| 30 | Cl | 1(2-) | Rac. | Rac. | Me | Propyl | H |

TABLE 1-continued

Compounds 1 to 67 having the structure of Chemical Formula 1 where 'A' is a carbamoyl derivative and 'B' is H

| No. | X | n (position) | 1st Chiral | 2nd Chiral | R¹ | A A = carbamoyl derivative R² = | B B = H |
|---|---|---|---|---|---|---|---|
| 31 | Cl | 1(2-) | Rac. | Rac. | Me | Isopropyl | H |
| 32 | Cl | 1(2-) | Rac. | Rac. | Me | Cyclopropyl | H |
| 33 | Cl | 1(2-) | Rac. | Rac. | Me | Cyclohexyl | H |
| 34 | Cl | 1(2-) | Rac. | Rac. | Me | Benzyl | H |
| 35 | Cl | 1(2-) | Rac, | Rac. | Me | Bicyclo[2.2.1]heptane | H |
| 36 | Cl | 2(2,4-) | S | S | Me | H | H |
| 37 | Cl | 2(2,6-) | S | S | Me | H | H |
| 38 | Cl | 2(2,3-) | S | S | Me | H | H |
| 39 | Cl | 2(2,4-) | S | S | Et | H | H |
| 40 | Cl | 2(2,6-) | S | S | Et | H | H |
| 41 | Cl | 2(2,4-) | S | S | Isopropyl | H | H |
| 42 | Cl | 2(2,6-) | S | S | Isopropyl | H | H |
| 43 | Cl | 2(2,4-) | S | S | butyl | H | H |
| 44 | Cl | 2(2,6-) | S | S | butyl | H | H |
| 45 | Cl | 2(2,4-) | R | R | Me | H | H |
| 46 | Cl | 2(2,6-) | R | R | Me | H | H |
| 47 | Cl | 2(2,3-) | R | R | Me | H | H |
| 48 | Cl | 2(2,4-) | R | R | Et | H | H |
| 49 | Cl | 2(2,6-) | R | R | Et | H | H |
| 50 | Cl | 2(2,4-) | R | R | Isopropyl | H | H |
| 51 | Cl | 2(2,6-) | R | R | Isopropyl | H | H |
| 52 | Cl | 2(2,4-) | R | R | butyl | H | H |
| 53 | Cl | 2(2,6-) | R | R | butyl | H | H |
| 54 | Cl | 2(2,4-) | Rac, | Rac. | Me | H | H |
| 55 | Cl | 2(2,6-) | Rac, | Rac. | Me | H | H |
| 56 | Cl | 2(2,3-) | Rac, | Rac. | Me | H | H |
| 57 | Cl | 2(2,4-) | Rac, | Rac. | Et | H | H |
| 58 | Cl | 2(2,6-) | Rac, | Rac. | Et | H | H |
| 59 | Cl | 2(2,4-) | Rac, | Rac. | Isopropyl | H | H |
| 60 | Cl | 2(2,6-) | Rac, | Rac. | Isopropyl | H | H |
| 61 | Cl | 2(2,4-) | Rac, | Rac. | butyl | H | H |
| 62 | Cl | 2(2,6-) | Rac, | Rac. | butyl | H | H |
| 63 | F | 1(2-) | S | S | Me | H | H |
| 64 | F | 1(2-) | R | R | Me | H | H |
| 65 | I | 1(2-) | S | S | Me | H | H |
| 66 | I | 1(2-) | R | R | Me | H | H |
| 67 | I | 1(2-) | S | S | Et | H | H |

TABLE 2

Compounds 68 to 115 having the structure of Chemical Formula 1 where 'A' is H and 'B' is a carbamoyl derivative

| No. | X | n (position) | 1st Chiral | 2nd Chiral | R¹ | A A = H | B B = carbamoyl derivative R³ = |
|---|---|---|---|---|---|---|---|
| 68 | Cl | 1(2-) | S | S | Me | H | H |
| 69 | Cl | 1(2-) | R | R | Me | H | H |
| 70 | Cl | 1(2-) | Rac. | Rac. | Me | H | H |
| 71 | Cl | 1(2-) | S | S | Me | H | Me |
| 72 | Cl | 1(2-) | R | R | Me | H | Me |
| 73 | Cl | 1(2-) | Rac. | Rac. | Me | H | Me |
| 74 | Cl | 1(2-) | S | S | Me | H | Propyl |
| 75 | Cl | 1(2-) | R | R | Me | H | Propyl |
| 76 | Cl | 1(2-) | Rac. | Rac. | Me | H | Propyl |
| 77 | Cl | 1(2-) | S | S | Me | H | Isopropyl |
| 78 | Cl | 1(2-) | R | R | Me | H | Isopropyl |
| 79 | Cl | 1(2-) | Rac. | Rac. | Me | H | Isopropyl |
| 80 | Cl | 1(2-) | S | S | Me | H | Cyclopropyl |
| 81 | Cl | 1(2-) | R | R | Me | H | Cyclopropyl |
| 82 | Cl | 1(2-) | Rac. | Rac. | Me | H | Cyclopropyl |
| 83 | Cl | 1(2-) | S | S | Me | H | Cyclohexyl |
| 84 | Cl | 1(2-) | R | R | Me | H | Cyclohexyl |
| 85 | Cl | 1(2-) | Rac. | Rac. | Me | H | Cyclohexyl |
| 86 | Cl | 1(2-) | S | S | Me | H | Benzyl |
| 87 | Cl | 1(2-) | R | R | Me | H | Benzyl |
| 88 | Cl | 1(2-) | Rac. | Rac. | Me | H | Benzyl |
| 89 | Cl | 2(2,4-) | S | S | Me | H | H |
| 90 | Cl | 2(2,6-) | S | S | Me | H | H |
| 91 | Cl | 2(2,3-) | S | S | Me | H | H |
| 92 | Cl | 2(2,4-) | S | S | Et | H | H |
| 93 | Cl | 2(2,6-) | S | S | Et | H | H |
| 94 | Cl | 2(2,4-) | S | S | Isopropyl | H | H |
| 95 | Cl | 2(2,6-) | S | S | Isopropyl | H | H |
| 96 | Cl | 2(2,4-) | S | S | Butyl | H | H |
| 97 | Cl | 2(2,6-) | S | S | Butyl | H | H |
| 98 | Cl | 2(2,4-) | R | R | Me | H | H |
| 99 | Cl | 2(2,6-) | R | R | Me | H | H |
| 100 | Cl | 2(2,3-) | R | R | Me | H | H |
| 101 | Cl | 2(2,4-) | R | R | Et | H | H |
| 102 | Cl | 2(2,6-) | R | R | Et | H | H |
| 103 | Cl | 2(2,4-) | R | R | Isopropyl | H | H |
| 104 | Cl | 2(2,6-) | R | R | Isopropyl | H | H |
| 105 | Cl | 2(2,4-) | R | R | Butyl | H | H |
| 106 | Cl | 2(2,6-) | R | R | Butyl | H | H |
| 107 | Cl | 2(2,4-) | Rac. | Rac. | Me | H | H |
| 108 | Cl | 2(2,6-) | Rac. | Rac. | Me | H | H |
| 109 | Cl | 2(2,3-) | Rac. | Rac. | Me | H | H |

TABLE 2-continued

Compounds 68 to 115 having the structure of Chemical Formula 1 where 'A' is H and 'B' is a carbamoyl derivative

| No. | X | n (position) | 1st Chiral | 2nd Chiral | $R^1$ | A<br>A = H | B<br>B = carbamoyl derivative<br>$R^3 =$ |
|-----|-----|-----|-----|-----|-----|-----|-----|
| 110 | Cl | 2(2,4-) | Rac. | Rac. | Et | H | H |
| 111 | Cl | 2(2,6-) | Rac. | Rac. | Et | H | H |
| 112 | Cl | 2(2,4-) | Rac. | Rac. | Isopropyl | H | H |
| 113 | Cl | 2(2,6-) | Rac. | Rac. | Isopropyl | H | H |
| 114 | Cl | 2(2,4-) | Rac. | Rac. | Butyl | H | H |
| 115 | Cl | 2(2,6-) | Rac. | Rac. | Butyl | H | H |

Experimental Example 1

Examination Using MCAO Model 1.1. Neuro-Prevention Study of Transient MCAO (tMCAO) Model 1.1.1. Preparation of Animals Male, SD rats weighing 290-300 g were purchased from Nara Bio Tech. (Pyoung-tek, Korea) Animals were maintained with laboratory animal food and water ad libitum in an animal facility with a 12 h light/dark cycle at a controlled temperature (23±2° C.) until used. All animal experiments were carried out in accordance with the Korean Academy of Medical Sciences Guide for Care and Use of Laboratory Animals.

1.1.2. Transient Middle Cerebral Artery Occlusion (tMCAO) Surgical Procedure

The rats were anesthetized with isoflurane (Hana-phram., Korea) and anesthesia machine was set to 1.0 L/min $N_2O$ (Surgi-Vet, USA). Isoflurane and $N_2O$ gas ratio was 3:3 for induction anesthesia, and lower to 2:1 (isoflurane:$N_2O$) to maintain anesthesia. Body temperature was monitored continuously by a rectal thermo meter probe and maintained at 37±0.5° C. by placing the animals on a heating pad (Jung-do B&P, Korea). The MCA (middle cerebral artery) occlusion was induced by the procedure of Longa et al. (1989) with minor modifications. Briefly, surgical nylon suture thread (4-0, Diameter: 0.39 mm, Coating length: 0.56 mm, Doccol suture, USA) with a round tip was advanced from the external carotid artery (ECA) into the lumen of the internal carotid artery (ICA) to occlude the origin of the MCA. The wound was closed, and the animals were allowed to home cage for recover.

1.1.3. Administration of Compound of Examples and Testing Schedule

Priority, the infraction areas when the compound of Example 1 was treated at various time points were measured for peak time when is the best efficacy time (see FIG. 1). And then, rats received 60 mg/kg dose of each compound of Examples 1, 65 and 67, intraperitoneally (i.p.) at 15 minutes before MCA occlusion (see FIG. 2, animal numbers of each compound of Examples 1 (n=8), 65 (n=5) and 67 (n=6)). All compounds were dissolved in 30% polyethylene glycol (Compound of Example 1) or 20% (w/v) Tween 80 (Compounds of Examples 65 and 67) once in volume of 4 ul/g bw. Control group (n=33) was identical to those in the MCA occlusion rats except for injection of vehicle (4 ul/g bw of 30% (w/v) polyethylene glycol or 20% (w/v) Tween 80, intraperitoneally (i.p.)). Two hours after MCA occlusion, reperfusion was accomplished by pulling the suture thread back to the bifurcation until the tip cleared the ICA.

1.1.4. Neuro-Therapeutic Study of Transient MCAO Model

Figure 3:
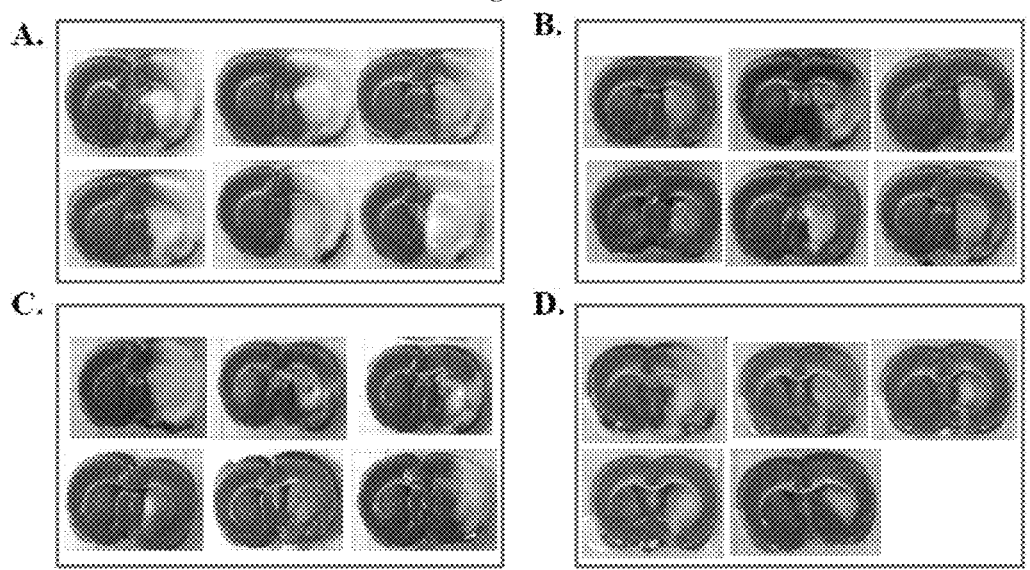
FIG. 3 illustrates coronal sections showing infract area with treatment of the compounds after tMCA occlusion, to show the neuro-therapeutic effect.

The experimentation was identical performed as described in Experimental Example 1.1, except that each compound examples of 1, 65 and 67 was administered at 15 minutes after MCA occlusion (FIG. 3, animal numbers of each compound of Examples 1 (n=7), 65 (n=6) and 67 (n=5)), to test the therapeutic effect of the compounds. Control group (n=33) was identical to those in the MCA occlusion rats except for injection of vehicle (4 ul/g bw of 30% polyethylene glycol or 20% Tween 80, intraperitoneally (i.p.)).

1.2. Neuro-Therapeutic Study of Permanent MCAO (pMCAO) Model 1.2.1. Preparation of Animals Male, SD rats weighing 290-300 g were purchased from Nara Bio Tech. (Pyoung-tek, Korea) Animals were maintained with laboratory animal food and water ad libitum in our animal facility with a 12 h light/dark cycle at a controlled temperature (23±2° C.) until used. All animal experiments were carried out in accordance with the Korean Academy of Medical Sciences Guide for Care and Use of Laboratory Animals.

1.2.2. Permanent Middle Cerebral Artery Occlusion (pMCAO) Surgical Procedure

The rats were anesthetized with isoflurane (Hana-phram., Korea) and anesthesia machine should be set to 1.0 L/min $N_2O$ (Surgi-Vet, USA). Isoflurane and $N_2O$ gas ratio was 3:3 for induction anesthesia and lower to 2:1 (isoflurane:$N_2O$) to maintain anesthesia. Body temperature was monitored continuously by a rectal thermo meter probe and maintained at 37±0.5° C. by placing the animals on a heating pad (Jung-do B&P, Korea). The MCA occlusion was induced by the procedure of Longa et al. (1989) with minor modifications. Briefly, surgical nylon suture thread (4-0, Diameter: 0.39 mm, Coating length: 0.56 mm, Doccol suture, USA) with a round tip was advanced from the external carotid artery (ECA) into the lumen of the internal carotid artery (ICA) to occlude the origin of the MCA. The wound was closed, and the animals were allowed to home cage for recover.

1.2.3. Administration of Compound of Example 1 and Testing Schedule

Rats received 60 mg/kg dose of compound of examples 1, intraperitoneally (i.p.) bis in die (b.id., it means twice daily injection, 8 hours after first injection) at 15 minutes (see FIGS. 5, 6), 1 hour and 2 hours (see FIGS. 7, 8) after MCA occlusion, firstly. And rats were occluded MCA for 1 day, 3 days and 7 days each other. Compound of example 1 was dissolved in 30% polyethylene glycol in volume of 4 ul/g bw. Control groups were identical to those in the MCA occlusion rats except for injection of vehicle (4 ul/g bw of 30% polyethylene). In contrast of tMCAO models, pMCAO models were not need reperfusion procedure.

1.3. Data Analysis of Cerebral Infarct Area 1.3.1. Measurement of Cerebral Infarction Area in tMCAO Model After 24 hours of reperfusion, rats were anesthetized with isoflurane (Hana-phram., Korea). The brain was then quickly removed and cut into 2-mm thick coronal block slices in brain matrix. The slices were immersed in a 2% (w/v) solution of 2,3,5-triphenyltetrazolium chloride (TTC) in normal saline at 37° C. for 10 min and then fixed in 10% (v/v) formalin solution at room temperature for overnight. The TTC stained brain slices were photographed using a digital camera (5000D, Nikon, Japan). The size of infarct was calculated with an image analysis system (Image-Pro Plus 4.0, Media Cybernetics, USA) and measurement of infarct area were expressed as the percentage (% control) of infarct area in reference to the compared with ipsilateral hemisphere of control group (see FIGS. 2 and 3).

Statistical analysis results are presented as the mean±S.E.M. and measures analysis of variance was used for comparison of the results of hemispheric infarct area, obtained from 5~33 rats in each group. Data were analyzed by either one-way analysis of variance (ANOVA) followed by Tukey's test for multiple comparisons. p values less than 0.05 were considered to be statistically significant (see FIGS. 1 and 4).

1.3.2. Measurement of Cerebral Area in pMCAO Model

Measurements of cerebral infarction area in pMCAO model groups were performed as described in Experimental Example 1.3.1. above (see FIGS. 5 to 8)

1.4. Results

The TTC-stained infarction area with treatment of each compound of Examples 1, 65, and 67 was significantly reduced both tMCAO model which rats subjected to 2 h of ischemia (occlusion) and 24 h of reperfusion and pMCAO model which rats subjected to 1 day, 3 days and 7 days of ischemia (occlusion). The tMCAO animals received with an administration of 60 mg/kg (i.p.) compound example 1 at the 15 min before or after 2 hr of occlusion (see FIGS. 1 to 4) and pMCAO animals received b.i.d. (bis in die; twice daily) (8 hrs interval) from firstly administration of 60 mg/kg (i.p.) compound example 1 at 15 min after occlusion for 1 day, 3 days and 7 days (see FIGS. 5 to 8). The obtained results are shown in FIGS. 1 to 8.

1.4.1. Effects on tMCAO Models

FIG. 1 shows the TTC-stained infarction area (% control) with treatment the compound example 1 on tMCAO at various time points, wherein all data represent mean±S.E.M. (FIGS. 1, 4, 6 and 8). The relevant infarct area was calculated with an image analysis system and expressed as the percentage (% control) of infarct area in reference to the compared with ipsilateral hemisphere of control group. Statistical analysis was used by One-way ANOVA: $F(7.76)=19.81$, $p<0.0001$ (Tukey's test), ***; vs Ctrl, $p<0.001$, +++; vs −0.5 hr, $p<0.001$, #; vs −0.25 hr, $p<0.05$, ###; vs −0.25 hr, $p<0.001$, ^^^ vs 0 hr, $p<0.001$, \$\$\$; vs +0.25 hr, $p<0.001$, &&& vs +0.5 hr, $p<0.001$.

Figure 2:
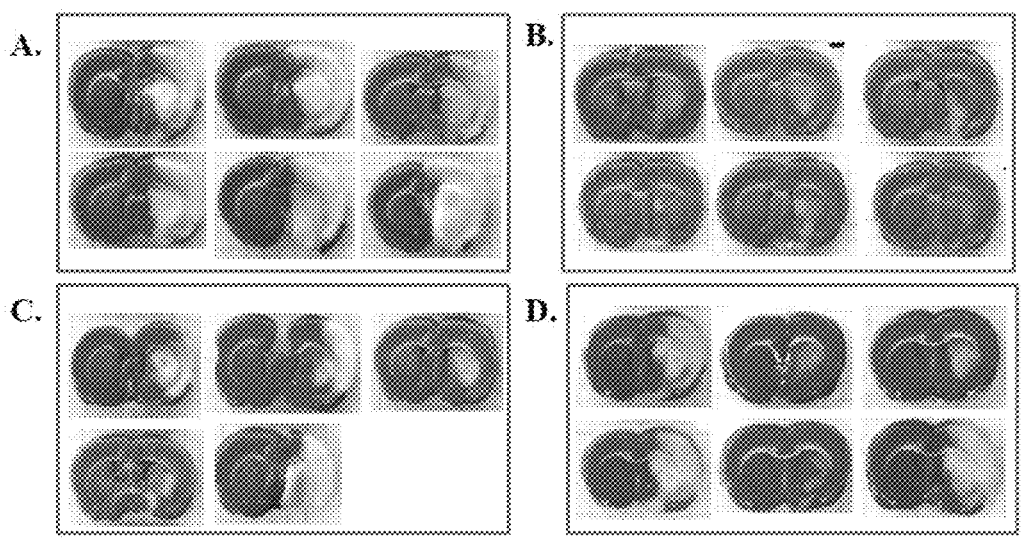
FIG. 2 illustrates coronal sections showing infract area with treatment of the compounds before tMCA occlusion, to show the neuro-prevention effect.

FIG. 2 illustrates coronal TTC-stained sections showing representative infract area images in cortex and striatum, where the sections obtained from the tested animals treated with the compound examples at 15 minutes before tMCA occlusion (A: Control (occlusion for 2 hr, reperfusion 24 hr), vehicle (30% PEG400 or 20% Tween 80) administration, 60 mg/kg, i.p. (administration: 0.25 hr before occlusion), n=33;

B: Compound 1 (Example 1) administration (occlusion for 2 hr, reperfusion 24 hr), 60 mg/kg, i.p., (administration: 0.25 hr before occlusion), n=8;

C: Compound 65 (Example 65) administration (occlusion for 2 hr, reperfusion 24 hr), 60 mg/kg, i.p., (administration: 0.25 hr before occlusion), n=5; and D: Compound 67 (Example 67) administration (occlusion for 2 hr, reperfusion 24 hr), 60 mg/kg, i.p., (administration: 0.25 hr before occlusion), n=6).

As shown in FIG. 2, when rats was subjected to 2 hr of occlusion, 24 hr reperfusion, and administration of Compound 1, 65 or 67 before occlusion, the infraction areas were significantly reduced compared with that of the control, indicating that all of Compounds 1, 65 and 67 (especially Compound 1) have neuro-prevention effects.

FIG. 3 Illustrative coronal TTC-stained sections showing representative infract area images in cortex and striatum, where the sections obtained from the tested animals treated with the compound examples at 15 minutes after MCA occlusion.

(A: Control (occlusion for 2 hr, reperfusion 24 hr), vehicle (30% PEG400 or 20% Tween 80) administration, 60 mg/kg, i.p. (administration: 0.25 hr after occlusion), n=33

B: Compound 1 administration (occlusion for 2 hr, reperfusion 24 hr), 60 mg/kg, i.p., (administration: 0.25 hr after occlusion), n=8

C: Compound 65 administration (occlusion for 2 hr, reperfusion 24 hr), 60 mg/kg, i.p., (administration: 0.25 hr after occlusion), n=5

D: Compound 67 administration (occlusion for 2 hr, reperfusion 24 hr), 60 mg/kg, i.p., (administration: 0.25 hr after occlusion), n=6)

As shown in FIG. 3, when rats was subjected to 2 hr of occlusion, 24 hr reperfusion, and administration of Compound 1, 65 or 67 after occlusion, the infraction areas were significantly reduced compared with that of the control, indicating that all of Compounds 1, 65 and 67 have neuro-therapeutic effects.

Figure 4:
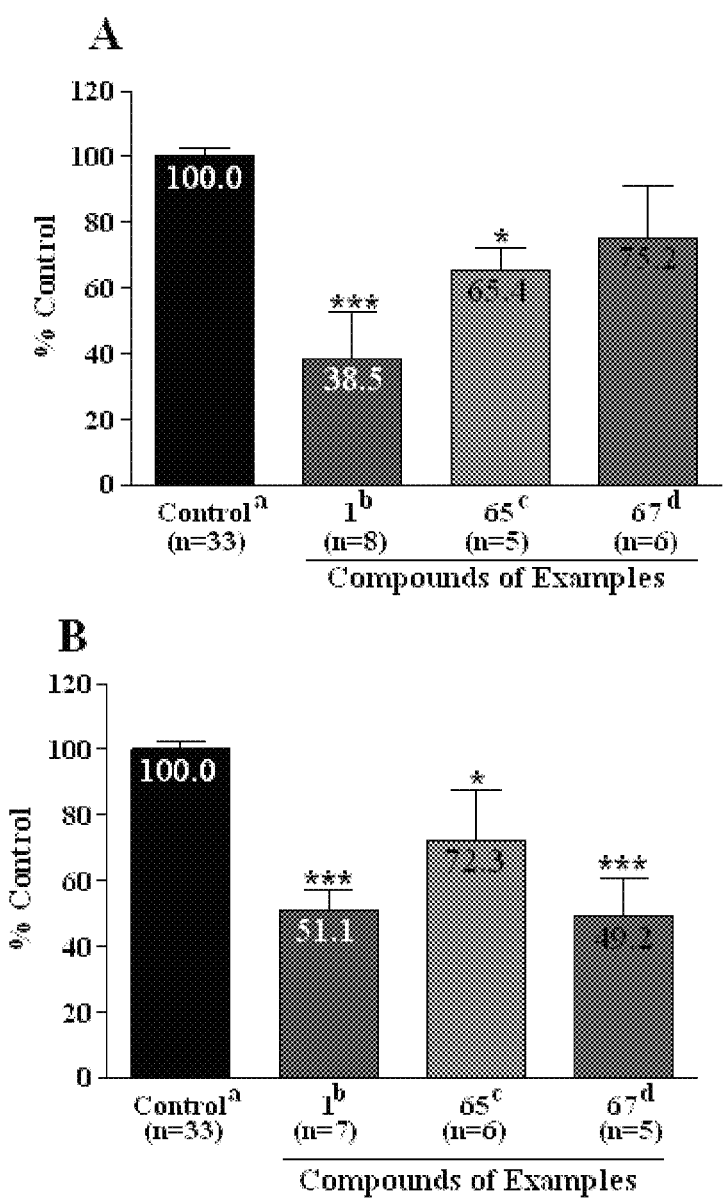
FIG. 4 is a graph showing the relevant size of infarct with treatment of the compounds before (A) and after (B) tMCA occlusion.

FIG. 4 is a graph showing the relevant size of TTC-stained infarction area with treatment of each Compound 1, 65 or 67 (60 mg/kg) on tMCAO models at 15 minutes before (A) or after (B) occlusion. All data represent mean±S.E.M. The relevant infarct area was calculated with an image analysis system and expressed as the percentage (% control) of infarct area in reference to the compared with ipsilateral hemisphere of control group.

(A)

a: Control (occlusion for 2 hr, reperfusion 24 hr), vehicle (30% PEG400 or 20% Tween 80), i.p. (administration: 0.25 hr before occlusion), n=33;

b: Compound 1 administration (occlusion for 2 hr, reperfusion 24 hr), 60 mg/kg, i.p., (administration: 0.25 hr before occlusion), n=8;

c: Compound 65 administration (occlusion for 2 hr, reperfusion 24 hr), 60 mg/kg, i.p., (administration: 0.25 hr before occlusion), n=5; and d: Compound 67 administration (occlusion for 2 hr, reperfusion 24 hr), 60 mg/kg, i.p., (administration: 0.25 hr before occlusion), n=6.

(B)

a: Control (occlusion for 2 hr, reperfusion 24 hr), vehicle (30% PEG400 or 20% Tween 80), i.p. (administration: 0.25 hr after occlusion), n=33;

b: Compound 1 administration (occlusion for 2 hr, reperfusion 24 hr), 60 mg/kg, i.p., (administration: 0.25 hr after occlusion), n=8;

c: Compound 65 administration (occlusion for 2 hr, reperfusion 24 hr), 60 mg/kg, i.p., (administration: 0.25 hr after occlusion), n=5; and d: Compound 67 administration (occlusion for 2 hr, reperfusion 24 hr), 60 mg/kg, i.p., (administration: 0.25 hr after occlusion), n=6

Statistical analysis of prevention tMCAO model (A) was used by One-way ANOVA: $F(3.52)=16.54$, $p<0.0001$ (Tukey's test),***; vs Control, $p<0.001$, *; vs Control, $p<0.05$, and Statistical analysis of therapeutic tMCAO model (B) was used by One-way ANOVA: $F(3.51)=21.62$, $p<0.0001$ (Tukey's test),***; vs Control, $p<0.001$, *; vs Control, $p<0.05$.

1.4.2. Effects on pMCAO Models

Figure 5:
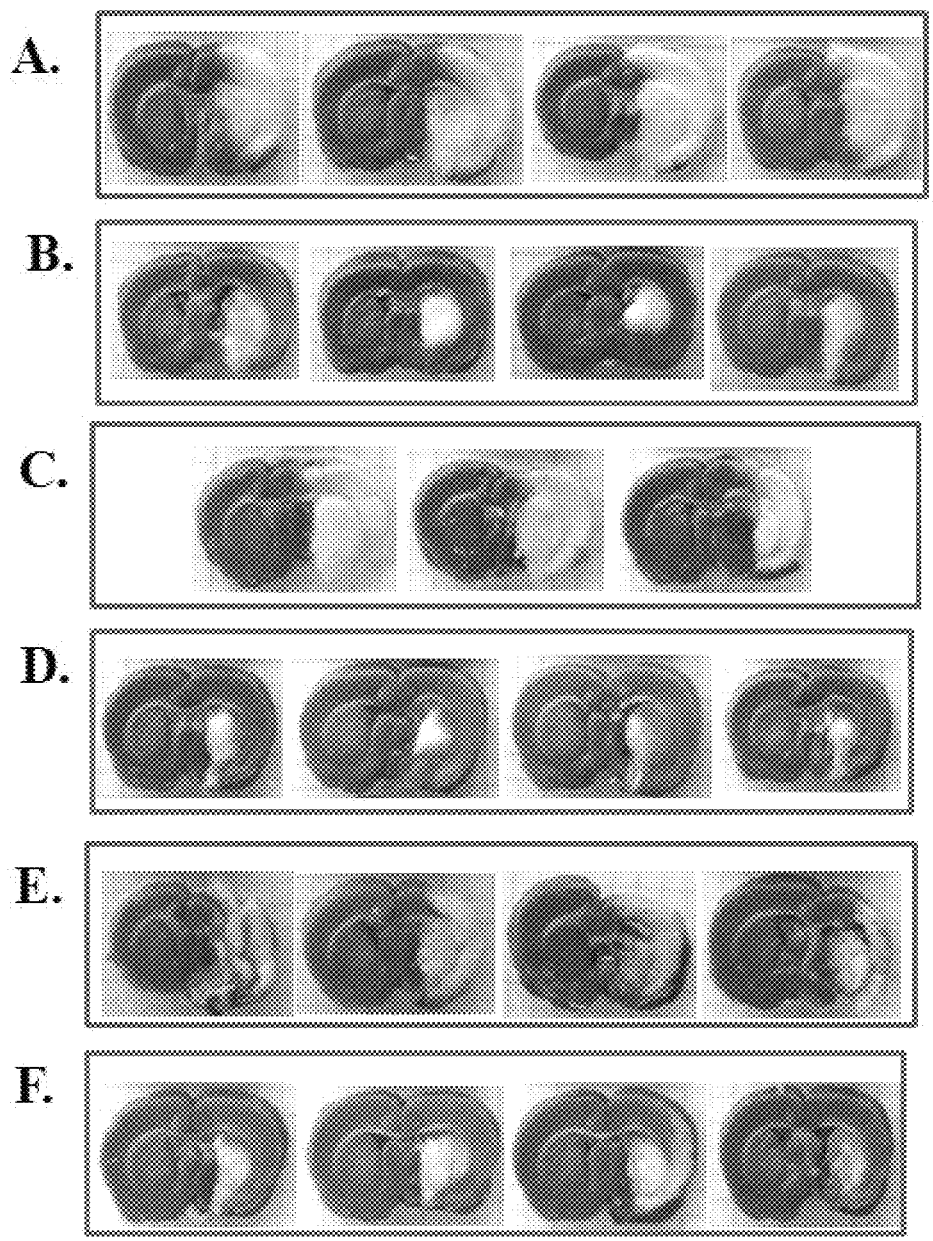
FIG. 5 illustrates coronal TTC-stained sections showing infract area with treatment of 60 mg/kg of Compound 1 or vehicle at 15 minutes after pMCA occlusion.

FIG. 5 illustrates coronal TTC-stained sections showing infract area in cortex and striatum, where the sections obtained from the tested animals treated with 60 mg/kg of Compound 1 or vehicle in the same volume for control groups at 15 minutes after pMCA occlusion and 8 hr after first treatment as b.i.d. Rats subjected to occlusion for 1 day, 3 days and 7 days each other. The results are showing the neuro-therapeutic effect of the compound example 1.

(A: Control (occlusion for 1 day), vehicle (30% PEG400), 60 mg/kg, i.p., b.i.d. (1st inj.: 0.25 hr after occlusion, 8 hr interval), n=9;

B: Day 1 Treatment (occlusion for 1 day), Compound 1, 60 mg/kg, i.p., b.i.d. (1st inj.: 0.25 hr after occlusion, 8 hr interval), n=8;

C: Control (occlusion for 3 days), vehicle (30% PEG400), i.p., b.i.d. (1st inj.: 0.25 hr after occlusion, 8 hr interval), n=3;

D: Day 3 Treatment (occlusion for 3 days), Compound 1, 60 mg/kg, i.p., b.i.d. (1st inj.: 0.25 hr after occlusion, 8 hr interval), n=5;

E: Control (occlusion for 7 days), vehicle (30% PEG400), i.p., b.i.d. (1st inj.: 0.25 hr after occlusion, 8 hr interval), n=5; and F: Day 7 Treatment (occlusion for 7 days), Compound 1, 60 mg/kg, i.p., b.i.d. (1st inj.: 0.25 hr after occlusion, 8 hr interval), n=9)

As shown in FIG. 5, when Compound 1 is treated, the infraction areas were significantly reduced compared with the control, indicating that Compounds 1, 65 and 67 have neuro-therapeutic effects in pMCA occlusion model.

Figure 6:
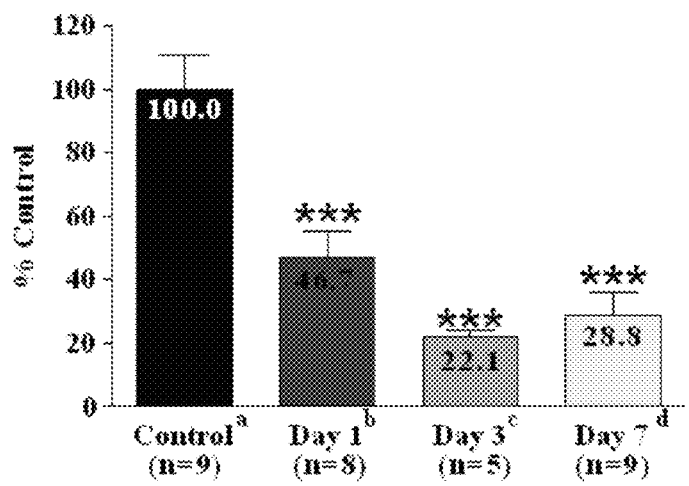
FIG. 6 is a graph showing the relevant size of infarct with treatment of Compound 1 at 15 minutes after pMCA occlusion.

FIG. 6 shows effects of TTC-stained infarction area for 1 day 3 days and 7 days occlusions with treatment Compound 1 on pMCAO, intraperitoneally (i.p.) bis in die (b.i.d., it means twice daily injection, 8 hours after first injection) at 15 minutes after occlusion firstly. All data represent mean±S.E.M.

(a: Control (occlusion for 1 day), vehicle (30% PEG400), ip, b.i.d. (1st inj.: 0.25 hr after occlusion, 8 hr interval), n=9, b: Day 1 Treatment (occlusion for 1 days), compound example 1, 60 mg/kg, ip, b.i.d. (1st inj.: 0.25 hr after occlusion, 8 hr interval), n=8, c: Day 3 Treatment (occlusion for 3 days), compound example 1, 60 mg/kg, ip, b.i.d. (1st inj.: 0.25 hr after occlusion, 8 hr interval), n=5, and d: Day 7 Treatment (occlusion for 7 days), compound example 1, 60 mg/kg, ip, b.i.d. (1st inj.: 0.25 hr after occlusion, 8 hr interval), n=9)

Figure 7:
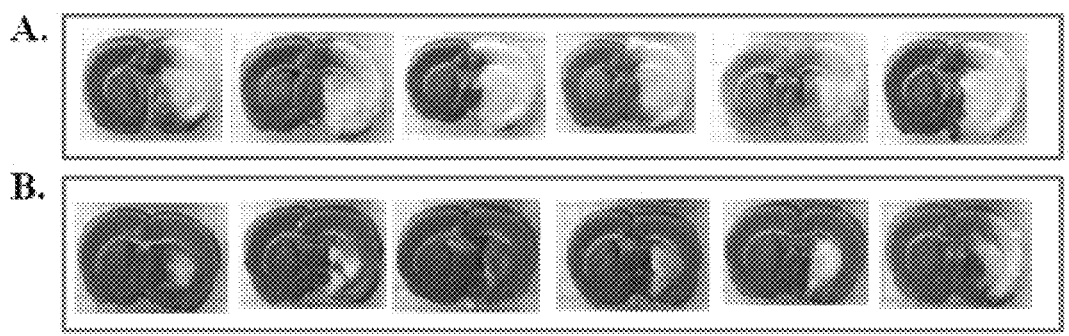
FIG. 7 illustrates coronal TTC-stained sections showing infract area with treatment of 60 mg/kg of Compound 1 or vehicle at 1 hour after pMCA occlusion.

Infarction areas were measured based on only Day 1 control group as % control, because of other control groups (Day 3, 7) cannot be measured infarction areas due to abnormal structure of damaged tissue in brain section. Statistical analysis was used by One-way ANOVA; $F(3.27)=16.84$, $p<0.0001$ (Tukey's test), *** vs Control; $p<0.001$ FIG. 7 illustrates coronal TTC-stained sections showing infract area in cortex and striatum, where the sections obtained from the tested animals treated with 60 mg/kg of Compound 1 or vehicle in the same volume for control groups at 1 hour after pMCA occlusion and 8 hr after first treatment as b.i.d.

(A: Day 1 control (occlusion for 1 day), vehicle (30% PEG400), i.p., b.i.d. (1st inj.: 1 hr after occlusion, 8 hr interval), n=9, and B: Day 3 Treatment (occlusion for 3 days), Compound 1, 60 mg/kg, i.p., b.i.d. (1st inj.: 1 hr after occlusion, 8 hr interval), n=6)

The results are showing the neuro-therapeutic effect of Compound 1 in the group of treatment at 1 hr after occlusion for 3 days.

Figure 8:
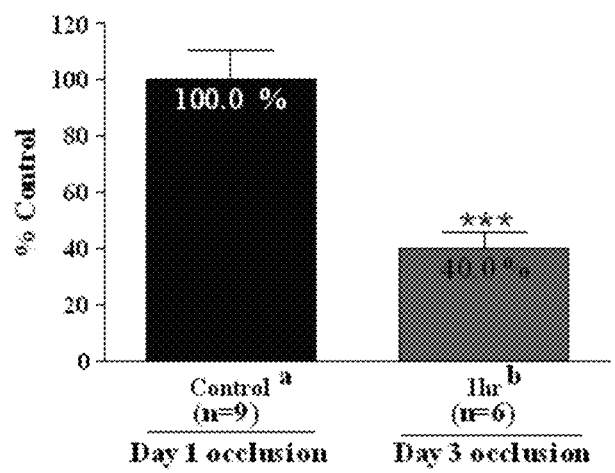
FIG. 8 is a graph showing the relevant size of infarct with treatment of Compound 1 at 1 hour after pMCA occlusion.

FIG. 8 shows effects of TTC-stained infarction area for 3 days with treatment the compound example 1 on pMCAO, intraperitoneally (i.p.), b.i.d. at 1 hour after occlusion first administration. All data represent mean±S.E.M.

(a: Day 1 control (occlusion for 1 day), vehicle (30% PEG400), ip, b.i.d. (1st inj.: 1 hr after occlusion, 8 hr interval), n=9, and b: Day 3 Treatment (occlusion for 3 days), compound example 1, 60 mg/kg, ip, b.i.d. (1st inj.: 1 hr after occlusion, 8 hr interval), n=6)

Infarction areas were presented based on only Day 1 control group as % control, because other control groups (Day 3) cannot be measured infarction areas due to abnormal structure of damaged tissue in brain section. Statistical analysis was used by One-way ANOVA; $F(2.15)=10.82$, $p<0.0001$ (Tukey's test), ** vs Control; $p<0.01$ Experimental Example 2

Measurement of Anti-Excitotoxicity Activity

In the MES test (Ref., G. Villetti et al. Neuropharmacology 40 (2001) 866-878), an electrical stimulus (mice; 50 mA, 60 Hz, 0.2 sec and rats; 150 mA 60 Hz, 0.2 sec in the test animal) supplied by 11A Shocker (IITC Life Science Company) was delivered through corneal electrodes. All mice or rats assigned to any electroshock at peak time were treated with each test compound sample which was dissolved in 30% PEG400 prepared by saline solvent applied to oral before the test. If the test animal stretching their hind limb in a straight line weren't observed in the MES test, the results indicate that the test sample had an anti-epilepsy activity. Three doses of the test sample were administered orally to over 18 mice (6 mice per dose) for evaluating the respective doses at which 50% of the animals are protected from seizure (ED50). The value of ED50 (median effective dose) is calculated by Litchfield and Wicoxon log-probit method which is a dose-response relationship. Then, the test results are shown in following Table 3. Experimental animal, male ICR mice and male SD rats, were purchased from OrientBio or Nara biotech, Korea, and housed 4-5 mice per a cage for 4-5 days. The range of mice body weight was used between 19 and 26 grams and range of rats body weight was used between 100 and 130 grams.

Experimental Example 3

Measurement of Neurotoxicity

The measurement of neurotoxicity of the test compounds was conducted by the method of Dunham and Miya [Dunham, N. W. and Miya, T. S. 1957. A note on a simple apparatus for detecting neurological deficit in rats and mice. J. Am. Pharm. Assoc. (Baltimore) 46: 208-209]. In the method, motor abilities of the test animals can be determined by observing whether the test animals can walk without falling from a rotator, thereby determining the value of neurotoxicity of each compound. Term "TD50" means the respective dose of the test compound at which 50% of the test animal exhibit neurotoxicity. They were pre-trained on the rotaroid (Rotarod; Columbus instrument, rota-max, USA) at 6 rpm for 5 min 24 hr prior to the test. The peak time was determined by administration test material's random dose for 0.5, 1, 2, 4 hour. To evaluate the minimal neurotoxicity of the compound, the mice were placed on the Rotarod (rod circle; 3 Cm) at 6 rpm and the test animal fails to maintain walking once or more during 1 minute, it can be regarded that the test animal exhibits neurotoxicity. The ratio of TD50 to ED50 (TD50/ED50) is called as a protective index, and useful as a parameter for comparison of pharmaceutical efficacy and neurotoxicity. The obtained results are shown in following Table 3.

TABLE 3

Measurement results of anti-excitotoxicity activity and neurotoxicity of compounds in the test animals (Mice and Rats)

| Compound No. | MES test(po) ED50(mg/kg) | Peak Time(h) | TD50 (mg/kg po) |
|---|---|---|---|
| 1 | 13.0 | 2 | 218.1 |
| 2 | 51.0 | 0.25 | 372.0 |
| 3 | 31.4 | 2 | 378.3 |
| 4 | 82.4 | 0.5 | |
| 5 | 84.1 | 0.5 | 275.2 |
| 6 | 22.2 | 1 | |
| 8 | 100 $^a$(100%) | | |
| 9 | 67.1 | 0.5 | |
| 12 | 100 $^a$(75%) | | |
| 13 | 200 $^a$(75%) | | |
| 14 | 200 $^a$(100%) | | |
| 15 | 100 $^a$(75%) | | |
| 16 | 200 $^a$(25%) | | |
| 18 | 200 $^a$(100%) | | |
| 23 | 200 $^a$(25%) | | |
| 25 | 200 $^a$(25%) | | |
| 29 | 200 $^a$(75%) | | |
| 30 | 200 $^a$(25%) | | |
| 31 | 200 $^a$(25%) | | |
| 32 | 200 $^a$(100%) | | |
| 36 | 82.8 | | |
| 37 | 25.8 | 0.25 | 131.6 |
| 38 | 91.4 | 2 | |
| 39 | 41.2 | 1 | |
| 40 | 46.9 | | |
| 42 | 35.2 | 0.5 | |
| 43 | 100 $^a$(25%) | | |
| 44 | 100 $^a$(75%) | | |
| 45 | 200 $^a$(0%) | | |
| 46 | 35.2 | 1 | |
| 63 | 50 $^a$(100%) | | |
| 65 | 50 $^a$(100%) | | |
| 67 | 100 $^a$(100%) | | |

$^a$Injection amount(mg/kg), Protection %(4 mice);
$^b$Injection amount(mg/kg), Protection %(6 Rats);

[Statistical Analysis]

The obtained results are shown as mean±sem. The difference between the groups was statistically analyzed by ANOVA, and then, further examined by Dunnett's test or Bonferroni test. If p is less than 0.05, it was determined that the difference between the groups had statistical significance.

What is claimed is:

1. A method of treating stroke comprising administering a pharmaceutically effective amount of a phenyl carbamate compound represented by Chemical Formula 1 or a pharmaceutically acceptable salt thereof, to a subject in need thereof:

[Chemical formula 1]

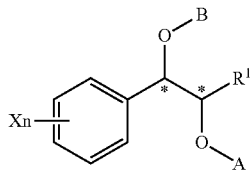

wherein

X is a halogen;

n is an integer from 1 to 5;

R$^1$ is a linear or branched alkyl group of C$_1$-C$_4$;

A is hydrogen or a carbamoyl derivative represented by

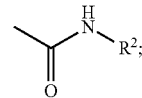

B is hydrogen, a carbamoyl derivative represented by

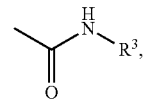

trialkyl silyl groups, trialkylaryl silyl groups (wherein the total number of alkyl and aryl groups is three), or a trialkyl silyl ether group, wherein each alkyl group is independently selected from the group consisting of linear, branched, or cyclic C$_1$-C$_4$ alkyl groups, and each aryl group is independently selected from the group consisting of C$_5$-C$_8$ aryl groups;

A and B are not carbamoyl derivatives at same time; and

R$^2$ and R$^3$ may be the same as or different from each other, and independently selected from the group consisting of hydrogen, a linear or branched alkyl group of C$_1$-C$_4$, a cycloalkyl group of C$_3$-C$_8$, and benzyl group.

2. The method according to claim 1, wherein

X is chlorine, fluorine, iodine, or bromine;

n is 1 or 2;

R$^1$ is methyl group, ethyl group, isopropyl group, or butyl group;

A is hydrogen or a carbamoyl derivative represented by

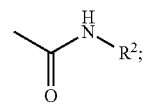

B is hydrogen, a carbamoyl derivative represented by

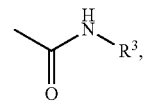

a trimethyl silyl (TMS) group, a triethyl silyl (TES) group, a triisopropyl silyl (TIPS) group, t-butyl dimethyl silyl (TBDMS) group, a t-butyl diphenyl silyl (TBDPS) group, or a trialkyl silyl ether group, wherein each alkyl group is independently selected from the group consisting of linear, branched, or cyclic C$_1$-C$_4$ alkyl groups;

A and B are not carbamoyl derivatives at same time; and R$^2$ and R$^3$ are the same as or different from each other, and independently selected from the group consisting of hydrogen, methyl group, propyl group, isopropyl group, cyclopropyl group, cyclohexyl group, bicycloheptane group, and benzyl group.

3. The method according to claim 1, wherein the compound is selected from the group consisting of:

1-(2-chlorophenyl)-1-hydroxypropyl-2-carbamate, 1-(2-chlorophenyl)-1-hydroxybutyl-2-carbamate, 1-(2-chlorophenyl)-1-hydroxy-3-methyl-butyl-2-carbamate,
1-(2-chlorophenyl)-1-hydroxyhexyl-2-carbamate,
1-(2-chlorophenyl)-1-hydroxypropyl-2-N-methylcarbamate,
1-(2-chlorophenyl)-1-hydroxypropyl-2-N-propylcarbamate, 1-(2-chlorophenyl)-1-hydroxypropyl-2-N-isopropylcarbamate, 1-(2-chlorophenyl)-1-hydroxypropyl-2-N-cyclopropylcarbamate, 1-(2-chlorophenyl)-1-hydroxypropyl-2-N-cyclohexylcarbamate, 1-(2-chlorophenyl)-1-hydroxypropyl-2-N-benzylcarbamate, 1-(2-chlorophenyl)-1-hydroxypropyl-2-N-bicyclo[2,2,1]heptanecarbamate,
1-(2,4-dichlorophenyl)-1-hydroxypropyl-2-carbamate,
1-(2,6-dichlorophenyl)-1-hydroxypropyl-2-carbamate,
1-(2,4-dichlorophenyl)-1-hydroxybutyl-2-carbamate,
1-(2,6-dichlorophenyl)-1-hydroxybutyl-2-carbamate,
1-(2,4-dichlorophenyl)-1-hydroxy-3-methyl-butyl-2-carbamate,
1-(2,6-dichlorophenyl)-1-hydroxy-3-methyl-butyl-2-carbamate,
1-(2,4-dichlorophenyl)-1-hydroxyhexyl-2-carbamate,
1-(2,6-dichlorophenyl)-1-hydroxyhexyl-2-carbamate,
1-(2-chlorophenyl)-2-hydroxypropyl-1-carbamate,
1-(2-chlorophenyl)-2-hydroxypropyl-1-N-methylcarbamate,
1-(2-chlorophenyl)-2-hydroxypropyl-1-N-propylcarbamate,
1-(2-chlorophenyl)-2-hydroxypropyl-1-N-isopropylcarbamate,
1-(2-chlorophenyl)-2-hydroxypropyl-1-N-cyclopropylcarbamate,
1-(2-chlorophenyl)-2-hydroxypropyl-1-N-cyclohexylcarbamate,
1-(2-chlorophenyl)-2-hydroxypropyl-1-N-benzylcarbamate,
1-(2,4-dichlorophenyl)-2-hydroxypropyl-1-carbamate,
1-(2,6-dichlorophenyl)-2-hydroxypropyl-1-carbamate,
1-(2,4-dichlorophenyl)-2-hydroxybutyl-1-carbamate,
1-(2,6-dichlorophenyl)-2-hydroxybutyl-1-carbamate,
1-(2,4-dichlorophenyl)-2-hydroxy-3-methyl-butyl-1-carbamate,
1-(2,6-dichlorophenyl)-2-hydroxy-3-methyl-butyl-1-carbamate,
1-(2,4-dichlorophenyl)-2-hydroxyhexyl-1-carbamate,
1-(2,6-dichlorophenyl)-2-hydroxyhexyl-1-carbamate,
1-(2-fluorophenyl)-1-hydroxypropyl-2-carbamate,
1-(2-iodophenyl)-1-hydroxypropyl-2-carbamate,
1-(2-iodophenyl)-1-hydroxybutyl-2-carbamate,
1-(2,3-dichlorophenyl)-1-hydroxypropyl-2-carbamate, and
1-(2,3-dichlorophenyl)-2-hydroxypropyl-1-carbamate.

4. The method according to claim 1, wherein the compound is in the form of racemate, enantiomer, diastereomer, a mixture of enantiomer, or a mixture of diastereomer.

5. The method according to claim 1, wherein the stroke is an ischemic stroke or a hemorrhagic stroke.

* * * * *